United States Patent
Gill

(10) Patent No.: US 10,369,024 B2
(45) Date of Patent: Aug. 6, 2019

(54) SYSTEMS AND METHODS FOR PROSTHETIC WRIST ROTATION

(71) Applicant: Touch Bionics Limited, Livingston (GB)

(72) Inventor: Hugh Gill, Paisley (GB)

(73) Assignee: Touch Bionics Limited, Livingston (GB)

( * ) Notice: Subject to any disclaimer, the term of this patent is extended or adjusted under 35 U.S.C. 154(b) by 0 days.

(21) Appl. No.: 15/341,939

(22) Filed: Nov. 2, 2016

(65) Prior Publication Data

US 2018/0064563 A1 Mar. 8, 2018

Related U.S. Application Data

(60) Provisional application No. 62/382,919, filed on Sep. 2, 2016.

(51) Int. Cl.
*A61F 2/58* (2006.01)
*A61F 2/68* (2006.01)
(Continued)

(52) U.S. Cl.
CPC ........... *A61F 2/72* (2013.01); *A61F 2/583* (2013.01); *A61F 2/585* (2013.01); *A61F 2/586* (2013.01);
(Continued)

(58) Field of Classification Search
CPC .......... A61F 2/583; A61F 2/585; A61F 2/586; A61F 2/588; A61F 2/70; A61F 2/72;
(Continued)

(56) References Cited

U.S. PATENT DOCUMENTS

| | | | |
|---|---|---|---|
| 1,507,682 | A | 9/1924 | Pecorella et al. |
| 2,477,463 | A | 7/1949 | Otterman |

(Continued)

FOREIGN PATENT DOCUMENTS

| | | |
|---|---|---|
| CN | 1803413 | 7/2006 |
| DE | 309 367 | 11/1918 |

(Continued)

OTHER PUBLICATIONS

Kyberd, Peter. Two degree of freedom powered prosthetic wrist. Journal of Rehabilitation Research and Development. vol. 48, No. 6, 2011.*

(Continued)

*Primary Examiner* — Christie L Bahena
(74) *Attorney, Agent, or Firm* — Knobbe Martens Olson & Bear LLP

(57) ABSTRACT

Features for a prosthetic wrist and associated methods of rotation are described. The prosthetic wrist attaches to a prosthetic hand. Rotation of the prosthetic wrist is performed in combination with grip formation of the prosthetic hand. An IMU provides data associated with the orientation of the prosthetic hand. A desired grip for the prosthetic hand is selected, for example by gesture control. A rotation for the prosthetic wrist is determined based on the orientation of the prosthetic hand from the IMU data and on the selected desired grip. The prosthetic wrist techniques can also be used in combination with prosthetic arms, elbows and/or shoulders. Example structural configurations for the prosthetic wrist and hand are also provided.

18 Claims, 30 Drawing Sheets

(51) Int. Cl.
  *A61F 2/70* (2006.01)
  *A61F 2/72* (2006.01)
  *A61F 2/76* (2006.01)

(52) U.S. Cl.
  CPC .................. *A61F 2/68* (2013.01); *A61F 2/70* (2013.01); *A61F 2002/587* (2013.01); *A61F 2002/704* (2013.01); *A61F 2002/707* (2013.01); *A61F 2002/764* (2013.01)

(58) Field of Classification Search
  CPC .......... A61F 2002/587; A61F 2002/701; A61F 2002/763; A61F 2002/7615; A61F 2002/762; A61F 2002/7625
  See application file for complete search history.

(56) References Cited

U.S. PATENT DOCUMENTS

| | | |
|---|---|---|
| 2,482,555 A | 9/1949 | Otterman |
| 2,508,156 A | 5/1950 | Gillman |
| 2,516,791 A | 7/1950 | Motis et al. |
| 2,592,842 A | 4/1952 | Alderson |
| 2,669,727 A | 2/1954 | Opuszenski |
| 2,983,162 A | 5/1961 | Musser |
| 3,406,584 A | 10/1968 | Roantree |
| 3,509,583 A | 5/1970 | Fraioli |
| 3,683,423 A | 8/1972 | Crapanzano |
| 3,751,995 A | 8/1973 | Carlson |
| 3,837,010 A | 9/1974 | Prout |
| 3,866,246 A | 2/1975 | Seamone et al. |
| 3,883,900 A | 5/1975 | Jerard et al. |
| 3,922,930 A | 12/1975 | Fletcher et al. |
| 4,030,141 A | 6/1977 | Graupe |
| 4,044,274 A | 8/1977 | Ohm |
| 4,114,464 A | 9/1978 | Schubert et al. |
| 4,197,592 A | 4/1980 | Klein |
| 4,398,110 A | 8/1983 | Flinchbaugh et al. |
| 4,558,704 A | 12/1985 | Petrofsky |
| 4,577,127 A | 3/1986 | Ferree et al. |
| 4,623,354 A | 11/1986 | Childress et al. |
| 4,678,952 A | 7/1987 | Peterson et al. |
| 4,808,187 A | 2/1989 | Patterson et al. |
| 4,813,303 A | 3/1989 | Beezer et al. |
| 4,822,238 A | 4/1989 | Kwech |
| 4,955,918 A | 9/1990 | Lee |
| 4,960,425 A | 10/1990 | Yan et al. |
| 4,990,162 A | 2/1991 | LeBlanc et al. |
| 5,020,162 A | 6/1991 | Kersten et al. |
| 5,062,673 A | 11/1991 | Mimura |
| 5,088,125 A | 2/1992 | Ansell et al. |
| 5,133,775 A | 7/1992 | Chen |
| 5,246,463 A | 9/1993 | Giampapa |
| 5,252,102 A | 10/1993 | Singer et al. |
| 5,255,188 A | 10/1993 | Telepko |
| 5,387,245 A | 2/1995 | Fay et al. |
| 5,413,454 A | 5/1995 | Movsesian |
| 5,413,611 A | 5/1995 | Haslam, II et al. |
| 5,498,472 A | 3/1996 | Gold |
| 5,581,166 A | 12/1996 | Eismann et al. |
| 5,785,960 A | 7/1998 | Rigg et al. |
| 5,852,675 A | 12/1998 | Matsuo et al. |
| 5,888,213 A | 3/1999 | Sears et al. |
| 5,888,246 A | 3/1999 | Gow |
| 5,900,714 A | 5/1999 | Dubhashi et al. |
| 6,111,973 A | 8/2000 | Holt et al. |
| 6,175,962 B1 | 1/2001 | Michelson |
| 6,223,615 B1 | 5/2001 | Huck |
| 6,344,062 B1 | 2/2002 | Abboudi et al. |
| 6,361,570 B1 | 3/2002 | Gow |
| 6,660,043 B2 | 12/2003 | Kajitani et al. |
| 6,786,112 B2 | 9/2004 | Ruttor |
| 7,144,430 B2 | 12/2006 | Archer et al. |
| 7,243,569 B2 | 7/2007 | Takahashi et al. |
| 7,316,304 B2 | 1/2008 | Heravi et al. |
| 7,316,795 B1 | 1/2008 | Knauss |
| 7,370,896 B2 | 5/2008 | Anderson et al. |
| 7,823,475 B2 | 11/2010 | Hirabayashi et al. |
| 7,867,287 B2 | 1/2011 | Puchhammer |
| 7,922,773 B1 | 4/2011 | Kuiken |
| 8,016,893 B2 | 9/2011 | Weinberg et al. |
| 8,100,986 B2 | 1/2012 | Puchhammer et al. |
| 8,197,554 B2 | 6/2012 | Whiteley et al. |
| 8,257,446 B2 | 9/2012 | Puchhammer |
| 8,337,568 B2 | 12/2012 | Macduff |
| 8,491,666 B2 | 7/2013 | Schulz |
| 8,579,991 B2 | 11/2013 | Puchhammer |
| 8,593,255 B2 | 11/2013 | Pang et al. |
| 8,657,887 B2 | 2/2014 | Gill |
| 8,662,552 B2 | 3/2014 | Torres-Jara |
| 8,663,339 B2 | 3/2014 | Inschlag et al. |
| 8,690,963 B2 | 4/2014 | Puchhammer |
| 8,696,763 B2 | 4/2014 | Gill |
| 8,808,397 B2 | 8/2014 | Gow |
| 8,828,096 B2 | 9/2014 | Gill |
| 8,986,395 B2 | 3/2015 | McLeary |
| 8,995,760 B2 | 3/2015 | Gill |
| 9,278,012 B2 | 3/2016 | Gill |
| 9,387,095 B2 | 7/2016 | McLeary et al. |
| 9,402,749 B2 | 8/2016 | Gill et al. |
| 9,463,100 B2 | 10/2016 | Gill |
| 9,720,515 B2 * | 8/2017 | Wagner .................. G06F 3/017 |
| 9,839,534 B2 | 12/2017 | Lipsey et al. |
| 9,999,522 B2 | 6/2018 | Gill |
| 2001/0023058 A1 | 9/2001 | Jung et al. |
| 2002/0016631 A1 | 2/2002 | Marchitto et al. |
| 2002/0135241 A1 | 9/2002 | Kobayashi et al. |
| 2003/0036805 A1 | 2/2003 | Senior |
| 2004/0078091 A1 | 4/2004 | Elkins |
| 2004/0078299 A1 | 4/2004 | Down-Logan et al. |
| 2004/0181289 A1 | 9/2004 | Bedard et al. |
| 2005/0021154 A1 | 1/2005 | Brimalm |
| 2005/0021155 A1 | 1/2005 | Brimalm |
| 2005/0093997 A1 | 5/2005 | Dalton et al. |
| 2005/0101693 A1 | 5/2005 | Arbogast et al. |
| 2005/0192677 A1 | 9/2005 | Ragnarsdottir et al. |
| 2006/0029909 A1 | 2/2006 | Kaczkowski |
| 2006/0054782 A1 | 3/2006 | Olsen et al. |
| 2006/0158146 A1 | 7/2006 | Tadano |
| 2006/0167564 A1 | 7/2006 | Flaherty et al. |
| 2006/0212129 A1 | 9/2006 | Lake et al. |
| 2006/0229755 A1 | 10/2006 | Kuiken et al. |
| 2006/0251408 A1 | 11/2006 | Konno et al. |
| 2007/0058860 A1 | 3/2007 | Harville et al. |
| 2007/0061111 A1 | 3/2007 | Jung et al. |
| 2007/0071314 A1 | 3/2007 | Bhatti et al. |
| 2007/0230832 A1 | 10/2007 | Usui et al. |
| 2007/0260328 A1 | 11/2007 | Bertels et al. |
| 2008/0058668 A1 | 3/2008 | Seyed Momen et al. |
| 2008/0146981 A1 | 6/2008 | Greenwald et al. |
| 2008/0215162 A1 | 9/2008 | Farnsworth et al. |
| 2008/0260218 A1 | 10/2008 | Smith et al. |
| 2008/0262634 A1 | 10/2008 | Puchhammer |
| 2009/0213379 A1 | 8/2009 | Carroll et al. |
| 2010/0016990 A1 | 1/2010 | Kurtz |
| 2010/0116078 A1 | 5/2010 | Kim |
| 2010/0274365 A1 | 10/2010 | Evans et al. |
| 2011/0203027 A1 | 8/2011 | Flather et al. |
| 2011/0237381 A1 | 9/2011 | Puchhammer |
| 2011/0257765 A1 | 10/2011 | Evans et al. |
| 2011/0264238 A1 | 10/2011 | van der Merwe et al. |
| 2011/0265597 A1 | 11/2011 | Long |
| 2011/0278061 A1 | 11/2011 | Farnan |
| 2012/0004884 A1 | 1/2012 | Fillol et al. |
| 2012/0014571 A1 | 1/2012 | Wong et al. |
| 2012/0061155 A1 | 3/2012 | Berger et al. |
| 2012/0099788 A1 | 4/2012 | Bhatti et al. |
| 2012/0109337 A1 | 5/2012 | Schulz |
| 2012/0123558 A1 | 5/2012 | Gill |
| 2012/0204665 A1 | 8/2012 | Baudasse |
| 2012/0280812 A1 | 11/2012 | Sheikman et al. |
| 2012/0286629 A1 | 11/2012 | Johnson et al. |
| 2012/0303136 A1 | 11/2012 | Macduff |
| 2012/0330439 A1 | 12/2012 | Goldfarb et al. |
| 2013/0053984 A1 | 2/2013 | Hunter et al. |

(56) References Cited

U.S. PATENT DOCUMENTS

| | | |
|---|---|---|
| 2013/0076699 A1 | 3/2013 | Spencer |
| 2013/0253705 A1 | 9/2013 | Goldfarb et al. |
| 2013/0268094 A1 | 10/2013 | Van Wiemeersch |
| 2014/0236314 A1 | 8/2014 | Van Wiemeersch |
| 2014/0324189 A1 | 10/2014 | Gill et al. |
| 2014/0371871 A1* | 12/2014 | Farina ............... B25J 9/161 623/24 |
| 2015/0142082 A1 | 5/2015 | Simon et al. |
| 2015/0216681 A1 | 8/2015 | Lipsey et al. |
| 2015/0230941 A1 | 8/2015 | Jury |
| 2015/0351935 A1* | 12/2015 | Donati ............... A61F 2/586 623/25 |
| 2015/0374515 A1 | 12/2015 | Meijer et al. |
| 2016/0287422 A1* | 10/2016 | Kelly ............... A61F 5/013 |
| 2017/0007424 A1 | 1/2017 | Gill |
| 2017/0049586 A1 | 2/2017 | Gill et al. |
| 2017/0281368 A1 | 10/2017 | Gill |
| 2018/0071115 A1 | 3/2018 | Lipsey et al. |
| 2018/0296368 A1 | 10/2018 | Gill |

FOREIGN PATENT DOCUMENTS

| | | |
|---|---|---|
| DE | 24 34 834 | 2/1976 |
| DE | 198 54 762 | 6/2000 |
| DE | 101 05 814 | 9/2002 |
| DE | 203 15 575 | 1/2004 |
| DE | 10 2012 009 699 | 11/2013 |
| EP | 0 145 504 | 6/1985 |
| EP | 0 219 478 | 4/1987 |
| EP | 0 256 643 | 2/1988 |
| EP | 0 484 173 | 5/1992 |
| EP | 0 947 899 | 10/1999 |
| EP | 0 968 695 | 1/2000 |
| EP | 1 043 003 | 10/2000 |
| EP | 1 617 103 | 1/2006 |
| EP | 2 532 927 | 12/2012 |
| EP | 2 612 619 | 7/2013 |
| GB | 326 970 | 3/1930 |
| GB | 607 001 | 2/1947 |
| GB | 1 386 942 | 3/1975 |
| GB | 1 510 298 | 5/1978 |
| GB | 1 585 256 | 2/1981 |
| GB | 2 067 074 | 7/1981 |
| GB | 2 146 406 | 4/1985 |
| GB | 2 357 725 A | 7/2001 |
| GB | 2 444 679 | 6/2008 |
| JP | 53-011456 | 2/1978 |
| JP | 53-094693 | 8/1978 |
| JP | 07-174631 | 7/1995 |
| JP | 2001-082913 | 3/2001 |
| JP | 2001-299448 | 10/2001 |
| JP | 2002-131135 | 5/2002 |
| JP | 2002-310242 | 10/2002 |
| JP | 2003-134526 | 5/2003 |
| JP | 2004-073802 | 3/2004 |
| JP | 2004-224280 | 8/2004 |
| WO | WO 95/024875 | 9/1995 |
| WO | WO 96/023643 | 8/1996 |
| WO | WO 00/025840 | 5/2000 |
| WO | WO 00/069375 | 11/2000 |
| WO | WO 01/004838 | 1/2001 |
| WO | WO 02/049534 | 6/2002 |
| WO | WO 03/017877 | 3/2003 |
| WO | WO 03/017878 | 3/2003 |
| WO | WO 03/017880 | 3/2003 |
| WO | WO 2006/058190 | 6/2006 |
| WO | WO 2006/069264 | 6/2006 |
| WO | WO 2006/078432 | 7/2006 |
| WO | WO 2006/086504 | 8/2006 |
| WO | WO 2006/092604 | 9/2006 |
| WO | WO 2006/110790 | 10/2006 |
| WO | WO 2007/063266 | 6/2007 |
| WO | WO 2007/076764 | 7/2007 |
| WO | WO 2007/076765 | 7/2007 |
| WO | WO 2007/126854 | 11/2007 |
| WO | WO 2007/127973 | 11/2007 |
| WO | WO 2008/044052 | 4/2008 |
| WO | WO 2008/044207 | 4/2008 |
| WO | WO 2008/092695 | 8/2008 |
| WO | WO 2008/098059 | 8/2008 |
| WO | WO 2008/098072 | 8/2008 |
| WO | WO 2009/011682 | 1/2009 |
| WO | WO 2010/018358 | 2/2010 |
| WO | WO 2010/051798 | 5/2010 |
| WO | WO 2010/149967 | 12/2010 |
| WO | WO 2011/001136 | 1/2011 |
| WO | WO 2011/022569 | 2/2011 |
| WO | WO 2011/036473 | 3/2011 |
| WO | WO 2011/036626 | 3/2011 |
| WO | WO 2011/088964 | 7/2011 |
| WO | WO 2011/107778 | 9/2011 |
| WO | WO 2011/143004 | 11/2011 |
| WO | WO 2015/120076 | 8/2015 |
| WO | WO 2015/120083 | 8/2015 |
| WO | WO 2016/051138 | 4/2016 |

OTHER PUBLICATIONS

Connolly, "Prosthetic Hands from Touch Bionics", Industrial Robot, Emerald Group Publishing Limited, 2008, vol. 35, No. 4, pp. 290-293.

International Search Report and Written Opinion in Application No. PCT/IB2016/001713, dated Jul. 12, 2017.

Mace et al., "Augmenting Neuroprosthetic Hanf Control Through Evaluation of a Bioacoustic Interface", IEEE/RSJ International Conference on Intelligent Robots and Systems (IROS), Tokyo, Japan, Nov. 3-7, 2013, pp. 7.

Martinez-Villalpando et al., "Agonist-Antagonist Active Knee Prosthesis: A Preliminary Study in Level-Ground Walking", Journal of Rehabilitation Research & Development, vol. 46, No. 3, 2009, pp. 361-374.

Osborn et al., "Utilizing Tactile Feedback for Biomimetic Grasping Control in Upper Limb Prostheses". Department of Biomedical Engineering, Johns Hopkins University, Baltimore, USA, 2013, pp. 4.

Pedrocchi et al., "MUNDUS Project: Multimodal Neuroprosthesis for Daily Upper Limb Support", Journal of Neuroengineering and Rehabilitation, 2013, vol. 10, No. 66, pp. 20. http://www.jneuroengrehab.com/content/10/1/66.

Press Release, "Touch Bionics Introduce Digitally Controlled Supro Wrist", http://www.touchbionics.com/news-events/news/touch-bionics-introduce-digitally-controlled-supro-wrist, May 3, 2016 in 2 pages.

Stix, Gary, "Phantom Touch: Imbuing a Prosthesis with Manual Dexterity", Scientific American, Oct. 1998, pp. 41 & 44.

Trachtenberg et al., "Radio Frequency Identification, an Innovative Solution to Guide Dexterous Prosthetic Hands", 33rd Annual International Conference of the IEEE EMBS, Boston, MA, Aug. 30-Sep. 3, 2011, pp. 4.

Antonio et al., "A Virtual Upper Limb Prosthesis as a Training System", 7th International Conference on Electrical Engineering, Computing Science and Automatic Control (CCE 2010) Tuxtla Gutiérrez, Chiapas, Mexico. Sep. 8-10, 2010, pp. 210-215.

"DC Circuit Theory", https://www.electronics-tutorials.ws/dccircuits/dcp_1.html, Date verified by the Wayback Machine Apr. 23, 2013, pp. 16.

Fukuda et al., "Training of Grasping Motion Using a Virtual Prosthetic Control System", 2010 IEEE International Conference on Systems Man and Cybernetics (SMC), Oct. 10-13, 2010, pp. 1793-1798.

Grip Chips™, Datasheet, May 15, 2014, Issue 1, http://touchbionics.com/sites/default/files/files/Grip%20Chip%20datasheet%20May%202014.pdf, pp. 1.

Lamounier et al., "On the Use of Virtual and Augmented Reality for Upper Limb Prostheses Training and Simulation", 2010 Annual International Conference of the IEEE Engineering in Medicine and Biology Society (EMBC), Aug. 31-Sep. 4, 2010, pp. 2451-2454.

(56) References Cited

OTHER PUBLICATIONS

"Touch Bionics Grip Chips Let Hand Prostheses Think for Themselves", May 15, 2014, www.medgadget.com/2014/05/touch-bionics-grip-chips-let-hand-prostheses-think-for-themselves.html, pp. 2.

Vilarino, Martin, "A Novel Wireless Controller for Switching among Modes for an Upper-Limb Prosthesis", The Academy TODAY, Jan. 2014, vol. 10, No. 1, pp. A-12 to A-15.

"Supro Wrist", Touch Bionics, https://web.archive.org/web/20160928141440/http://www.touchbionics.com/products/supro-wrist, as archived Sep. 28, 2016 in 3 pages.

Albu-Schaffer et al., "Soft Robotics", IEEE Robotics & Automation Magazine, Sep. 2008, vol. 15, No. 3, pp. 20-30.

Bellman et al., "SPARKy 3: Design of an Active Robotic Ankle Prosthesis with Two Actuated Degrees of Freedom Using Regenerative Kinetics", in Proceedings of the 2nd Biennial IEEE/RAS-EMBS International Conference on Biomedical Robotics and Biomechatronics, Oct. 19-22, 2008, Scottsdale, AZ, pp. 511-516.

Belter et al., "Mechanical Design and Performance Specifications of Anthropomorphic Prosthetic Hands: A Review", JRRD, Jan. 2013, vol. 50, No. 5, pp. 599-618.

Biddiss et al., "Consumer Design Priorities for Upper Limb Prosthetics", Disability and Rehabilitation: Assistive Technology, Nov. 2007, vol. 2, No. 6, pp. 346-357.

Biddiss et al., "Upper Limb Prosthesis Use and Abandonment: A Survey of the Last 25 Years", Prosthetics and Orthotics International, Sep. 2007, vol. 31, No. 3, pp. 236-257.

Biddiss et al., "Upper-Limb Prosthetics: Critical Factors in Device Abandonment", American Journal of Physical Medicine & Rehabilitation, Dec. 2007, vol. 86, No. 12, pp. 977-987.

Chicoine et al., "Prosthesis-Guided Training of Pattern Recognition-Controlled Myoelectric Prosthesis", in Proceedings of the 34th Annual International Conference of the IEEE EMBS, San Diego, CA, Aug. 28-Sep. 1, 2012, pp. 1876-1879.

Childress et al., "Control of Limb Prostheses", American Academy of Orthopaedic Surgeons, Chapter 12, pp. 173-195, 2004.

Choi et al., "Design of High Power Permanent Magnet Motor with Segment Rectangular Copper Wire and Closed Slot Opening on Electric Vehicles", IEEE Transactions on Magnetics, Jun. 2010, vol. 46, No. 9, pp. 2070-2073.

Cipriani et al., "On the Shared Control of an EMG-Controlled Prosthetic Hand: Analysis of User-Prosthesis Interaction", IEEE Transactions on Robotics, Feb. 2008, vol. 24, No. 1, pp. 170-184.

Controzzi et al., "Miniaturized Non-Back-Drivable Mechanism for Robotic Applications", Mechanism and Machine Theory, Oct. 2010, vol. 45, No. 10, pp. 1395-1406.

Damian et al., "Artificial Tactile Sensing of Position and Slip Speed by Exploiting Geometrical Features", IEEE/ASME Transactions on Mechatronics, Feb. 2015, vol. 20, No. 1, pp. 263-274.

Dechev et al., "Multiple Finger, Passive Adaptive Grasp Prosthetic Hand", Mechanism and Machine Theory, Oct. 1, 2001, vol. 36, No. 10, pp. 1157-1173.

Dellorto, Danielle, "Bionic Hands Controlled by iPhone App", CNN, Apr. 12, 2013, pp. 4 http://www.cnn.com/2013/04/12/health/bionic-hands.

"DuPont Engineering Design—The Review of DuPont Engineering Polymers in Action", http://www.engpolymer.co.kr/x_data/magazine/engdesign07_2e.pdf, Feb. 2007, pp. 16.

Engeberg et al., "Adaptive Sliding Mode Control for Prosthetic Hands to Simultaneously Prevent Slip and Minimize Deformation of Grasped Objects," IEEE/ASME Transactions on Mechatronics, Feb. 2013, vol. 18, No. 1, pp. 376-385.

Fougner et al., "Control of Upper Limb Prostheses: Terminology and Proportional Myoelectric Control—A Review", IEEE Transactions on Neural Systems Rehabilitation Engineering, Sep. 2012, vol. 20, No. 5, pp. 663-677.

Gaine et al., "Upper Limb Traumatic Amputees. Review of Prosthetic Use", The Journal of Hand Surgery, Feb. 1997, vol. 22B, No. 1, pp. 73-76.

Heckathorne, Craig W., "Components for Electric-Powered Systems", American Academy of Orthopaedic Surgeons, Chapter 11, pp. 145-171, 2004.

Hojjat et al., "A Comprehensive Study on Capabilities and Limitations of Roller-Screw with Emphasis on Slip Tendency", Mechanism and Machine Theory, 2009, vol. 44, No. 10, pp. 1887-1899.

Hsieh, Chiu-Fan., "Dynamics Analysis of Cycloidal Speed Reducers with Pinwheel and Nonpinwheel Designs", ASME Journal of Mechanical Design, Sep. 2014, vol. 136, No. 9, pp. 091008-1-09100811.

Jebsen et al., "An Objective and Standardized Test of Hand Function", Arch. Phys. Med. Rehabil., 1969, vol. 50, No. 6, pp. 311-319.

Johannes et al., "An Overview of the Developmental Process for the Modular Prosthetic Limb," John Hopkins APL Technical Digest, 2011, vol. 30, No. 3, pp. 207-216.

Kent et al., "Electromyogram Synergy Control of a Dexterous Artificial Hand to Unscrew and Screw Objects", Journal of Neuroengineering and Rehabilitation, 2014, vol. 11, No. 1, pp. 1-20.

Kermani et al., "Friction Identification and Compensation in Robotic Manipulators", IEEE Transactions on Instrumentation and Measurement, Dec. 2007, vol. 56, No. 6, pp. 2346-2353.

Kuiken et al., "Targeted Muscle Reinnervation for Real-Time Myoelectric Control of Multifunction Artificial Arms", JAMA, Feb. 11, 2009, vol. 301, No. 6, pp. 619-628.

Light et al., "Establishing a Standardized Clinical Assessment Tool of Pathologic and Prosthetic Hand Function: Normative Data, Reliability, and Validity", Arch. Phys. Med. Rehabil., 2002, vol. 83, pp. 776-783.

Majd et al., "A Continuous Friction Model for Servo Systems with Stiction", in Proceedings of the IEEE Conference on Control Applications, 1995, pp. 296-301.

Maxon Precision Motors, Inc., "Maxon Flat Motor: EX 10 flat 10 mm, brushless, 0.25 Watt", Specification, May 2011, p. 181.

Maxon Precision Motors, Inc., "Maxon EX Motor: EC10 10 mm, brushless, 8 Watt", Specification, May 2011, p. 140.

Miller et al., "Summary and Recommendations of the Academy's State of the Science Conference on Upper Limb Prosthetic Outcome Measures", Journal of Prosthetics Orthotics, 2009, vol. 21, pp. 83-89.

Montagnani et al., "Is it Finger or Wrist Dexterity that is Missing in Current Hand Prostheses?", IEEE Transactions on Neural Systems and Rehabilitation Engineering, Jul. 2015, vol. 23, No. 4, pp. 600-609.

Morita et al., "Development of 4-D.O.F. Manipulator Using Mechanical Impedance Adjuster", Proceedings of the 1996 IEEE International Conference on Robotics and Automation, Minneapolis, MN, Apr. 1996, pp. 2902-2907.

Ninu et al., "Closed-Loop Control of Grasping with a Myoelectric Hand Prosthesis: Which are the Relevant Feedback Variable for Force Control?" IEEE Transactions on Neural Systems and Rehabilitation Engineering, Sep. 2014, vol. 22, No. 5, pp. 1041-1052.

Pinzur et al., "Functional Outcome Following Traumatic Upper Limb Amputation and Prosthetic Limb Fitting", J. Hand Surgery, Amer. vol. 1994. vol. 19, pp. 836-839.

Raspopovic et al., "Restoring Natural Sensory Feedback in Real-Time Bidirectional Hand Prostheses", Science Translational Medicine, Feb. 5, 2014, vol. 6, No. 222, pp. 1-10.

Resnik et al., "The DEKA Arm: Its Features, Functionality, and Evolution During the Veterans Affairs Study to Optimize the DEKA Arm", Prosthetics and Orthotics International, 2014, vol. 38, No. 6, pp. 492-504.

Scheme et al., "Electromyogram Pattern Recognition for Control of Powered Upper-Limb Prostheses: State of the Art and Challenges for Clinical Use", Journal of Rehabilitation Research & Development (JRRD), 2011, vol. 48, No. 6, pp. 643-659.

Scheme et al., "Motion Normalized Proportional Control for Improved Pattern Recognition-Based Myoelectric Control", IEEE Transactions on Neural Systems and Rehabilitation Engineering, Jan. 2014, vol. 22, No. 1, pp. 149-157.

Sensinger et al., "Cycloid vs. Harmonic Drives for use in High Ratio, Single Stage Robotic Transmissions", presented at the IEEE Conference on Robotics and Automation, Saint Paul, MN, USA, May 14-18, 2012, pp. 4130-4135.

(56) References Cited

OTHER PUBLICATIONS

Sensinger, "Efficiency of High-Sensitivity Gear Trains, such as Cycloid Drives", J. Mech. Des., 2013, vol. 135, No. 7, p. 71006.
Sensinger et al., "Exterior vs. Interior Rotors in Robotic Brushless Motors", 2011 IEEE International Conference on Robotics and Automation (ICRA), IEEE, May 9-13, 2011, pp. 2764-2770.
Sensinger, "Selecting Motors for Robots Using Biomimetic Trajectories:Optimum Benchmarks, Windings, and other Considerations," in Proc. IEEE Conf. Robot. Autom., Anchorage, AL, USA, 2010, pp. 4175-4181.
Sensinger, "Unified Approach to Cycloid Drive Profile, Stress, and Efficiency Optimization", Journal of Mechanical Design, Feb. 2010, vol. 132, pp. 024503-1-024503-5.
Sensinger et al., "User-Modulated Impedance Control of a Prosthetic Elbow in Unconstrained, Perturbed Motion", IEEE Trans. Biomed. Eng., Mar. 2008, vol. 55, No. 3, pp. 1043-1055.
Sutton et al., "Towards a Universal Coupler Design for Modern Powered Prostheses", Presented at the Myoelect. Controls Symp., Fredericton, NB, Canada, 2011.
Tan et al., "A Neural Interface Provides Long-Term Stable Natural Touch Perception", Science Translational Medicine, Oct. 8, 2014, vol. 6, No. 257, pp. 1-11.
Tang, "General Concepts of Wrist Biomechanics and a View from Other Species", J. Hand Surg., Eur. Vol., Aug. 2008, vol. 33, No. 4, pp. 519-525.
Toledo et al., "A Comparison of Direct and Pattern Recognition Control for a Two Degree-of-Freedom Above Elbow Virtual Prosthesis", in Proceedings 34th Annual International Conference of the IEEE EMBS, 2012, pp. 4332-4335.
Weir et al., "Design of Artificial Arms and Hands for Prosthetic Applications", Biomedical Engineering and Design Handbook, 2009, vol. 2, M. Kutz, Ed., 2nd Ed. New York, NY, USA: McGraw-Hill, pp. 537-598.
Wettels et al., "Grip Control Using Biomimetic Tactile Sensing Systems", IEEE/ASME Transactions on Mechatronics, Dec. 2009, vol. 14, No. 6, pp. 718-723.
Whiteside et al., "Practice Analysis Task Force: Practice Analysis of the Disciplines of Orthotics and Prosthetics", American Board for Certification in Orthotics and Prosthetics, Inc., 2000, pp. 1-51.
Wilson et al., "A Bus-Based Smart Myoelectric Electrode/Amplifier-System Requirements", IEEE Transactions on Instrumentation and Measurement, Oct. 2011, vol. 60, No. 10, pp. 3290-3299.
Zampagni et al., "A Protocol for Clinical Evaluation of the Carrying Angle of the Elbow by Anatomic Landmarks", Journal of Shoulder and Elbow Surgery, 2008, vol. 17, No. 1, pp. 106-112.

\* cited by examiner

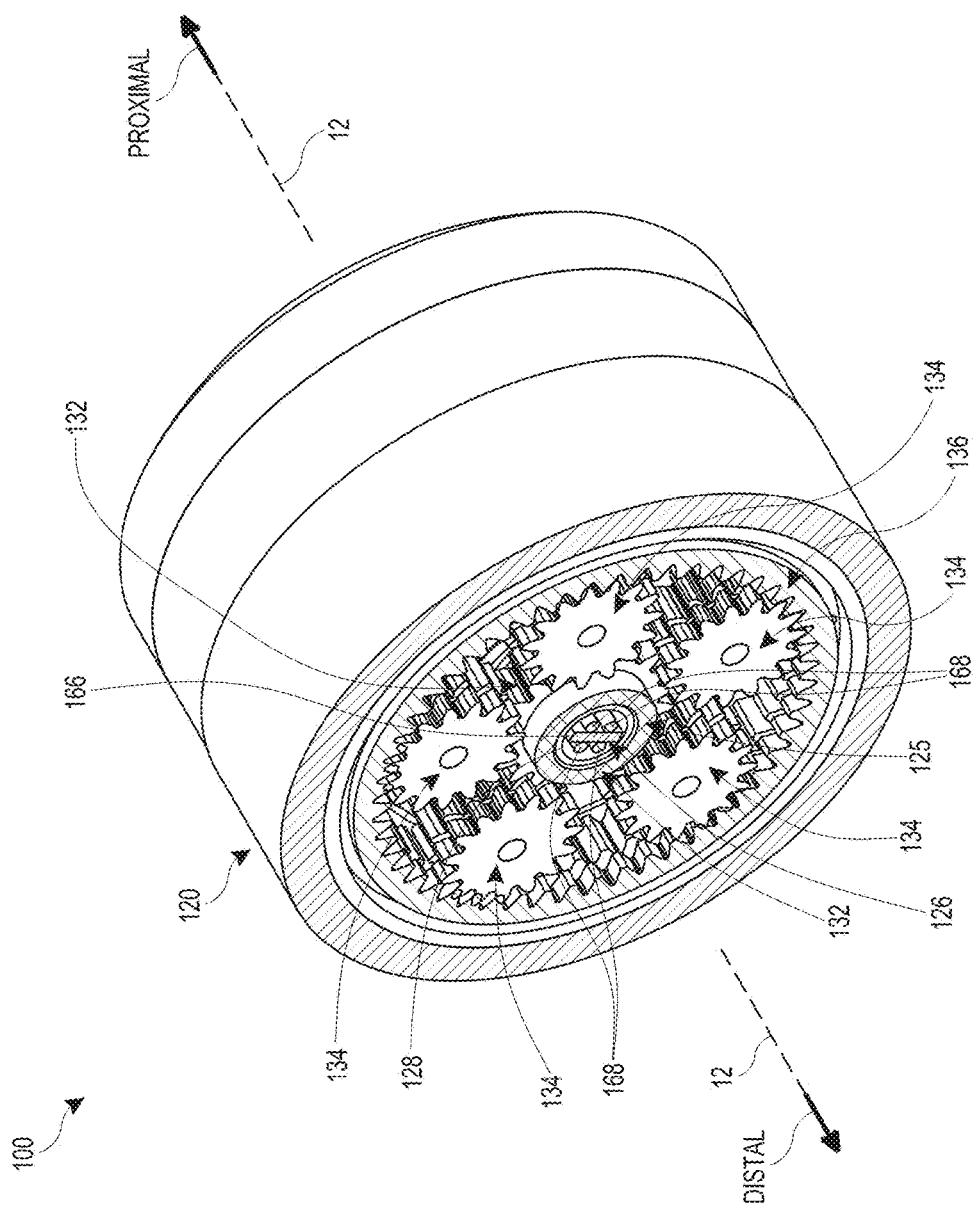

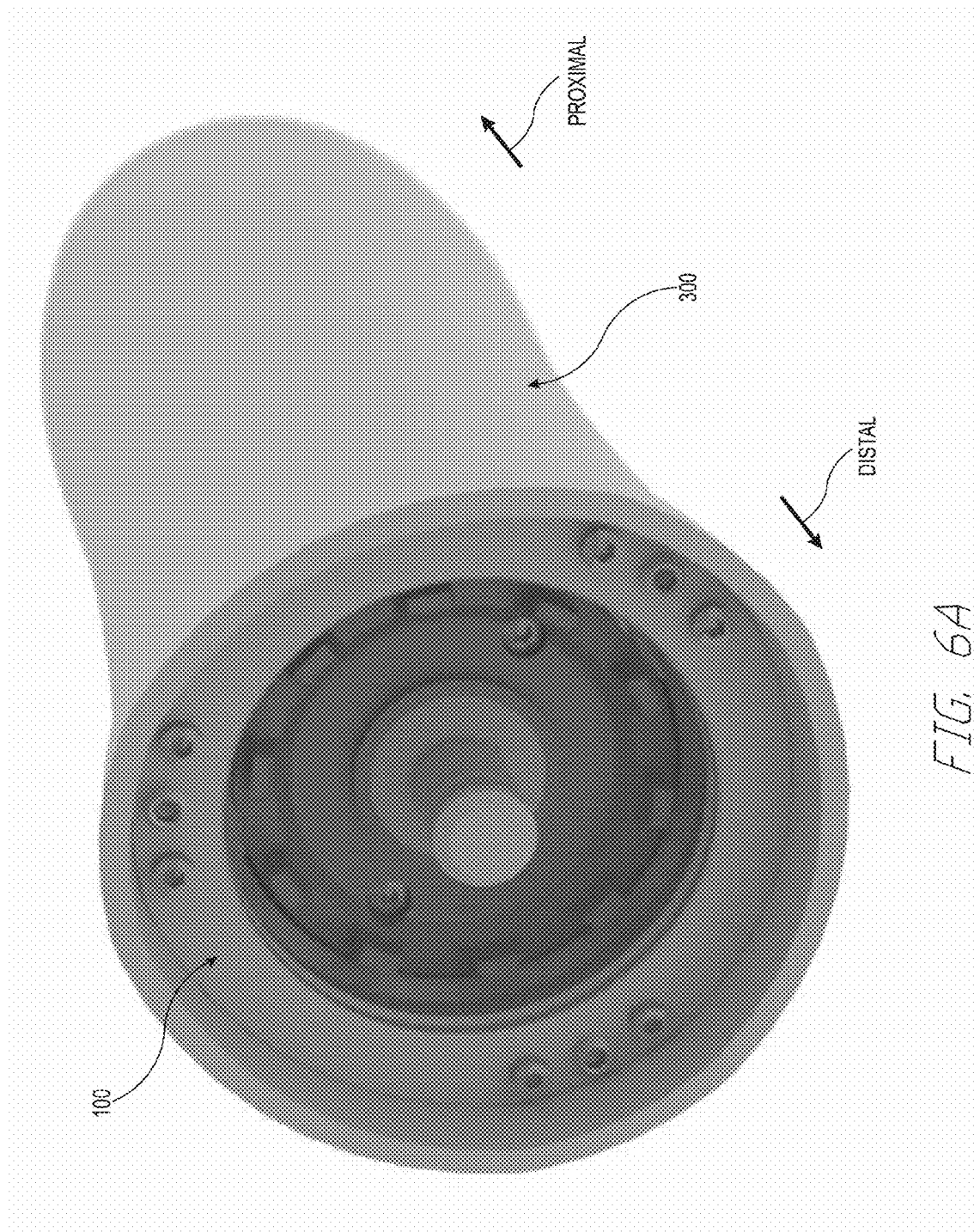

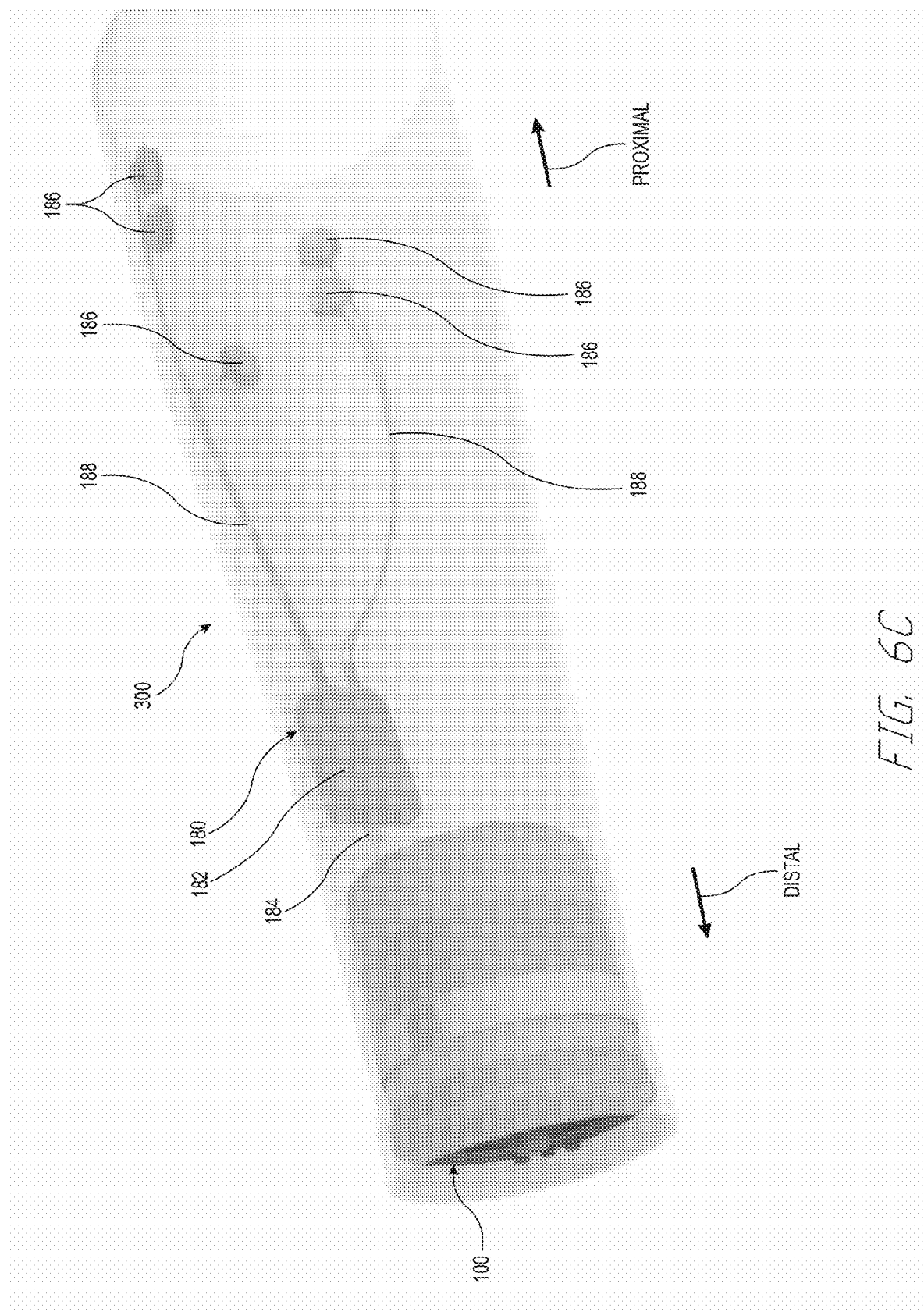

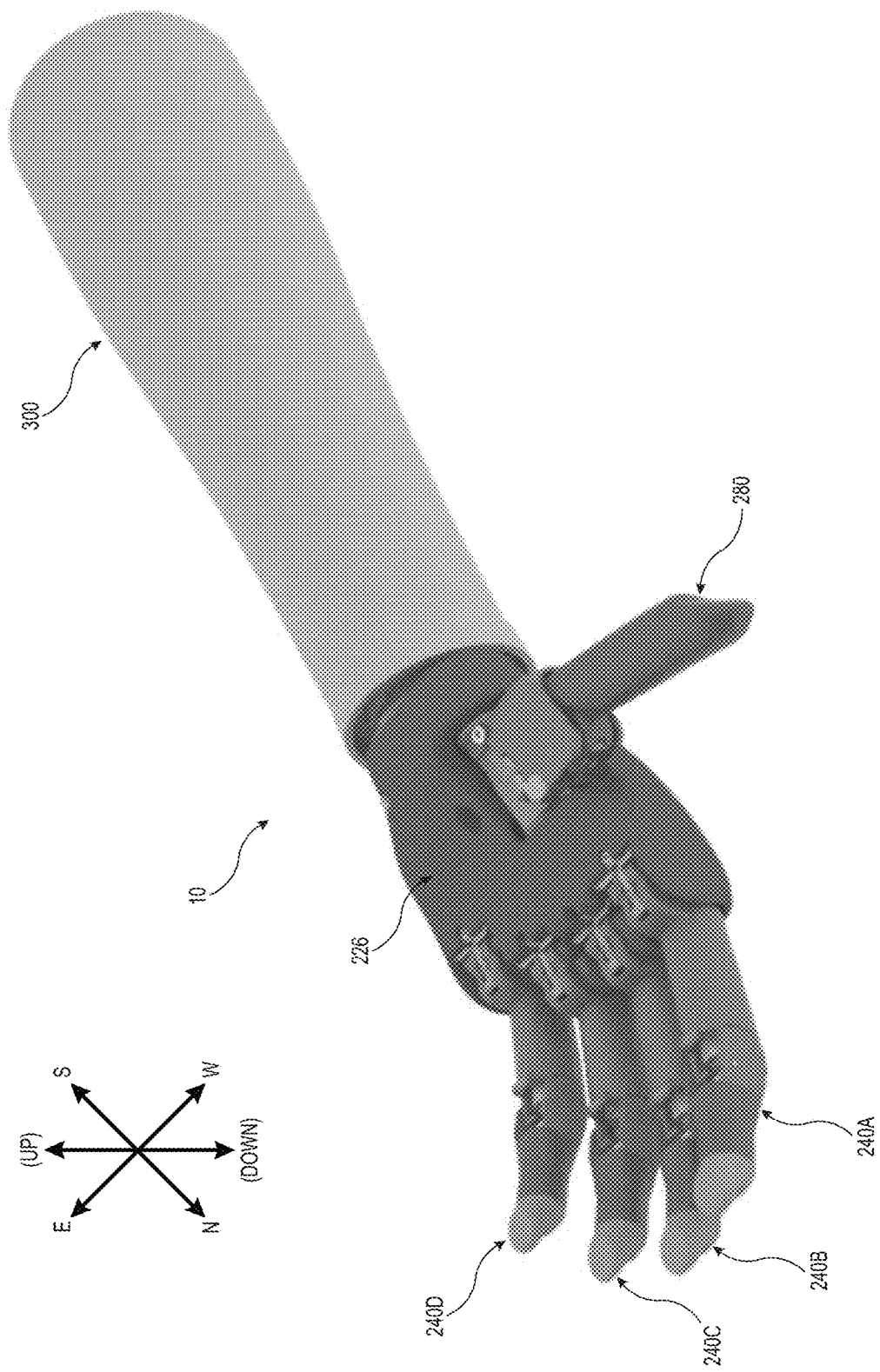

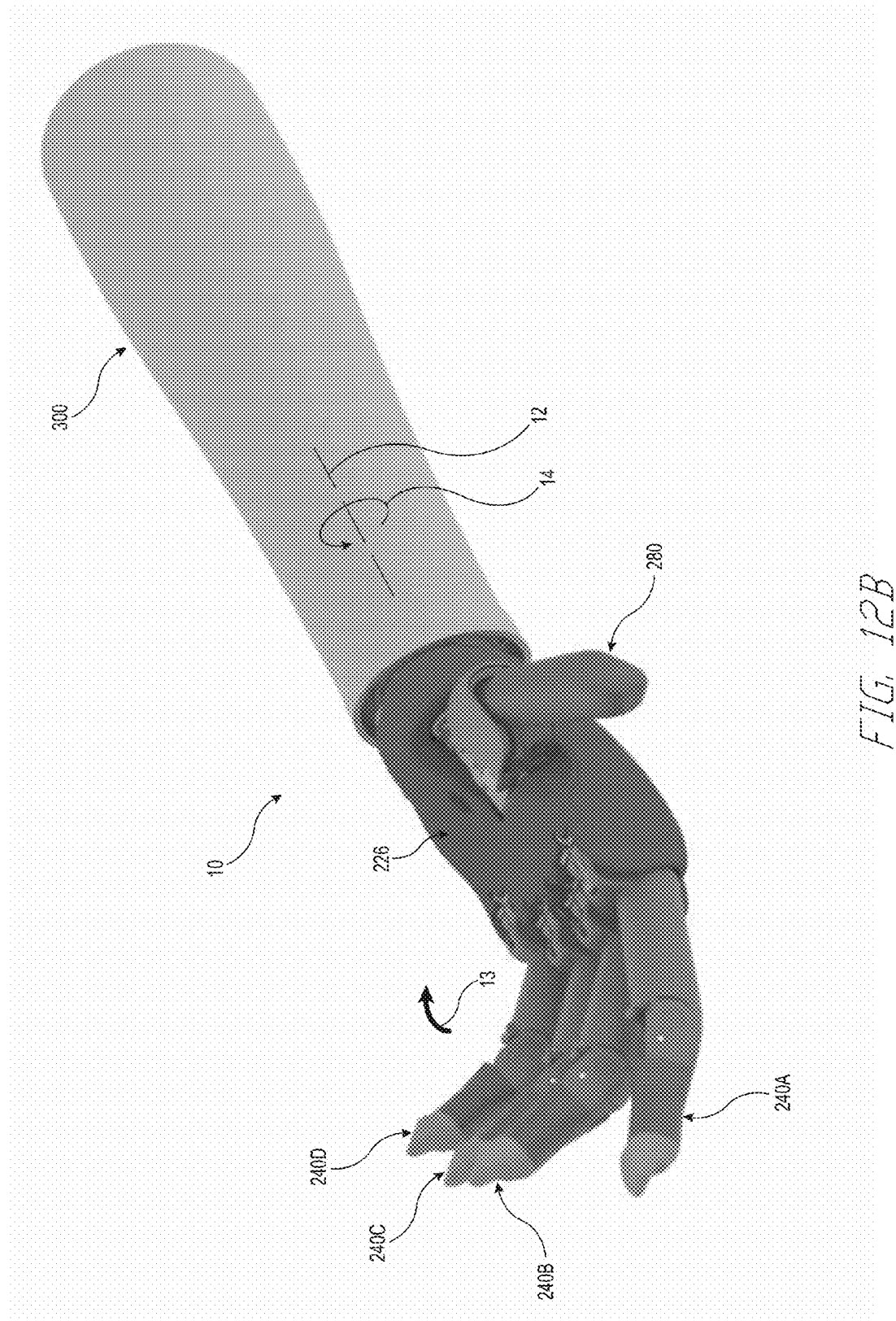

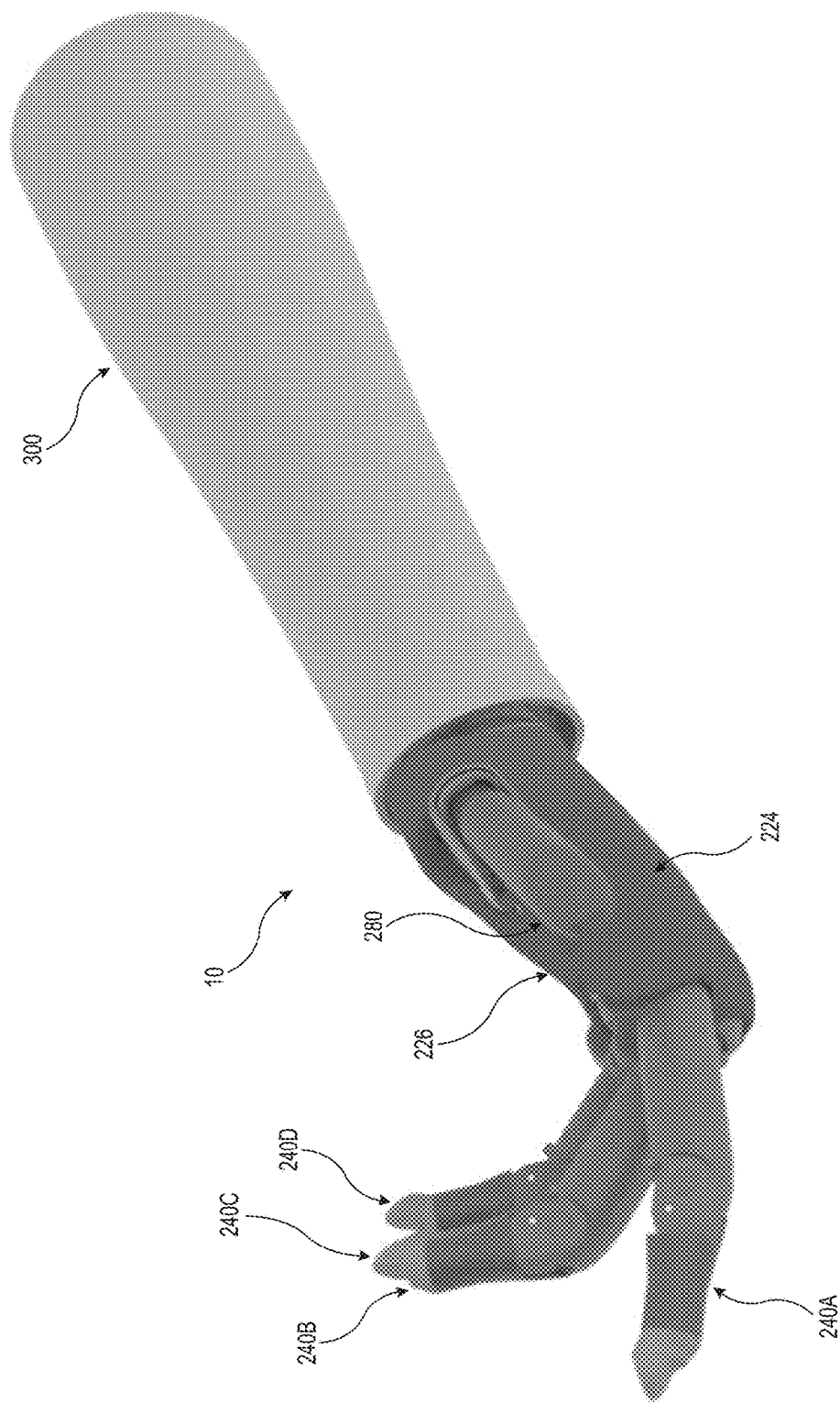

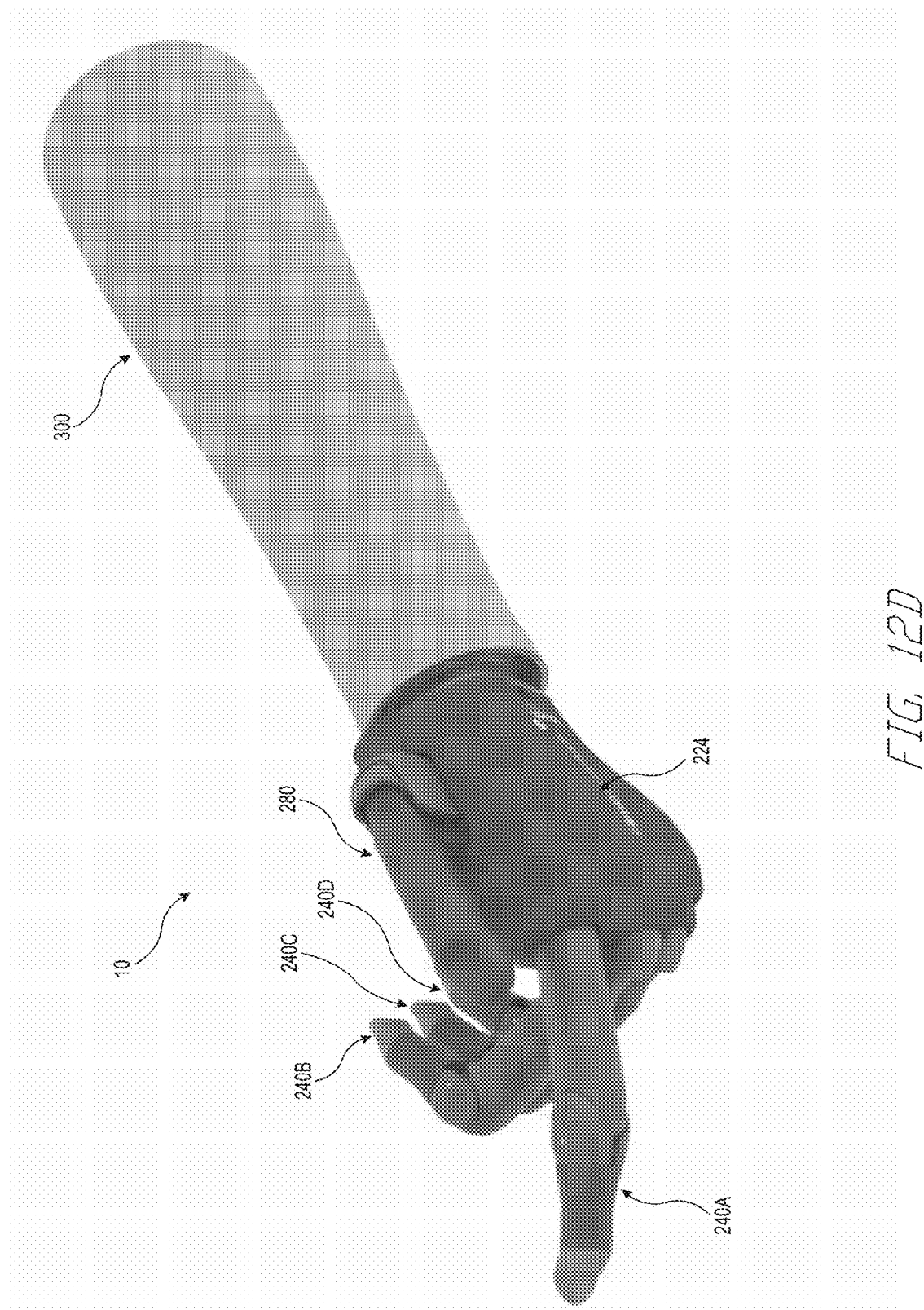

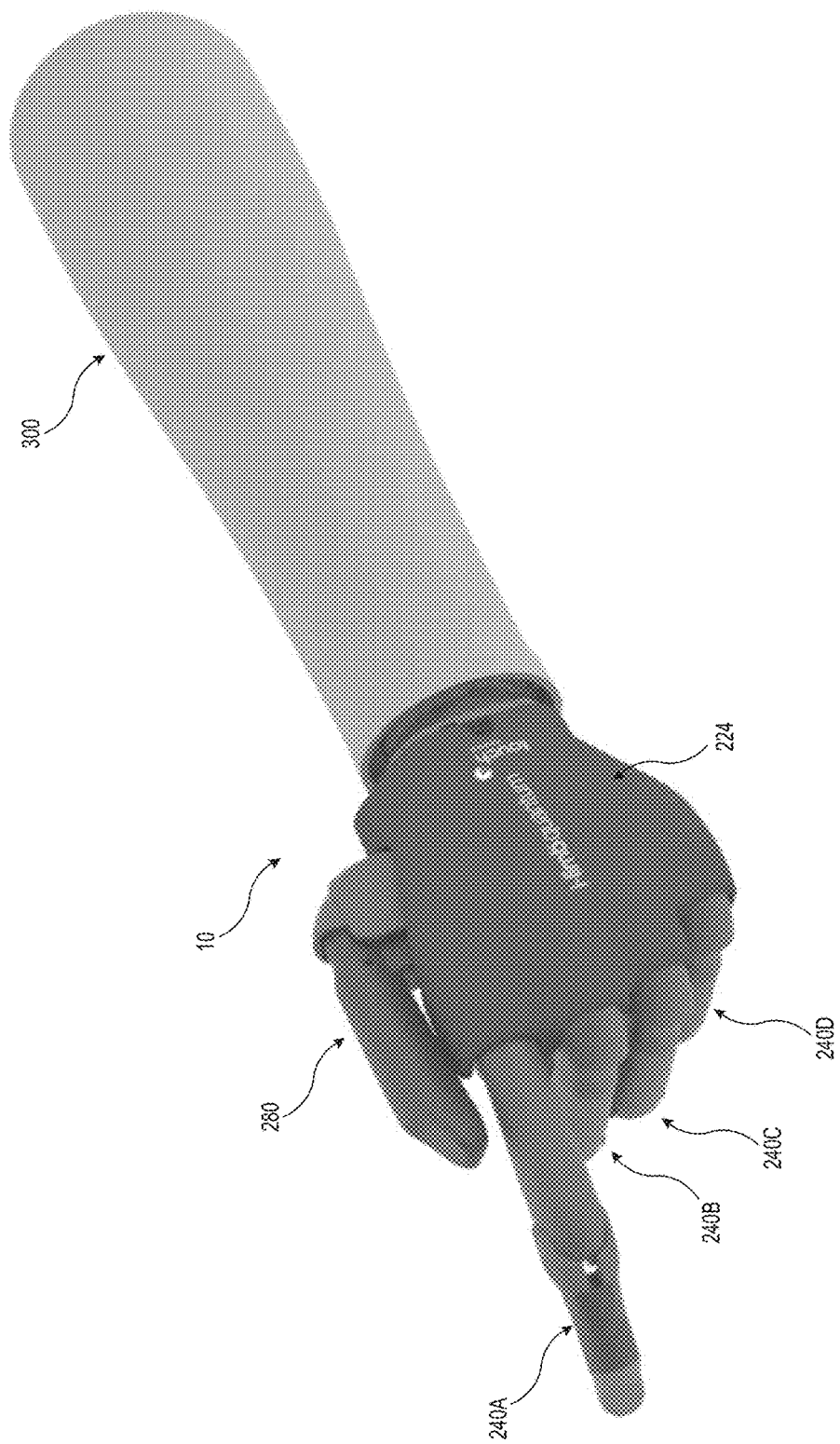

SYSTEMS AND METHODS FOR PROSTHETIC WRIST ROTATION

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

This application claims the benefit of U.S. Provisional Patent Application No. 62/382,919, filed Sep. 2, 2016, entitled SYSTEMS AND METHODS FOR PROSTHETIC WRIST ROTATION, the disclosure of which is incorporated herein by reference in its entirety for all purposes.

BACKGROUND

Field

Described herein are features related to prosthetics, for example a prosthetic hand and wrist system and associated methods.

Description of the Related Art

Hand and arm amputees benefit greatly from prosthetic replacements. Prosthetic hands, wrists, and/or arms restore lost functionality and provide independence to users. However, existing solutions have deficient wrist control. For instance, existing solutions cause responsive delay with wrist rotation that detracts from more closely mimicking the functionality of a natural wrist. As another example, existing solutions insufficiently synchronize wrist movement with other prosthetic movements, such as grip formation with a prosthetic hand and/or rotation of a prosthetic arm, which detracts from more closely mimicking the functionality of a natural limb. Improved prosthetic wrist solutions without these and other drawbacks are therefore desirable.

SUMMARY

The embodiments disclosed herein each have several aspects no single one of which is solely responsible for the disclosure's desirable attributes. Without limiting the scope of this disclosure, its more prominent features will now be briefly discussed. After considering this discussion, and particularly after reading the section entitled "Detailed Description," one will understand how the features of the embodiments described herein provide advantages over existing systems, devices and methods.

The following disclosure describes non-limiting examples of some embodiments. For instance, other embodiments of the disclosed systems and methods may or may not include the features described herein. Moreover, disclosed advantages and benefits can apply only to certain embodiments of the invention and should not be used to limit the disclosure.

Prosthetic hand and wrist systems and methods described herein provide a more responsive upper limb prosthetic system for amputees. In some embodiments, the rotation of a prosthetic wrist is performed in conjunction with the formation of a grip with a corresponding prosthetic hand. Users can command a particular grip to be formed with the prosthetic hand, and the prosthetic wrist will rotate responsively and in an efficient manner to simulate natural hand and wrist movement.

In one aspect, a prosthetic hand and wrist system is described. The prosthetic hand and wrist system comprises a prosthetic hand, a prosthetic wrist, and an inertial measurement unit (IMU) attached to the prosthetic hand. The prosthetic wrist comprises a fixed portion, an actuator, and a rotatable portion. The fixed portion is configured to attach to an arm, the rotatable portion is configured to attach to the prosthetic hand, and the actuator is attached to both the fixed and rotatable portions and is configured to actuate the rotatable portion relative to the fixed portion thereby rotating the prosthetic hand. The IMU is configured to detect an orientation of the prosthetic hand. A processor in communication with the IMU and the actuator is configured to execute a set of instructions to perform a method to control the actuator. The set of instructions may be stored in a memory located on the prosthetic hand, the prosthetic wrist or remotely. The method executed by the set of instructions comprises receiving data from the IMU associated with the orientation of the prosthetic hand, identifying a desired grip for the prosthetic hand, determining a rotation for the prosthetic hand based on i) the data from the IMU and ii) the desired grip, and causing the actuator to perform the rotation for the prosthetic hand by actuating the rotatable portion.

In some embodiments, identifying the desired grip for the prosthetic hand comprises receiving an electromyography (EMG) signal from a user of the prosthetic hand and wrist system, detecting a gesture movement performed by the user, and determining the desired grip based on the detected gesture movement. In some embodiments, identifying the desired grip for the prosthetic hand further comprises prompting the user to perform the gesture movement. In some embodiments, prompting the user to perform the gesture movement comprises moving a finger of the prosthetic hand.

In some embodiments, determining the rotation for the prosthetic hand comprises determining Euler angles for the prosthetic hand based on the data from the IMU, and determining angular rotation data based on the determined Euler angles and on the desired grip. The angular rotation data may comprise a direction and an angle of rotation. The angular rotation data may comprise a speed of rotation.

In some embodiments, the prosthetic hand and wrist system further comprises an actuator coupled with the prosthetic hand and configured to actuate to form the desired grip with the prosthetic hand. In some embodiments, the actuation of the prosthetic hand to the desired grip and the rotation of the prosthetic hand are performed simultaneously. In some embodiments, the prosthetic hand and wrist system comprises a plurality of digit actuators coupled with a plurality of digits of the prosthetic hand, and the plurality of digit actuators are configured to actuate to form the desired grip with the prosthetic hand. In some embodiments, the prosthetic hand and wrist system further comprises a distal actuator coupled with a distal portion of the hand, and the distal actuator is configured to rotate the hand about a pitch axis to form the desired grip with the prosthetic hand.

In some embodiments, the actuator is configured to cause rotation of the prosthetic hand about a single axis, such as a roll axis. The actuator may be configured to cause rotation of the prosthetic hand about two or more axes. The actuator may be configured to cause rotation of the prosthetic hand about a pitch axis and a roll axis.

In some embodiments, the IMU comprises a nine-axis IMU including three accelerometers, three gyroscopes and three magnetometers.

In some embodiments, the arm is a natural arm. In some embodiments, the arm is a prosthetic arm. The prosthetic arm may be actuatable and include an elbow joint and/or a shoulder joint. The actuatable prosthetic arm may be controlled in conjunction with rotation of the prosthetic wrist and formation of a grip with the prosthetic hand. An elbow joint and/or a shoulder joint may be controllably actuated, for example rotated. In some embodiments, a prosthetic system includes the rotatable prosthetic wrist, the prosthetic hand configured to form a grip, a prosthetic arm having an actuatable elbow joint and/or shoulder joint. Additional IMUs may be included in the additional prosthetic components, for example with the actuatable arm to detect and measure orientations of one or more segments of the prosthetic arm, such as rotation about the elbow and/or shoulder. Rotation of the prosthetic wrist and formation of the grip with the prosthetic hand may be performed in conjunction with rotation of the elbow and/or shoulder joints of the prosthetic arm and based on IMU data and selection of a grip.

In another aspect, a prosthetic wrist is described. The prosthetic wrist comprises a fixed portion, a rotatable portion, an actuator module and a processor. The fixed portion is configured to attach to a prosthetic or natural arm. The rotatable portion is configured to attach to a prosthetic hand that has an inertial measurement unit (IMU) to detect an orientation of the prosthetic hand. The actuator module is attached to both the fixed and rotatable portions and configured to actuate the rotatable portion relative to the fixed portion thereby rotating the prosthetic hand. The processor is in communication with the IMU and the actuator module and configured to execute a set of instructions to perform a method to control the actuator module. The method comprises receiving data from the IMU associated with the orientation of the prosthetic hand, identifying a desired grip for the prosthetic hand, determining a rotation for the rotatable portion based on i) the data from the IMU and ii) the desired grip, and causing the actuator module to perform the rotation.

In some embodiments of the prosthetic wrist, identifying the desired grip for the prosthetic hand comprises receiving an electromyography (EMG) signal from a user of the prosthetic wrist, detecting a gesture movement performed by the user, and determining the desired grip based on the detected gesture movement. Identifying the desired grip for the prosthetic hand may further comprise prompting the user to perform the gesture movement. Prompting the user to perform the gesture movement may comprise moving a finger of the prosthetic hand.

In some embodiments of the prosthetic wrist, determining the rotation for the prosthetic hand comprises determining Euler angles for the prosthetic hand based on the data from the IMU, and determining angular rotation data based on the determined Euler angles and on the desired grip. The angular rotation data may comprise a direction and an angle of rotation. The angular rotation data may comprise a speed of rotation.

In another aspect, a method of rotating a prosthetic wrist is described. The method comprises receiving data from an inertial measurement unit (IMU) that is coupled with a prosthetic hand, wherein the data is associated with an orientation of the prosthetic hand and the prosthetic hand is attached to the prosthetic wrist; identifying a desired grip for the prosthetic hand; determining a rotation for the prosthetic wrist based on i) the data from the IMU and ii) the desired grip, and causing the prosthetic wrist to perform the rotation.

In some embodiments of the method, identifying the desired grip for the prosthetic hand comprises receiving an electromyography (EMG) signal from a user of the prosthetic wrist, detecting a gesture movement performed by the user, and determining the desired grip based on the detected gesture movement. Identifying the desired grip for the prosthetic hand may further comprise prompting the user to perform the gesture movement. Prompting the user to perform the gesture movement may comprise moving a finger of the prosthetic hand.

In some embodiments of the method, determining the rotation for the prosthetic hand comprises determining Euler angles for the prosthetic hand based on the data from the IMU, and determining angular rotation data based on the determined Euler angles and on the desired grip. The angular rotation data may comprise a direction and an angle of rotation. The angular rotation data may comprise a speed of rotation.

In some embodiments, the method may further comprise forming the desired grip with the prosthetic hand. Causing the prosthetic wrist to perform the rotation and forming the desired grip with the prosthetic hand may be performed simultaneously.

In some embodiments of the method, the wrist rotation is about a single axis. The wrist rotation may be about two or more axes. The wrist rotation may be about a pitch axis and a roll axis.

In some embodiments of the method, the IMU comprises a nine-axis IMU including three accelerometers, three gyroscopes and three magnetometers.

In another aspect, another prosthetic hand and wrist system is described. The system comprises a prosthetic hand and a prosthetic wrist.

The prosthetic hand comprises a wrist attachment, a palm assembly, four prosthetic finger digits and a prosthetic thumb digit. The wrist attachment includes a connection ring and a ball bearing retainer on a proximal end of the wrist attachment. The palm assembly is attached to the wrist attachment and includes a hand chassis, a dorsal fairing, a palm fairing, an inertial measurement unit (IMU), a printed circuit board (PCB), and an on-off switch. The hand chassis is attached to the wrist attachment and includes structural walls having a motor assembly and a thumb rotator attached thereto. The dorsal fairing is attached to the hand chassis and faces in a dorsal direction forming a back of the prosthetic hand. The palm fairing is attached to the hand chassis and to the dorsal fairing and forms a palm of the prosthetic hand, with the palm and dorsal fairings forming a cavity therebetween. The IMU is attached to a dorsal side of the hand chassis and is configured to detect an orientation of the prosthetic hand. The PCB includes a processor and is attached to the hand chassis in the cavity formed by the dorsal and palm fairings. The PCB is in electrical communication with the IMU, a battery and with motors that control the prosthetic digits. The on-off switch is attached to the hand chassis and is in electrical communication with the PCB. A portion of the on-off switch may protrude through an opening of the palm fairing.

The four prosthetic finger digits are rotatably attached in a spaced configuration along a distal end of the prosthetic hand. Each prosthetic finger digit includes a finger knuckle assembly, a worm wheel, a gearbox, a knuckle fairing, a knuckle cap thinner, a retaining tab thinner, a wire, an extension spring and a fingertip assembly. The finger knuckle assembly is attached to the palm assembly. The worm wheel is attached at a proximal end to the finger knuckle assembly and has a portion with a hole. The gearbox contains a motor, a motor bearing, a worm gear, and a worm bearing therein, and includes two prongs having aligned holes and extending toward the palm assembly and defining a space in between the two prongs. The portion of the worm wheel with the hole is inserted into the space, and the gearbox is rotatably attached to the worm wheel via a gearbox pivot pin extending through the aligned holes of the worm wheel and gearbox. The knuckle fairing is rotatably coupled with the gearbox pivot pin and covers a distal portion of the gearbox. The knuckle cap thinner is connected to a distal end of the gearbox. The retaining tab thinner is rotatably connected to a distal end of the knuckle cap thinner. The wire connects the finger knuckle assembly to the retaining tab thinner and extends over a hinge point such that a closing rotation of the gearbox will pull on the wire and rotate the retaining tab thinner relative to the gearbox. The extension spring connects the retaining tab thinner to the gearbox such that the closing rotation of the gearbox will extend the spring thus causing the spring to bias the retaining tab thinner to an opening rotation. An opening rotation of the gearbox will cause the spring to pull on the retaining tab thinner to rotate the retaining tab thinner in an opening direction. The fingertip assembly includes a finger extension and a fingertip. The finger extension is attached to a distal end of the retaining tab thinner and the fingertip is attached to a distal end of the finger extension.

The prosthetic thumb digit is rotatably attached to a side of the prosthetic hand. The prosthetic thumb digit includes a thumb knuckle assembly, a worm wheel, a gearbox, a thumb fairing, a fixed fairing, and a thumb tip. The thumb knuckle assembly is attached to a side of the palm assembly. The worm wheel is attached at a proximal end to the finger knuckle assembly and has a portion with a hole. The gearbox contains a motor, a motor bearing, a worm gear, and a worm bearing therein. The gear box includes two prongs having aligned holes and extending toward the palm assembly and defining a space in between the two prongs. The portion of the worm wheel with the hole is inserted into the space. The gearbox is rotatably attached to the worm wheel via a gearbox pivot pin extending through the aligned holes of the worm wheel and gearbox. The thumb fairing is rotatably coupled with the gearbox pivot pin and covers a distal portion of the gearbox. The fixed fairing is coupled with the thumb knuckle assembly and covers a portion of the thumb fairing and covers a distal portion of the gearbox. The thumb tip is connected to a distal end of the gearbox.

The prosthetic wrist is attached to the prosthetic hand. The prosthetic wrist comprises a circular bearing race, a circular threaded front, a wrist actuator module, a pressure ring, a coupling piece, a coax subassembly, and a digital signal processor (DSP) cover.

The circular bearing race is located on a distal end of the prosthetic wrist and is configured to receive therein a corresponding bearing component for rotatable connection to the wrist attachment of the prosthetic hand. The circular threaded front is attached along an outer circumference of the bearing race and extends in the proximal directional.

The wrist actuator module comprises a body, an asynchronous motor (ASM), a motor driver printed circuit board (PCB), and the digital signal processor (DSP). The body defines a central passageway therethrough and has a distal circumferential end attached along an outer circumference of a proximal portion of the threaded front. The asynchronous motor (ASM) is coupled with the body. The motor driver PCB is in electrical communication with the ASM and with the DSP.

The pressure ring is attached to the outside of the distal end of the wrist actuator module and secures the wrist actuator module to the threaded front. The coupling piece has a base defining an opening therethrough and a series of tabs projecting distally from an outer edge of the base. The base is in mechanically communication with the wrist actuator module and in mechanical communication with the ASM such that rotation of the ASM will rotate the coupling piece. The coax subassembly has a cable extending through the central passageway of the wrist actuator module and a plug extending distally through the opening of the coupling piece. The digital signal processor (DSP) cover is attached to a proximal end of the wrist actuator module.

The DSP is disposed inside the DSP cover, with the DSP in electrical communication with the ASM and with the IMU of the prosthetic hand. The DSP is in communication with a memory having a set of instructions wherein the DSP is configured to execute the set of instructions to perform a method to control the ASM to transmit rotation to the prosthetic hand. The method comprises receiving data from the IMU associated with an orientation of the prosthetic hand, identifying a desired grip for the prosthetic hand, determining a rotation for the prosthetic hand based on i) the data from the IMU and ii) the desired grip, and causing the wrist actuator module to perform the rotation for the prosthetic hand by driving the ASM.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several embodiments in accordance with the disclosure and are not to be considered limiting of its scope, the disclosure will be described with additional specificity and detail through use of the accompanying drawings. In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the drawing, can be arranged, substituted, combined, and designed in a wide variety of different configurations, all of which are explicitly contemplated and make part of this disclosure.

FIG. 2D is a cross-section view of the prosthetic wrist of FIG. 1 taken along the line 2D-2D indicated in FIG. 2B.

FIG. 6A is a perspective view of the prosthetic wrist of FIG. 1 attached to an embodiment of a prosthetic lower arm.

FIG. 6C is a perspective view of the prosthetic wrist and lower arm system of FIG. 6A with the arm shown transparent for clarity, showing an electromyography (EMG) system.

FIGS. 12A-12F are sequential perspective views of the prosthetic wrist and arm of FIG. 6A showing simultaneous grip formation and rotation of the prosthetic hand.

DETAILED DESCRIPTION

Figure 1:
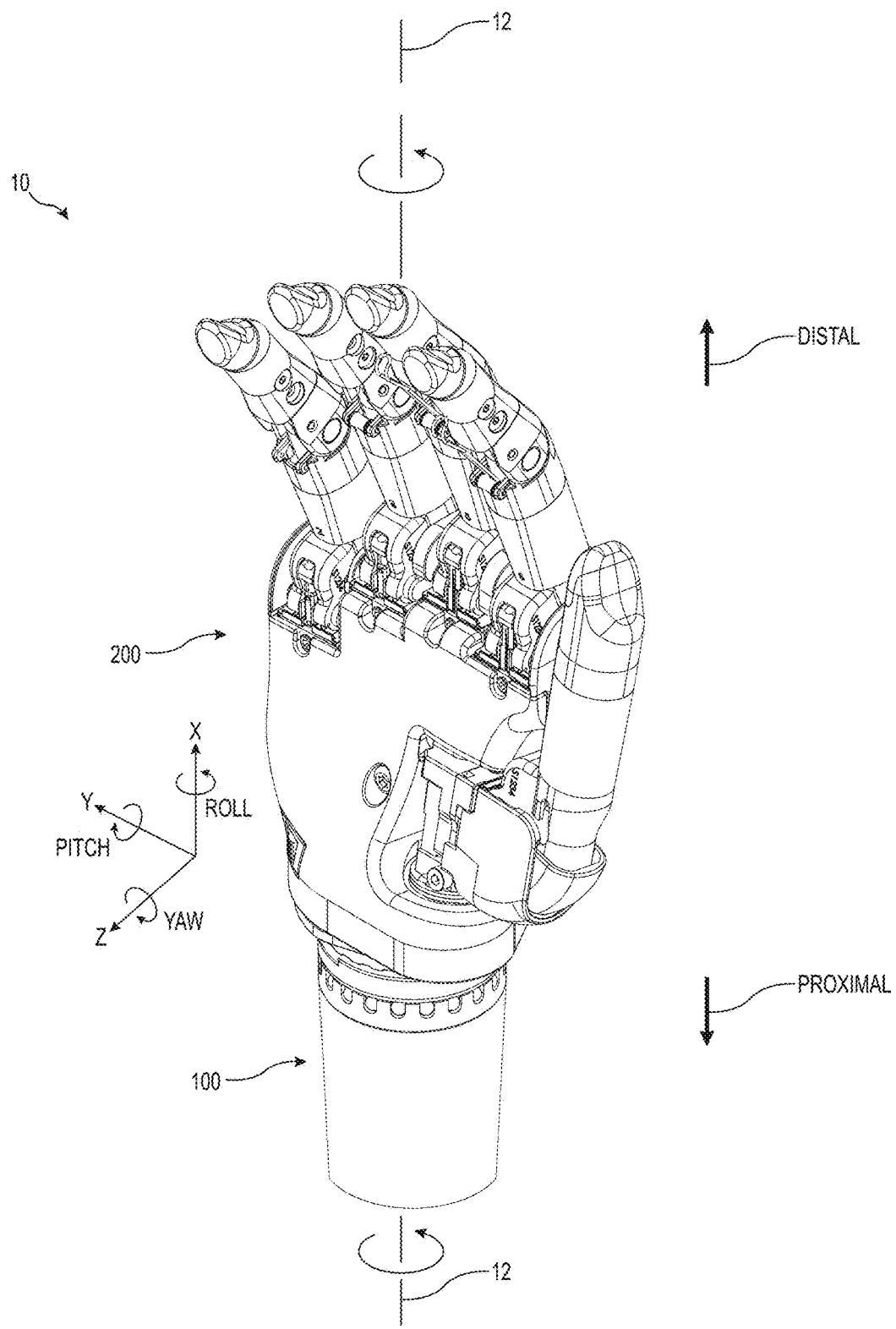
FIG. 1 is a perspective view of an embodiment of a prosthetic hand and wrist system that includes a prosthetic hand and a prosthetic wrist.

The following detailed description is directed to certain specific embodiments of the development. In this description, reference is made to the drawings wherein like parts or steps may be designated with like numerals throughout for clarity. Reference in this specification to "one embodiment," "an embodiment," or "in some embodiments" means that a particular feature, structure, or characteristic described in connection with the embodiment is included in at least one embodiment of the invention. The appearances of the phrases "one embodiment," "an embodiment," or "in some embodiments" in various places in the specification are not necessarily all referring to the same embodiment, nor are separate or alternative embodiments necessarily mutually exclusive of other embodiments. Moreover, various features are described which may be exhibited by some embodiments and not by others. Similarly, various requirements are described which may be requirements for some embodiments but may not be requirements for other embodiments.

The prosthetic hand and wrist system and methods described herein provide a more responsive upper limb prosthetic system for amputees. In some embodiments, the rotation of a prosthetic wrist is performed in conjunction with the formation of a grip with a corresponding prosthetic hand. Users can command a particular grip to be formed with the prosthetic hand, and the prosthetic wrist will rotate responsively and in an efficient manner to simulate natural hand and wrist movement. The prosthetic hand and wrist system and methods provide enhanced responsiveness of wrist rotation and other advantages. A prosthetic hand orientation sensor, such as an inertial measurement unit (IMU), communicates hand orientation data directly to one or more processors of the prosthetic wrist to determine wrist rotational position and thus necessary rotational movements for a particular chosen grip. This bypasses the need for more complex and time-consuming solutions, such as wrist encoder analysis and/or electromyography (EMG) sensor commands for wrist rotation, which are more cumbersome and delayed when switching from control of the prosthetic hand to the prosthetic wrist. By using the orientation sensor of the prosthetic hand to determine prosthetic wrist rotation, the prosthetic hand and wrist movements are collectively associated with orientation sensor data from only the prosthetic hand. The wrist rotation is thus more responsive to user commands, and more synchronized with grip formation of the prosthetic hand. The orientation sensor may be a nine-axis IMU, for example having a three-axis gyroscope, a three-axis accelerometer and a three-axis magnetometer. The desired prosthetic hand grip can be indicated with translations of the prosthetic hand along pre-determined paths, with muscle movements detected by EMG sensors, with selections made with mobile devices such as phones or wearables and/or with communicative sensors such as "grip chips" placed near or on items which the prosthetic hand may grasp. In conjunction with indication of the desired grip, data from the orientation sensor associated with the current prosthetic hand orientation is communicated to the prosthetic wrist. The necessary wrist rotation is then determined and performed based on the current orientation of the prosthetic hand and the indicated grip.

FIG. 1 is a perspective view of an embodiment of a prosthetic hand and wrist system 10. The prosthetic system 10 includes an embodiment of a prosthetic wrist 100 attached to an embodiment of a prosthetic hand 200.

For sake of description, various geometric references are used. A "distal" direction and a "proximal" direction are indicated. As shown, the prosthetic wrist 100 is located proximally relative to the prosthetic hand 200, and the prosthetic hand 200 is located distally relatively to the prosthetic wrist 100. The distal and proximal directions refer to, respectively, directions farther from and closer to a user of the prosthetic system 10 along the length of an arm of the user containing the prosthetic system 10. A longitudinal axis 12 is also indicated. The longitudinal axis 12 is an axis of rotation about which the prosthetic wrist 100 and hand 200 rotate. The distal and proximal directions may be directions along the longitudinal axis 12, for example when the prosthetic system 10 is oriented as shown. "Inner," "inward," and like terms refer to directions toward the longitudinal axis 12, while "outer," "outward," and like terms refer to directions away from the longitudinal axis 12, unless otherwise indicated.

The prosthetic wrist 100 is attached to the prosthetic hand 200 to cause movement of the prosthetic hand 200. A rotatable portion of the prosthetic wrist 100 may be coupled with, for example attached to, the prosthetic hand 200. The rotatable portion of the prosthetic wrist 100 rotates, thereby causing rotation of the prosthetic hand 200. The rotatable portion of the prosthetic wrist 100 may include one, some or all of the actuated, e.g. rotated, components of the prosthetic wrist 100, as described herein. The prosthetic wrist 100 causes rotation of the prosthetic hand 200 relative to an arm, prosthetic or natural, to which the prosthetic wrist 100 may be attached. The prosthetic wrist 100 may be attached to an arm or other components via a fixed portion of the prosthetic wrist 100. The fixed portion of the prosthetic wrist 100 may include one, some or all of the non-actuated, e.g. non-rotated, components of the prosthetic wrist 100, as described herein. In some embodiments, particular components of the fixed portion of the prosthetic wrist 100 may also couple with the prosthetic hand 200, for example a bearing race that guides rotation of the prosthetic hand 200, as described herein. The rotatable portion of the prosthetic wrist 100 may include one, some or all of the actuated, e.g. rotated, components of the prosthetic wrist 100, as described herein. The prosthetic wrist 100 and hand 200 rotate about the longitudinal axis 12. The prosthetic hand 200 may form a plurality of different grips, for example different palm and/or digit positions. The prosthetic system 10 may synchronize the rotation of the prosthetic wrist 100 with the formation of one of the grips with the prosthetic hand 200.

Further details of the prosthetic wrist 100 are described herein, for example with respect to FIGS. 2A-2E. Further details of the prosthetic hand 200 are described herein, for example with respect to FIGS. 3A-5B. Further details of prosthetic arms that may be used with the prosthetic system 10 are described herein, for example with respect to FIGS. 6A-8. Further details of systems and methods for synchronizing rotation of the prosthetic wrist 100 with grip formation of the prosthetic hand 200 are described herein, for example with respect to FIGS. 9-12F.

Figure 2A:
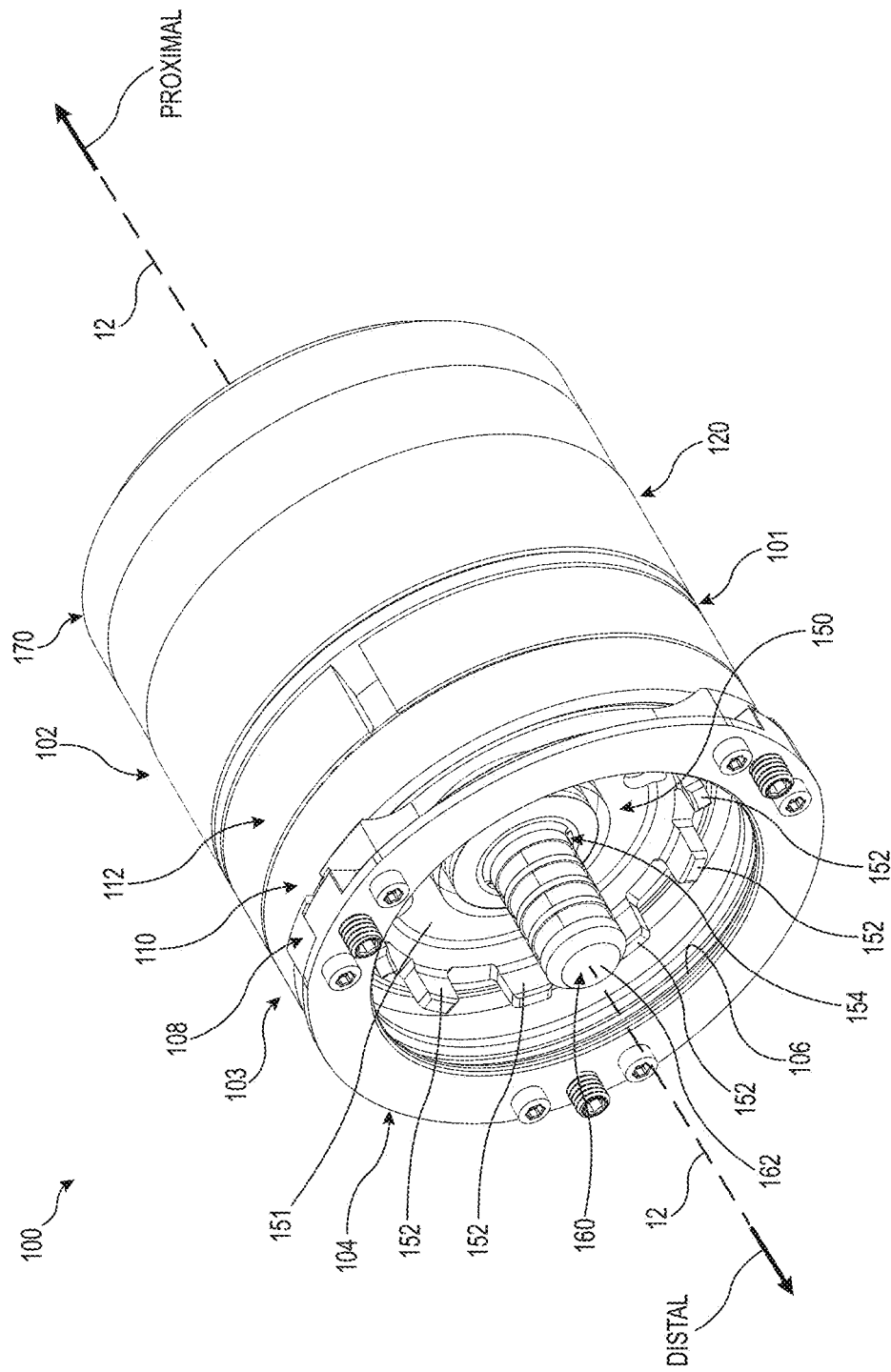
FIG. 2A is a perspective view of the prosthetic wrist of FIG. 1.
Figure 2B:
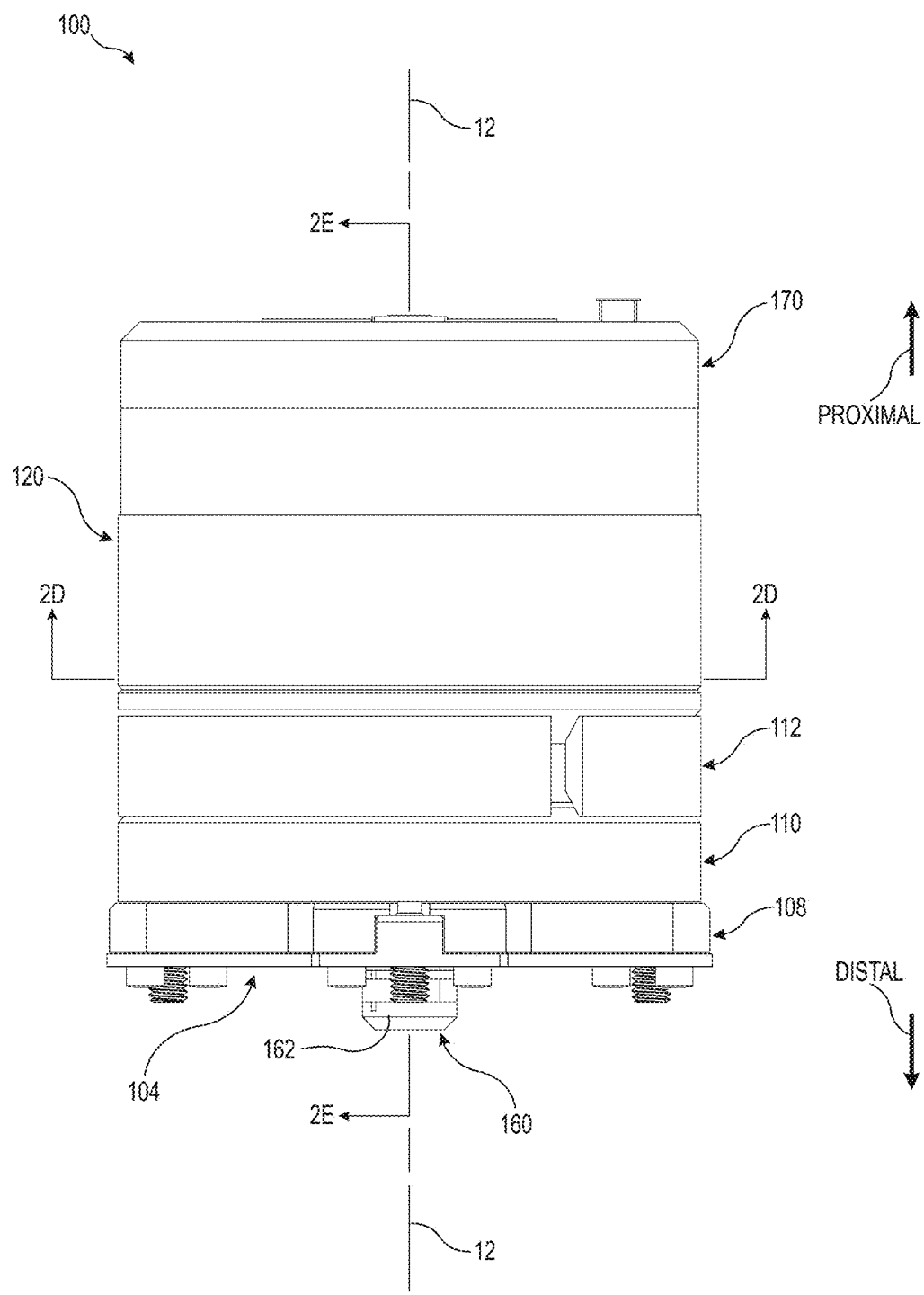
FIG. 2B is a top view of the prosthetic wrist of FIG. 1.
Figure 2C:
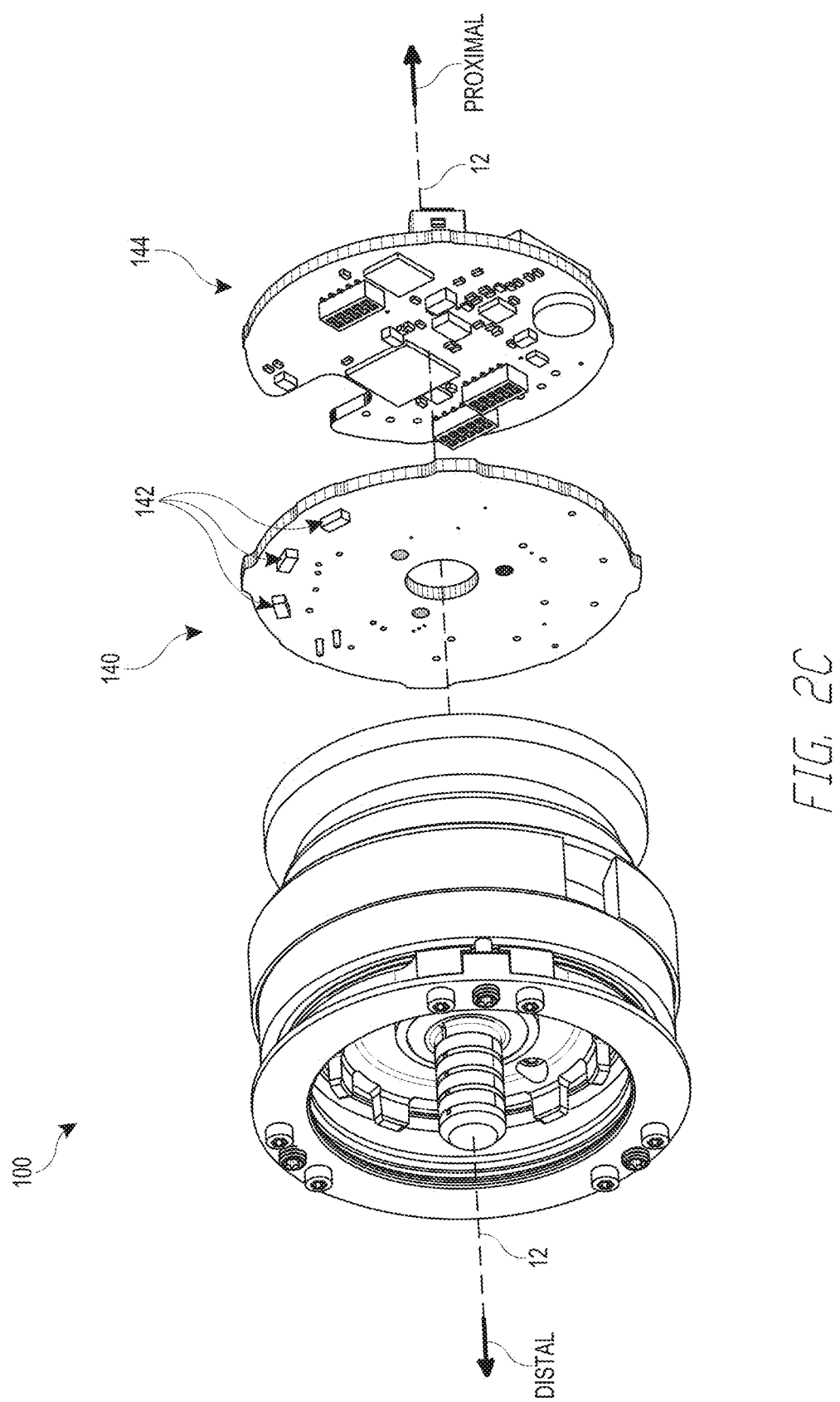
FIG. 2C is an exploded view of the prosthetic wrist of FIG. 1.
Figure 2E:
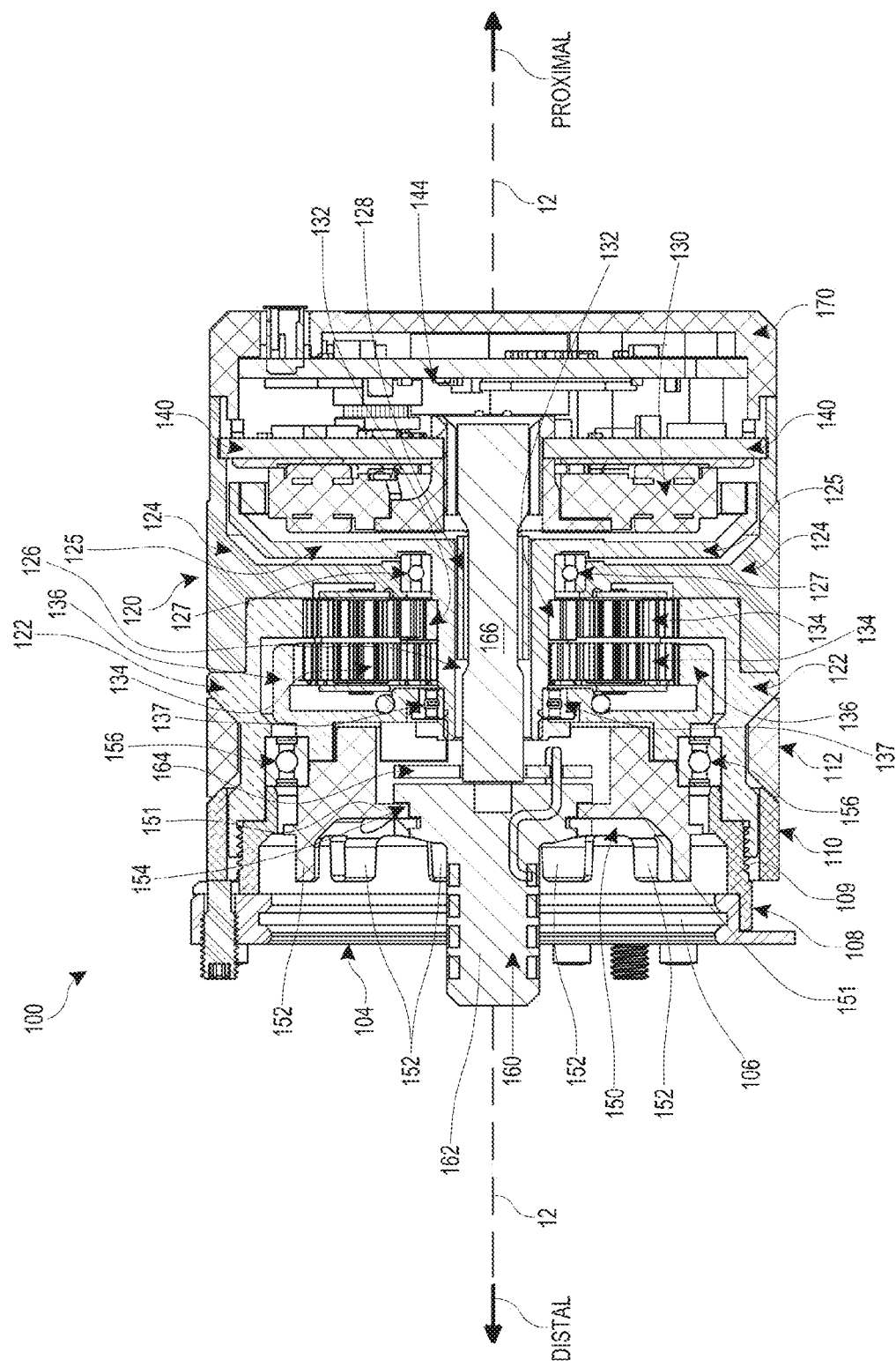
FIG. 2E is a cross-section view of the prosthetic wrist of FIG. 1 taken along the line 2E-2E indicated in FIG. 2B.

FIGS. 2A-2E are various views of the prosthetic wrist 100. FIG. 2A is a perspective view of the prosthetic wrist 100. FIG. 2B is a top view of the prosthetic wrist 100. FIG. 2C is an exploded view of the prosthetic wrist 100. FIG. 2D is a cross-section view of the prosthetic wrist 100 taken along the line 2D-2D indicated in FIG. 2B. FIG. 2E is a cross-section view of the prosthetic wrist of FIG. 1 taken along the line 2E-2E indicated in FIG. 2B.

The prosthetic wrist 100 includes a body 101. The body 101 forms the outer structure of the prosthetic wrist 100. The body 101 may be formed of metals, composites, plastics, polymers, other suitable materials, or combinations thereof. The body 101 has a generally cylindrical shape extending along the longitudinal axis 12. The body 101 extends from a proximal end 102 to a distal end 103 of the prosthetic wrist 100. The proximal end 102 is configured to attach to an arm, such as a natural or prosthetic arm, of a user of the prosthetic system 10. The distal end 103 is configured to attach to the prosthetic hand 200.

The prosthetic wrist 100 includes a bearing race 104. The bearing race 104 forms a distal end of the body 101. The bearing race 104 is located on the distal end 103 of the prosthetic wrist 100. The bearing race 104 has a generally circular shape with an opening through the center. The distal side of the bearing race 104 is generally flat and abuts a corresponding portion of a prosthetic arm or portion thereof. The proximal side of the bearing race 104 is generally flat and abuts a corresponding portion of the prosthetic wrist 100. Various fastening components, such as setscrews, bolts, etc., are attached to the bearing race 104 to facilitate connection with an arm. The bearing race 104 may be formed of metals, other suitable materials, or combinations thereof. The bearing race 104 is configured to couple with an arm and with corresponding components of the prosthetic hand 100. The bearing race 104 includes features for rotational connection with the prosthetic hand 100. The bearing race 104 guides rotation of the prosthetic hand 100.

The bearing race 104 includes a groove 106. The groove 106 guides the rotation of the prosthetic hand 100. The groove 106 is a recess extending circumferentially along an inner side of the bearing race 104. The groove 106 is shaped to receive therein corresponding bearing features that move along the groove 106 as the prosthetic hand 200 rotates. The prosthetic wrist 100 may thus include the circular bearing race 104 located on a distal end of the prosthetic wrist 100 configured to receive therein, for example in the groove 106, a corresponding bearing component for rotatable connection to the prosthetic hand 200. The groove 106 includes a square or rectangular recess with angled chamfer edges to guide a bearing component, such as a ball, of the prosthetic hand 200 along the length of the groove 106. The groove 106 may be or include other shapes, such as semi-circular, etc.

The prosthetic wrist 100 includes a front 108. The front 108 is located distally relative to the bearing race 104. The front 108 forms a distal portion of the body 101. The front 108 is generally circular with an opening in the center. The opening of the front 108 has rotatable components of the prosthetic wrist 100 rotating therein. The front 108 may be formed of metals, composites, other suitable materials, or combinations thereof. The distal end of the front 108 surrounds an outer wall of the bearing race 104. The threaded front 108 may thus be circular and attached along an outer circumference of the bearing race 104 and extending in the proximal directional. In some embodiments, the front 108 may attach with or to the bearing 104 in a variety of suitable ways, including friction fit, threads, fasteners, adhesive, other suitable mechanisms, or combinations thereof. A proximal portion of the front 108 includes a plurality of outer threads 109 along an outer circumferential wall of the front 108. The threads 109 are configured to threadingly engage with a corresponding proximal component of the prosthetic wrist 100. In some embodiments, there may be one thread 109. In some embodiments, the front 108 may attach with or to the bearing 104 in a variety of suitable ways, including threads, friction fit, fasteners, adhesive, other suitable mechanisms, or combinations thereof.

The prosthetic wrist 100 includes a pressure ring 110. The pressure ring 110 is an outer band extending circumferentially and forming an outer portion of the body 101. The pressure ring 110 is located proximally relative to the bearing race 104 and a portion of the front 108. The pressure ring 110 surrounds a portion of the front 108 and a portion of a distal body 122. In some embodiments, the pressure ring 110 may attach with the front 108 and/or the distal body 122, or other components of the prosthetic wrist 100, in a variety of suitable ways, including friction fit, fasteners, threads, adhesive, other suitable mechanisms, or combinations thereof. The pressure ring 110 may be relatively thin along the circumferential length of the pressure ring 110. The pressure ring 110 may be formed of a variety of suitable materials, including metals, composites, other materials, or combinations thereof. The pressure ring 110 provides an inward radial force along the circumference of the pressure ring 110 to various components of the prosthetic wrist 100, such as the front 108 and the distal body 122.

The prosthetic wrist 100 includes an expanding ring 112. The expanding ring 112 is an outer structure extending circumferentially to form an outer portion of the body 101 and defines an opening through or near a center thereof. The expanding ring 112 is located proximally relative to the pressure ring 110 and bearing race 104 and to portions of the front 108 and the distal body 122. The expanding ring 112 includes an inner, circumferential projection along an inner side of the expanding ring 112. The expanding ring 112 is circular. The expanding ring 112 may be other shapes, such as non-circular, etc. The expanding ring 112 as shown surrounds a portion of the distal body 122. The expanding ring 112 may also surround other features of the prosthetic wrist, for example the pressure ring 110. The expanding ring 112 sits on an outer projection of the distal body 122. In some embodiments, the expanding ring 112 may attach with the distal body 122, or other components of the prosthetic wrist 100, in a variety of suitable ways, including friction fit, fasteners, threads, adhesive, other suitable mechanisms, or combinations thereof. The expanding ring 112 may be formed of a variety of suitable materials, including metals, composites, other materials, or combinations thereof. The expanding ring 112 provides an expansive circumferential barrier to various components of the prosthetic wrist 100, such as the distal body 122 and the pressure ring 110.

The prosthetic wrist 100 includes an actuator module 120. The actuator module 120 forms a portion of the body 101. The actuator module 120 causes rotation of various components of the prosthetic wrist 100. Rotation of the various components of the prosthetic wrist 100 is transmitted to the prosthetic hand 200 to rotate the prosthetic hand 200. The actuator module 120 may include the distal body 122, a proximal body 124, a stator 125, a longitudinal passageway 126, one or more proximal bearings 127, one or more heat shrinks 128, a motor 130, a rotor 131, one or more central gears 132, and/or one or more peripheral gears 134, as described herein. The actuator module 120 includes the motor 130 that causes rotation of a coupling 150, as described herein. The actuator module 120 is located proximally relative to the bearing race 104. Various portions of the actuator module 120 are located proximally relative to the front 108, the pressure ring 110, and the expanding ring 112, as described herein.

The distal body 122 is a structural support formed of metals, composites, other suitable materials, or combinations thereof. The distal body 122 forms a portion of the body 101 of the prosthetic wrist 100. The distal body 122 may include a segmented cross-section extruded circularly about the longitudinal axis 112. A distal end of the distal body 122 is sandwiched in between the front 108 and the pressure ring 110. The distal end of the distal body 122 includes inner threads that engage with the outer threads 109 of the front 108. An outer surface of the distal body 122 opposite the threads contacts the inner surface of the pressure ring 110. An inner projection of the distal body 122 located proximally to the threads of the distal body 122 contacts a proximal surface of the front 108. An outer, angled projection of the distal body 122 located proximally of the pressure ring 110 contacts inner surfaces of the expanding ring 112 and a distal end of the proximal body 124. In some embodiments, the distal body 122 may support the motor 130, as described herein. In some embodiments, the distal body 122 may rotatably support various gears, rotors, etc. of the motor 130, as described herein.

The proximal body 124 is a structural support formed of metals, composites, other suitable materials, or combinations thereof. The proximal body 124 forms a portion of the body 101 of the prosthetic wrist 100. The proximal body 124 may include a segmented cross-section extruded circularly about the longitudinal axis 112. A distal end of the proximal body 124 surrounds a proximal end of the distal body 122. The proximal body 124 may attach to or with the distal body 122 with fasteners, adhesive, by friction fit, other suitable mechanisms, or combinations thereof. An inner ledge of the proximal body 124 extends radially inward and contacts an outer side of a proximal bearing 127, such as an outer race of the proximal bearing 127. An inner side of the proximal bearing 127, such as an inner race, may therefore rotate relative to the proximal body 124. The proximal body 124 further extends proximally from the inner ledge, forming an outer side of the body 101 at the proximal end 102 of the prosthetic wrist 100. In some embodiments, the distal body 122 may rotatably support various gears of the motor 130, for example the peripheral gears 134, as described herein.

The stator 125 is a moveable, structural component formed of metals, composites, other suitable materials, or combinations thereof. The stator 125 has a circular shape with an extended, cylindrical distal portion and a disc-shaped proximal portion having an outer lip. An outer surface of the distal portion of the stator 125 contacts an inner side of the proximal bearing 127. The stator 125 may therefore rotate relative to the outer side of the proximal bearing 127 and thus relative to the proximal body 124. An inner surface of the distal portion of the stator 125 surrounds a heat shrink 128 located at least partially inside the distal portion of the stator 125. The stator 125 may rotate relative to the heat shrink 128. An outer side of the distal portion of the stator 125 may be coupled with one or more central gears 132, as described herein. The stator 125 is rotated by the motor 130, for example by a rotor 131, and transmits rotation to the one or more central gears 132.

The stator bearing 127 allows for rotation of the stator 125 relative to other components of the prosthetic wrist 100. The stator bearing 127 may be a variety of suitable bearing types, including ball bearings, roller bearings, ball thrust bearings, roller thrust bearings, tapered roller thrust bearings, or other suitable types. The stator bearing 127, or components thereof such as inner/outer races, retainers, balls, etc., may be formed from a variety of materials, including metals, ceramics, other suitable materials, or combinations thereof.

The heat shrink 128 separates portions of the stator 125 from other features of the prosthetic wrist 100 located inside the heat shrink 128. The portions separated by the heat shrink 128 may therefore rotate relative to each other. The heat shrink 128 may surround a coax holder 166 extending through the inner passage of the heat shrink 128, allowing for rotation of the stator 125 relative to the coax holder 166, as described herein.

The motor 130 is a machine that produces movement. The motor 130 is an electric motor that produce rotational movement. The motor 130 produces rotation to produce a determined number of Hall Effect pulses corresponding to the required amount of rotation. The motor 130 may be a variety of suitable types of motors, such as a brushless direct current (DC) motor, a servo motor, a brushed motor, an ultrasonic motor, or other suitable motor types. The motor 130 provides movement to various portions of the prosthetic wrist 100 that causes rotation of the coupling 150.

The motor 130 is located proximally relative to the stator 125. The motor 130 is operatively coupled with the stator 125. The motor 130 includes a rotor 130 that is operatively coupled with the stator 125. The motor 130 may include other components operatively coupled with the stator 125. The motor 130 may be rigidly attached to the stator 125 via one or more shafts. Operation of the motor 130 causes the stator 125 to rotate. The motor 130 may be operated in a variety of manners. Angular orientation data is received by the processor 144 of the prosthetic wrist 100 and that angular information is calculated into the number of Hall Effect pulses that the motor 130 needs to drive to arrive at the correct position. The number of pulses per degree of the prosthetic wrist 100 may be about four. Other fewer or greater numbers of pulses per degree may be implemented. The motor 130 will rotate either clockwise or counterclockwise to a target rotational orientation determined by the number of pulses to reach the specified angle. The motor 130 may be operated in a variety of other manners, as described in further detail herein, for example with respect to FIGS. 9-12F. The stator 125 may be rigidly attached to the central gear 132, such that operation of the motor 130 causes the stator 125 and thus the central gear 132 to rotate. The rotation of the stator 125 and central gear 132 may be about the longitudinal axis 12.

The central gear 132 is a rounded, structural component having features for transmitting rotation. The central gear 132 may be formed of a variety of suitable materials, including metals, plastics, other suitable materials, or combinations thereof. The central gear 132 is circular and rotates about the longitudinal axis 12. The central gear 132 has teeth along an outer edge that mechanically communicate with corresponding features of the prosthetic wrist 100, such as one or more peripheral gears 134. In some embodiments, the central gear 132 may have other shapes and/or features that mechanically communicate with corresponding features of the prosthetic wrist 100. There may be one, two, or more central gears 132.

The peripheral gears 134 are rounded, structural components having features for transmitting rotation. The peripheral gears 134 may be formed of a variety of suitable materials, including metals, plastics, other suitable materials, or combinations thereof. The peripheral gears 134 are circular and rotate about axes parallel to the longitudinal axis 12. The axes of rotation of the peripheral gears 134 are located in a circular pattern about the longitudinal axis 12. The peripheral gears 134 are in mechanical communicate with the central gear 132, the distal body 122 and the rotator 136. Rotation of the central gear 132 will rotate one or more of the proximal peripheral gears 134, which will rotate the distal body 122, which will rotate the distal proximal gears, which will rotate the rotator 136, and ultimately rotate the coupling 150. In some embodiments, the distal body 122 and/or the rotator 136 may be and/or function as part of the central gear 132 as well. The peripheral gears 134 have teeth along outer edges that mechanically communicate with corresponding features of the prosthetic wrist 100, such as the central gear 132, the distal body 122 and/or a rotator 136. In some embodiments, the peripheral gears 134 may have other shapes and/or features that mechanically communicate with corresponding features of the prosthetic wrist 100. There may be one, two, three, four, five, six, seven, eight, nine, ten or more peripheral gears 134. The peripheral gears 134 may have outer diameters that are less than, equal to, or greater than outer diameters of the central gear 132. Thus, various gear ratios, mechanical advantages, etc. may be implemented with the prosthetic wrist 100.

The rotator 136 is a rounded, structural component that transmits rotation from the peripheral gears 134 to the coupling 150. The rotator 136 may be formed of a variety of suitable materials, including metals, plastics, other suitable materials, or combinations thereof. The rotator 136 circumferentially surrounds the peripheral gears 134 and extends therefrom in the distal direction. An inner surface of a proximal, outer portion of the rotator 136 is in mechanical communication with the peripheral gears 134. The rotator 136 rotates about the longitudinal axis 12 due to rotational forces transmitted from the peripheral gears 134. An inner surface of a distal, inner portion of the rotator 136 contacts an inner distal bearing 137. An outer surface of a distal, outer portion of the rotator contacts an outer distal bearing 156. The inner and outer distal bearings 137, 156 may be a variety of suitable bearing types, including ball bearings, roller bearings, ball thrust bearings, roller thrust bearings, tapered roller thrust bearings, or other suitable types. The inner and outer distal bearings 137, 156, or components thereof such as inner/outer races, retainers, balls, etc., may be formed from a variety of materials, including metals, ceramics, other suitable materials, or combinations thereof. The rotator 136 can therefore rotate with low friction due to contacts with the inner distal bearing 137 and the outer distal bearing 156. Rotation of the rotator 136 is transmitted to the coupling 150, which transmit rotation to the prosthetic hand 200, as described herein.

The prosthetic wrist 100 also includes a motor driver circuit 140, having Hall Effect sensors 142, and a processor 144. An exploded view of the prosthetic wrist 100 showing the circuit 140, sensors 142, and processor 144 is shown in FIG. 2C. The circuit 140 may be a printed circuit board (PCB), a printed circuit assembly (PCA), a printed circuit board assembly or PCB assembly (PCBA), a circuit card assembly (CCA), a backplane assembly, etc. The circuit 140 mechanically supports and electrically connects various electronic components of the prosthetic wrist 100 using conductive tracks, pads and other features etched from copper sheets laminated onto a non-conductive substrate. Components such as capacitors, resistors, sensors, active devices, etc. may be soldered on the circuit 140. The circuit 140 may contain these or other components embedded in the substrate. The circuit 140 may be single sided (e.g. one copper layer), double sided (e.g. two copper layers) or multi-layer (e.g. outer and inner layers). In some embodiments, the circuit 140 may be a printed wiring board (PWB). The circuit 140 is located adjacent and proximally relative to the motor 130. The circuit 140 may detect parameters of the motor 130, for example of the stator 131, for analyzing and determining rotations to perform with the motor 130, for example with the stator 131. The circuit 140 can be commanded, for example by the processor 144, to drive the motor 130 or portions thereof. The circuit 140 may include an additional processor in addition to the processor 144.

The circuit 140 includes one or more Hall Effect sensors 142. The sensors 142 are supported by the circuit 140. The sensors 142 are transducers that produce varied output voltages in response to a magnetic field. The sensors 142 are used for detecting movement (e.g. speed) and position of magnets or magnetic components of the motor 130, for example of the stator 131. The sensors 142 may operate as analog transducers, directly returning a voltage due to movement of the stator 131. With a known magnetic field, the distance between corresponding magnets of the stator 13 land sensors 142 can be determined. Using multiple sensors 142, the relative position of the magnets and thus of the stator 131 can be determined. The sensors 142 can acts as switches. For example, threshold distances between the magnets of the stator 13 land the sensors 142 can be detected. The sensors 142 may be used to detect the position of one or more permanent magnets of the stator 131, for example to analyze and control the speed, position, etc. of the stator 131. Data from the sensors 142 can be communicated to the processor 144 to drive the stator 131.

The processor 144 is located proximally relative to the circuit 140. The processor 144 may be a specialized microprocessor such as a digital signal processor (DSP). The processor 144 measures, filters and/or compresses signals from the various sensors and devices. The processor 144 is in electrical communication with the circuit 140, sensors 142 and the motor 130. The processor 144 is also in electrical communication with sensors of the prosthetic hand 200, such as an IMU, as described herein. The processor 144 may also be in electrical communication with external control devices, such as mobile devices like phones and wearables, as described herein. The processor 144 analyzes data, signals, etc. received from the various sensors and devices, and determines commands for driving the motor 130 via the circuit 140. The processor 144 communicates data with the circuit 140 and/or the additional processor of the circuit 140, which data may regard, for example, speed, direction and position of the motor 130 or portions thereof. Driving the motor 130 causes the coupling 150 to rotate, as described herein, thereby rotating the prosthetic hand 200.

The prosthetic wrist 100 includes the coupling 150. The coupling 150 is a structural connector that is configured to rotatably couple the prosthetic wrist 100 with the prosthetic hand 200. The coupling 150 includes a circular base 151 coupled with one or more teeth 152 extending in the distal direction from the base 151. The teeth 152 are located at or near a periphery or outer edge of the base 151. The teeth 152 are in a circular pattern. The base 151 and teeth 152 may be formed from a variety of materials, including metals, plastics, composites, other suitable materials, or combinations thereof. The base 151 defines an opening 154 through or near the center of the base 151. The base 151 may include holes or other features around the opening 154 for attaching the coupling to the rotator 136. The coupling 150 may be connected to the rotator 136 with fasteners, adhesives, other suitable mechanisms, or combinations thereof. An outer, proximal portion of the base 151 contacts the outer distal bearing 156. Thus the coupling 150 may rotate with the rotator 136 and be guided by the outer distal bearing 156. The coupling 150 and rotator 136 may contact the same inner race of the outer distal bearing 156. A portion of the coupling 150 may sit on a distal portion of the outer distal bearing 156.

The proximal end of the coupling 150 is shown rigidly connected to the rotator 136. Rotation of the rotator 136 thus causes the coupling 150 to rotate. The distal end of the coupling 150 is configured to couple with the prosthetic hand 200. With the prosthetic hand 200 connected to the coupling 150, rotation of the coupling 150 is thus transmitted to the prosthetic hand 200. The coupling 150 may connect with the prosthetic hand 200 in a number of configurations. For example, the teeth 152 may contact, either fixedly or passively, corresponding features of the prosthetic hand 200 that can be positioned between the teeth 152, as described herein. The coupling 150 may removably connect with the prosthetic hand 200, for example by friction fit, such that a threshold force applied to the prosthetic hand 200 in the distal direction and/or a threshold force applied to the prosthetic wrist 100 in the proximal direction will disconnect the coupling 150 from the corresponding features of the prosthetic hand 200. The coupling 150, bearing race 104 and other features may allow for a simple, quick and easy disconnect of the prosthetic hand 200 from the prosthetic wrist 100, as further described herein.

The prosthetic wrist 100 includes a coaxial assembly 160. The coaxial assembly 160 provides a wired transmission of electrical communication between the prosthetic wrist 100 and the prosthetic hand 200. The coaxial assembly 160 includes a plug 162, a circuit 164, a holder 166 and one or more cables 168. The plug 162 extends in the distal direction through and away from the coupling 150. The plug 162 is configured to connection to corresponding features of the prosthetic hand 100, such as a coaxial socket. The plug 162 is rounded and extends distally along the longitudinal axis 12 with a portion thereof protruding slightly beyond the bearing race 104 in the distal direction. The plug 162 includes conductive connections for electrically connecting with the prosthetic hand 200. The plug 162 may be rotationally stationary about the longitudinal axis 12 but allow for rotation of the prosthetic hand 200 about the plug 162 while maintaining electrical communication between the prosthetic wrist 100 and prosthetic hand 200.

The circuit 164 and cables 168 are in electrical communication with the plug 162. The circuit 164 may be a printed circuit board (PCB), or other types of suitable circuits. The circuit 164 may be in wired connection with the plug 162 and the cables 168. The circuit 164 may receive and/or transmit electrical signals from and/or to the plug 162 and cables 168. The circuit 164 is located proximally relative to the plug 162. The cables 168 extend in a proximal direction from the circuit 164. The cable 168 is a communication cable capable of transmitting data, information etc. The coaxial assembly 160 may include multiple cables 168. As shown, there are four cables 168. In some embodiments, the coaxial assembly 160 or portions thereof may not be necessary, for example the prosthetic hand 200 may be entirely or partially in wireless communication with the prosthetic wrist 100.

The holder 166 supports the one or more cables 168. The holder 166 is an elongated structural support extending through the passageway 126. A distal end of the holder 166 extends to the circuit 164. A proximal end of the holder 166 extends to the motor driver circuit 140. The circuit 140 may support the proximal end of the holder 166. The holder 166 may have a generally planar shape as shown. The holder 166 may be formed form a variety of materials, including plastics, polymers, other suitable materials, or combinations thereof.

The prosthetic wrist 100 includes a proximal cover 170. The proximal cover 170 is a structural end piece. The proximal cover 170 is rounded and connects with the proximal body 124. The cover 170 may in addition or alternatively connect with other features of the prosthetic wrist 100, such as the processor 144. The proximal cover 170 may connect with the various features by fasteners, threads, friction fit, adhesives, other suitable mechanisms, or combinations thereof. The proximal cover 170 may cover and protect the processor 144. The processor 144 may be disposed inside the proximal cover 170. The proximal cover 170 may also facilitate attachment with various features of other prosthetic components, such as prosthetic arms, as described herein.

The features of the prosthetic wrist 100 described herein relate to merely some embodiments of the prosthetic wrist 100. Other embodiments of the prosthetic wrist 100 and features thereof not explicitly described herein are within the scope of the present disclosure. In some embodiments, the prosthetic wrist 100 is configured to rotate about more than on axis. For example, the prosthetic wrist 100 may be configured to rotate about the longitudinal axis 12 and about one or more axes perpendicular to the longitudinal axis 12. An example X-Y-Z axis system is shown in FIG. 1, where the X axis is parallel to the longitudinal axis 12. Further indicated are roll, pitch and yaw rotations about, respectively, the X axis, Y axis and Z axis. The rotations may be in the directions indicated or in the opposite direction. The prosthetic wrist 100 may be configured to perform any combination of such rotations (roll, pitch and yaw), such as roll and pitch, roll and yaw, or roll, pitch and yaw. Further, the various embodiments of the prosthetic wrists 100 may be used with a multitude of embodiments of prosthetic hands. Some embodiments of such prosthetic hands are described herein with respect to the prosthetic hand 200. The prosthetic hand 200 may also be configured to perform various rotations. In some embodiments, the prosthetic hand 200 may be configured to perform any combination of the roll, pitch and yaw rotations, such as only pitch, only yaw, roll and pitch, roll and yaw, or roll, pitch and yaw. In some embodiments, wrist flexion and/or wrist deviation may be performed, e.g. pitch of the wrist in both rotational directions. The prosthetic hand 200 and/or the prosthetic wrist 100 may be configured to perform such rotations. In some embodiments, separate components may be incorporated with the prosthetic hand 200 and/or the prosthetic wrist 100 to perform such rotations. For example, a separate device in between the prosthetic hand 200 and the prosthetic wrist 100 may perform such rotations.

Figure 3A:
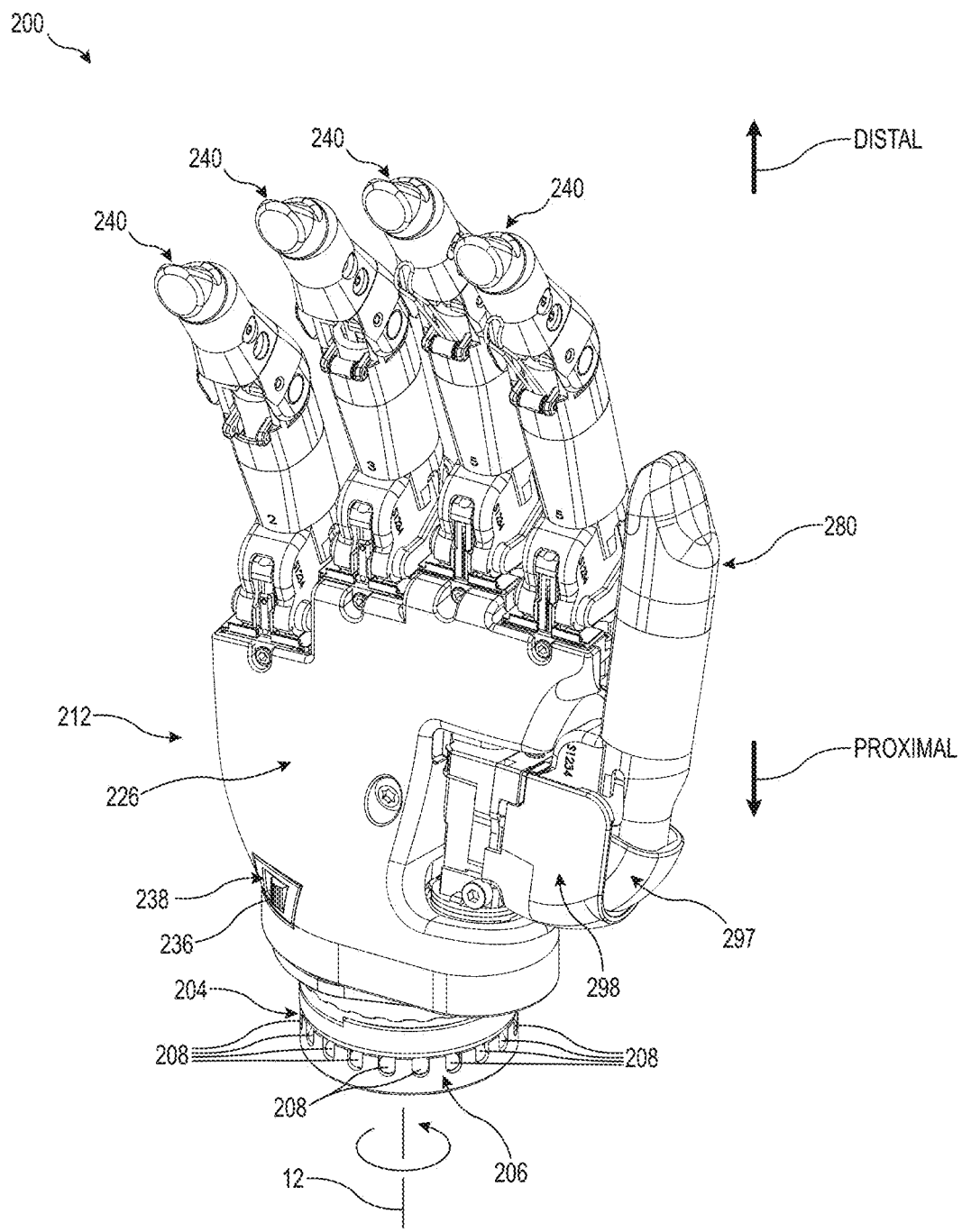
FIG. 3A is a perspective view of the prosthetic hand of FIG. 1.
Figure 3B:
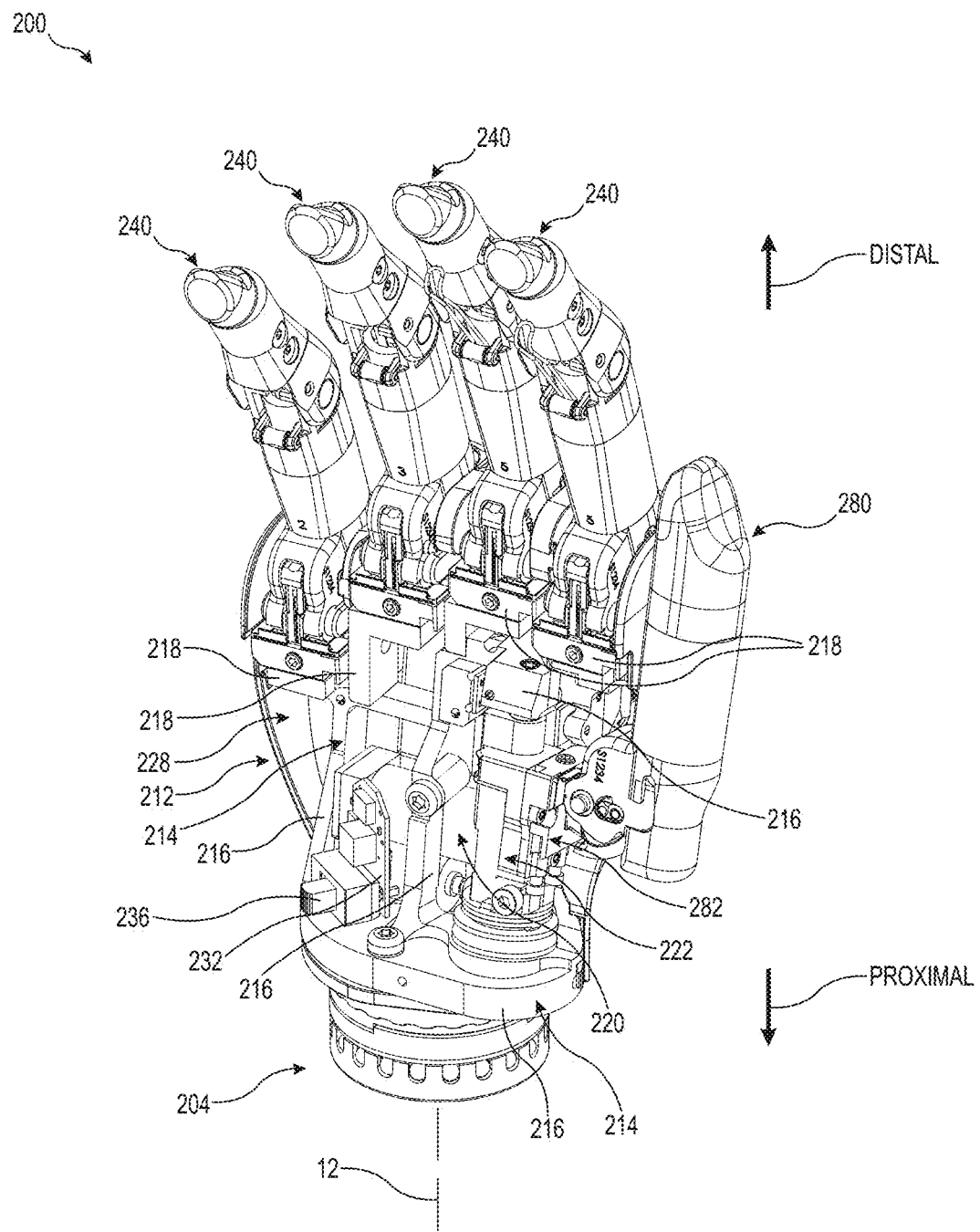
FIGS. 3B-3G are various views of the prosthetic hand of FIG. 1 with some components removed for clarity.
Figure 3C:
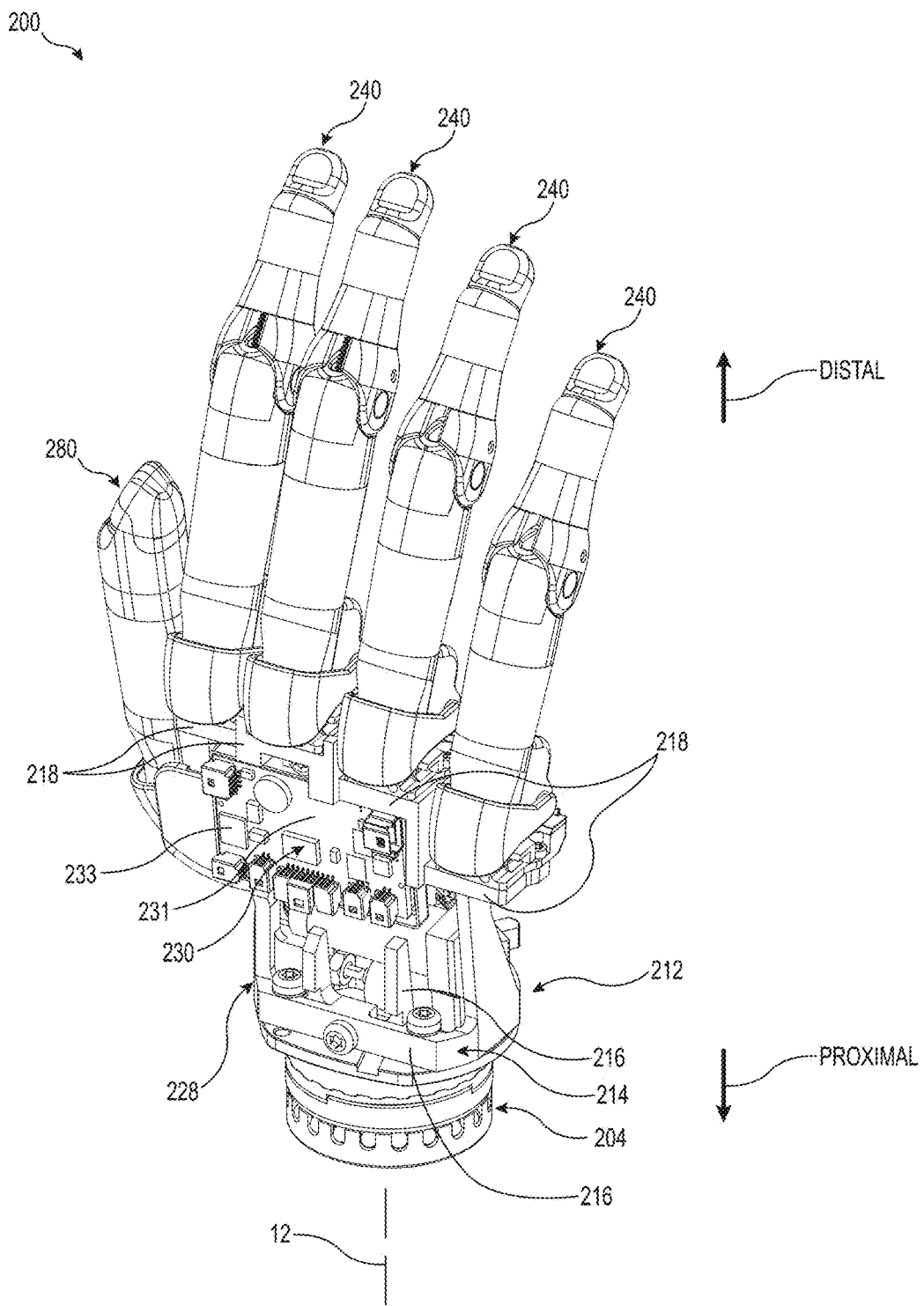
Figure 3D:
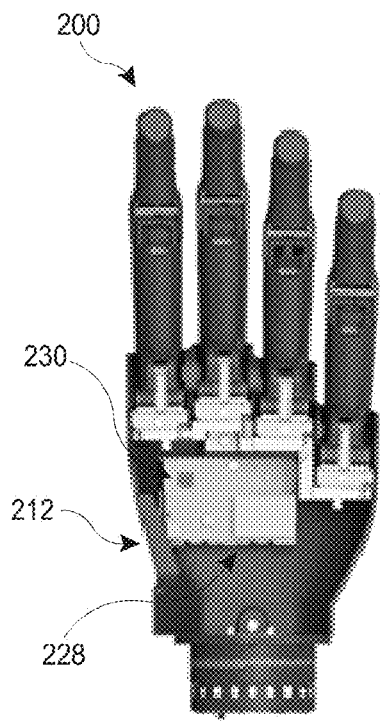
Figure 3E:
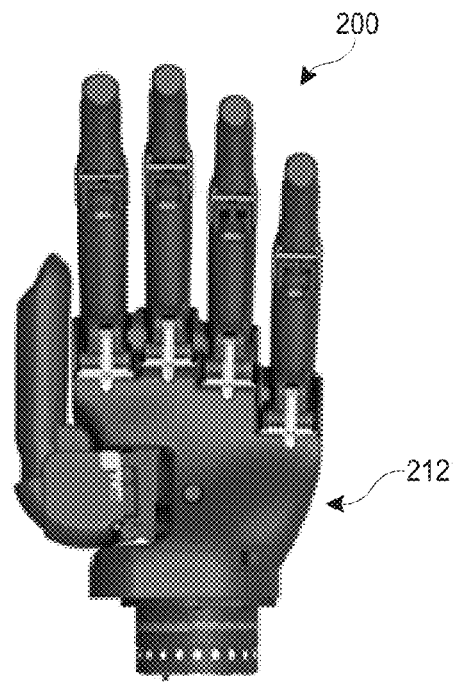
Figure 3F:
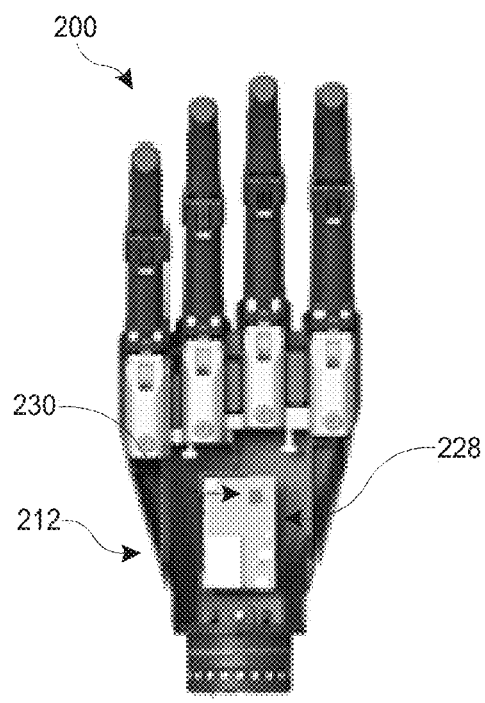
Figure 3G:
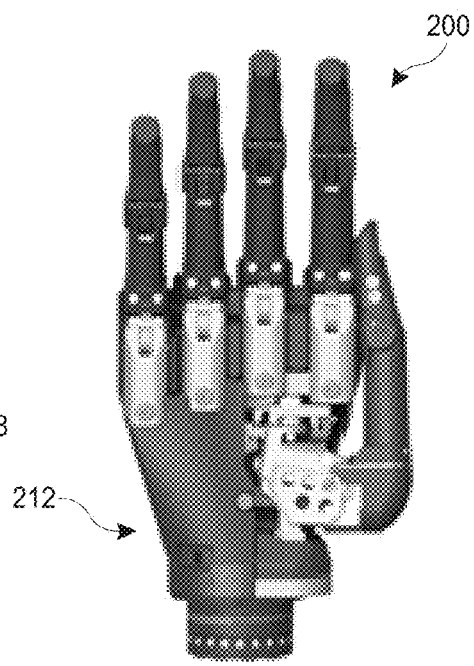
Figure 3H:
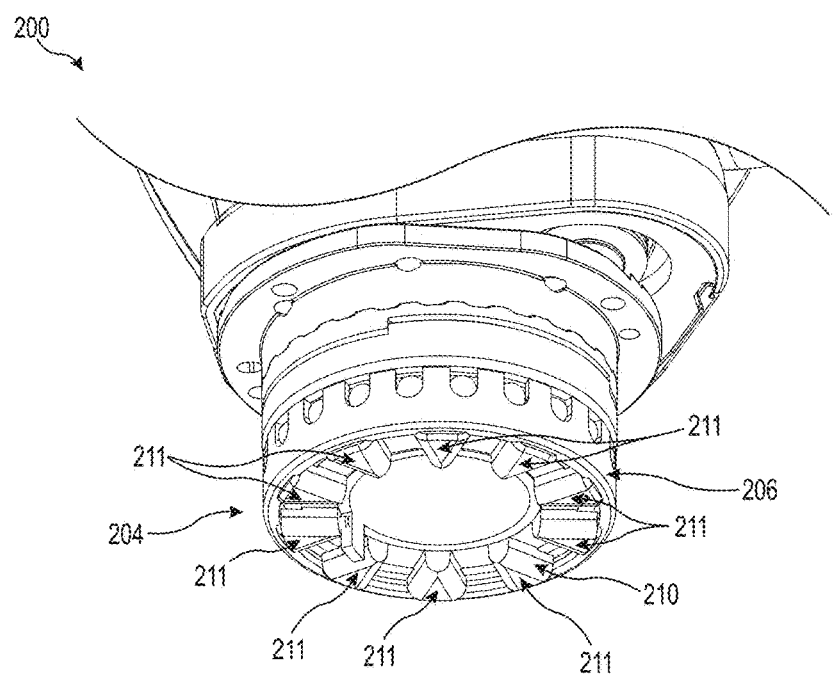
FIGS. 3H and 3I are bottom perspective and bottom views, respectively, of the prosthetic hand of FIG. 1.
Figure 3I:
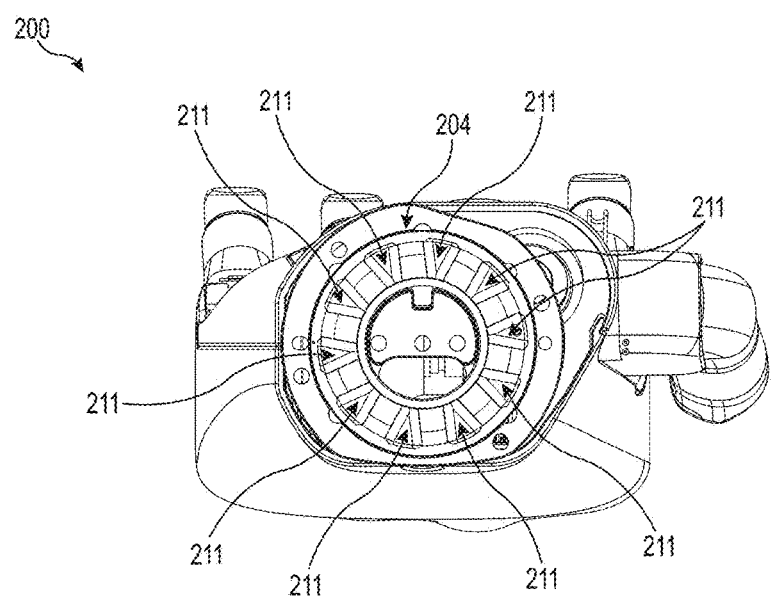

FIG. 3A is a perspective view of the prosthetic hand 200. FIGS. 3B-3G are various views of the prosthetic hand 200 with some components removed for clarity. FIG. 3H is a bottom perspective view and FIG. 3I is a bottom view of the prosthetic hand 200. The geometric references "distal" and "proximal" directions are indicated for sake of description. The longitudinal axis 12 is indicated as shown. The prosthetic hand 200 connects to and is rotated by the prosthetic wrist 100. The prosthetic hand 200 may rotate about the longitudinal axis 12. The prosthetic hand 200 is capable of forming a multitude of grips, for example various orientations of one or more digits and/or a palm. The prosthetic hand 200 may form such grips in sync with rotation of the prosthetic hand 200, as described herein. The prosthetic hand 200 described herein is merely an example of a prosthetic hand that may be implemented. Other prosthetic hands may be implemented, for example as described in U.S. Pat. No. 8,696,763, titled PROSTHETIC APPARATUS AND CONTROL METHOD and issued on Apr. 15, 2014, the entire contents of which are incorporated by reference herein for all purposes.

The prosthetic hand 200 includes a wrist attachment 204. The wrist attachment 204 may be a quick wrist disconnect (QWD) device, allowing for quick connection to and/or quick disconnection from the prosthetic wrist 100. The wrist attachment 204 is a structural connector on the proximal end of the prosthetic hand 200. The wrist attachment 204 includes a ball bearing retainer 206 having one or more ball bearings 208 contained therein. The ball bearing retainer 206 extends in the distal direction and is configured to be received by the prosthetic wrist 100. The ball bearing retainer 206 may be received within the bearing race 104 of the prosthetic wrist 100. The ball bearings 208 may be received into the groove 106 of the bearing race 104. The ball bearings 208 may rotate within the groove 106 as the prosthetic hand 200 is rotated by the prosthetic wrist 100. The ball bearing retainer 206 and ball bearings 208 may form a variety of different bearing types, including ball bearings, roller bearings, ball thrust bearings, roller thrust bearings, tapered roller thrust bearings, or other suitable types. The ball bearing retainer 206 and ball bearings 208 be formed from a variety of materials, including metals, ceramics, other suitable materials, or combinations thereof.

The wrist attachment 204 includes a locking ring 210 having a series of projections 211 (see FIGS. 3H and 3I) for connecting to the coupling 150. The locking ring 210 is a rounded structure coupled with the wrist attachment 204. The locking ring 210 may be coupled with, for example attached directly to, the ball bearing retainer 206. The locking ring 210 engages with the coupling 150 of the prosthetic wrist 100. The projections 211 may be complementary structures that correspond to and fit in between the teeth 152 of the coupling 150. The projections 211 are raised, triangular portions of the locking ring 210 defining rectangular spaces therebetween into which the teeth 152 are received. The projections 211 and/or spaces defined thereby may have other shapes.

Rotation of the coupling 150 transmits rotation to the wrist attachment 204 via the teeth 152 and projections 211. When engaged together, the projections 211 may passively contact the teeth 152 such that lateral or circumferential movement of the projections 211 relative to the teeth 152 is inhibited by the teeth 152. When engaged together, the projections 211 may not be inhibited by the teeth 152 from moving axially in the distal direction away from the teeth 152. The base 152 may inhibit axial movement of the projections 211 in the proximal direction. The bearing race 104, such as the groove 106, may also prevent axial movement of the ball bearings 208 and thus of the prosthetic hand 200 in the proximal and/or distal directions.

The prosthetic hand 200 includes a palm assembly 212 connected to four prosthetic finger digits 240 and one prosthetic thumb digit 280. The palm assembly 212 is a structural assembly forming a palm portion of the prosthetic hand 200. The palm assembly 212 includes a hand chassis 214 having one or more chassis walls 216. FIG. 3B is a palm-side view and FIG. 3C is a back-side view of the prosthetic hand 200. "Palm-side" and "back-side" are used here in their ordinary sense with respect to natural hands. Both FIGS. 3B and 3C have some features removed for clarity, for example to see interior components of the prosthetic hand 200.

The hand chassis 214 is a structural support for various features of the prosthetic hand 100. The walls 216 extend in various directions to support such features. Walls 216 at the proximal end of the hand chassis 214 connect to the wrist attachment 204. The hand chassis 214 may be connected to the wrist attachment 204 with fasteners, threads, other suitable mechanisms, or combinations thereof. The walls 216 may extend in the distal direction to a distal end of the palm assembly 212.

The walls 216 at the distal end of the hand chassis 214 connect to one or more knuckle blocks 218. The knuckle blocks 218 are structural connectors that connect the palm assembly 212 to the prosthetic finger digits 240. The prosthetic thumb digit 280 may similarly attach to a thumb knuckle block on the thumb-side of the palm assembly 212. Further details of the prosthetic finger digits 240 and the prosthetic thumb digit 280 are described herein, for example with respect to FIGS. 4A-4B and FIG. 5A-5B respectively.

The prosthetic hand 200 includes a motor assembly 220 and thumb rotator 222. The motor assembly 220 and thumb rotator 222 may be part of the palm assembly 212. The motor assembly 220 causes movement, for example rotation, of the prosthetic thumb digit 280 via the thumb rotator 222. The motor assembly 220 may include an electric motor for causing such movement. The motor assembly 220 may include a variety of suitable types of motors, such as a brushless direct current (DC) motor, a servo motor, a brushed motor, an ultrasonic motor, or other suitable motor types. The thumb rotator 222 may transmit movement from the motor assembly 220 to the prosthetic thumb digit 280. The motor assembly 220 and thumb rotator 222 may cause the prosthetic thumb digit 280 to rotate about one or more axes.

The prosthetic hand 200 includes a dorsal fairing 224 (see FIG. 6B) and a palm fairing 226. The dorsal fairing 224 is located on the dorsal or back-side of the prosthetic hand 200. An outer side of the dorsal fairing 224 faces in a dorsal direction when attached to the prosthetic hand 200, forming a back-side of the prosthetic hand 200. The palm fairing 226 is located on the palm-side of the prosthetic hand 200 opposite the dorsal fairing 224. An outer side of the palm fairing 226 faces in a palm direction when attached to the prosthetic hand 200, forming a palm side of the prosthetic hand 200. In FIG. 3B, the palm fairing 226 has been removed for clarity. In FIG. 3C, the dorsal fairing 224 has been removed for clarity. The dorsal and palm fairings 224, 226 are structural covers of the prosthetic hand 200. The dorsal and palm fairings 224, 226 may be formed of composites, plastics, polymers, metals, other suitable materials, or combinations thereof. The dorsal and palm fairings 224, 226 may be fastened to the prosthetic hand 200, for example to the hand chassis 214 or walls 216 thereof. The dorsal and palm fairings 224, 226 may, in addition or alternatively, be attached to these or other features of the prosthetic hand 200 with a variety of other suitable mechanisms.

The prosthetic hand 200 defines a cavity 228. The cavity 228 may be inside the palm assembly 212. The cavity 228 is formed at least in part by the dorsal and palm fairings 224, 226. The cavity 228 may contain various features of the prosthetic hand 200, such as the hand chassis 214, the motor assembly 220 and associated motor, the thumb rotator 222, the knuckle blocks 218, the thumb knuckle block, and/or other features.

The prosthetic hand 200 includes an inertial measurement unit (IMU) 230. The IMU 230 is an electronic device that detects and communicates various parameters related to the orientation of the IMU 230 and thus of the prosthetic hand 200. The IMU 230 may measure accelerations and/or speeds (i.e. rates), which may be linear and/or angular. The IMU 230 may measure magnetic fields. The IMU 230 may incorporate one or more accelerometers, gyroscopes, and/or magnetometers. The IMU 230 as shown is a nine-axis IMU, including a three-axis accelerometer, a three-axis gyroscope, and a three-axis magnetometer.

The prosthetic hand 200 includes one IMU 230. In some embodiments, the prosthetic hand 200 may include multiple IMUs 230. As shown in FIG. 3C, the IMU 230 is located on a back-side of the prosthetic hand 200, connected to a back-side of the hand chassis 214. The IMU 230 may be located in various positions of the prosthetic hand 200 and attached in various manners, for example depending on the size, type, etc. of the prosthetic hand 200. Additional embodiments of the prosthetic hand 200 showing alternative locations of the IMU 230 are shown in FIGS. 3D-3G. FIG. 3D is a back-side view with the dorsal fairing 224 removed, and FIG. 3E is a palm-side view, of a relatively smaller prosthetic hand 200 including the IMU 230 orientated horizontally. FIG. 3F is a back-side view with the dorsal fairing 226 removed, and FIG. 3G is a palm-side view with part of the palm fairing 226 removed, of a relatively larger prosthetic hand 200 including the IMU 230 orientated vertically. FIGS. 3D and 3F do not include the prosthetic thumb digit 280 for clarity.

The IMU 230 detects one or more accelerations, one or more rates of movement and magnetic field strengths in one or more directions to determine an orientation of the prosthetic hand 230 in three-dimensional space. The IMU 230 as shown detects accelerations along three orthogonal directions, rates of movement along three orthogonal directions, and magnetic field strength along three orthogonal directions. The IMU 230 may detect the accelerations, rates and magnetic field strengths along the same three orthogonal directions. In some embodiments, the IMU 230 may detect the accelerations, rates and magnetic field strengths along different directions. The IMU 230 may communicate the detected parameters to other features of the prosthetic hand 200 and/or to the prosthetic wrist 100. The IMU 230 may communicate the detected parameters to the processor 144 of the prosthetic wrist 100. The IMU 230 may communicate the detected parameters to a communications device associated with the processor 144. The IMU 230 may communicate the detected parameters to other devices, electronics, etc. of the prosthetic wrist 100. The IMU 230 may communicate the detected parameters to a processor, communications device, circuit, or other electronics of the prosthetic hand 200. In some embodiments, the IMU 230 may perform calculations based on the detected parameters and communicate the results of those calculations to the aforementioned devices.

The prosthetic hand 200 includes a circuit 231 and processor 233. The prosthetic hand 200 may also include a speed boost circuit 232. The circuits 231, 232 are a printed circuit boards (PCB) in electrical communication with the processor 233. The circuit 231 is in communication with the processor 233 and the IMU 230. The circuit 231 may be a variety of suitable types of electronic circuits. The processor 233 may be a variety of suitable types of processors, including those described with respect to the processor 144 of the prosthetic wrist 100. The circuit 231 and/or processor 233 are in electrical communication with the various electronics of the prosthetic hand 200, including the motor assembly 220, the IMU 230, the prosthetic finger digits 240 and/or actuators thereof, the prosthetic thumb digit 280 and/or actuators thereof, one or more batteries, and other devices. The processor 233 measures, filters and/or compresses signals from the various sensors and devices of the prosthetic hand 200 and controls movement of the prosthetic hand 200, for example movement of the prosthetic finger digits 240 and/or the prosthetic thumb digit 280. The circuit 231 and/or processor 233 may receive EMG signals and drive the prosthetic digits 240, 280 via an H bridge circuit chip, e.g. one H bridge circuit chip for each of the prosthetic digits 240, 280. The circuit 231 and/or processor 233 may be in communication with one or more grip chips, as described herein. The grip chips may be electronic sensors placed at or near items where particular grips are desirable. Different particular grip chips may be used for various items, such as a "cup" grip chip placed near cups, so that the prosthetic hand 200 forms a grip to hold a cup when the prosthetic hand 200 is within proximity of the "cup" grip chip. This is merely one example and other suitable grip chips may be used The speed boost circuit 232 may be a speed boost PCB. The speed boost circuit 232, for example the speed boost PCB, may increase an input voltage enabling the prosthetic digits to move, for example rotate, at a faster rate, acceleration, etc. The speed boost circuit 232 includes an on-off switch 236 that protrudes through an opening 238 of the palm fairing. The on-off switch 236 can be toggled to power the electronics of the prosthetic hand 200 on and off. The on-off switch 236 can also control powering the prosthetic wrist 100 on and off, for example via the coaxial assembly 160.

The prosthetic hand 200 can form various grips. The prosthetic finger digits 240 and prosthetic thumb digit 280 may actuate, for example rotate, to form the grips. In some embodiments, the palm assembly 212 can rotate, for example along the longitudinal axis 12 and/or along other axes. The formation of various grips with the prosthetic hand 200 is performed in sync with the wrist rotation by the prosthetic wrist 100. The prosthetic finger digits 240 and prosthetic thumb digit 280 actuate based on commands sent to various actuators, as described herein.

Figure 4A:
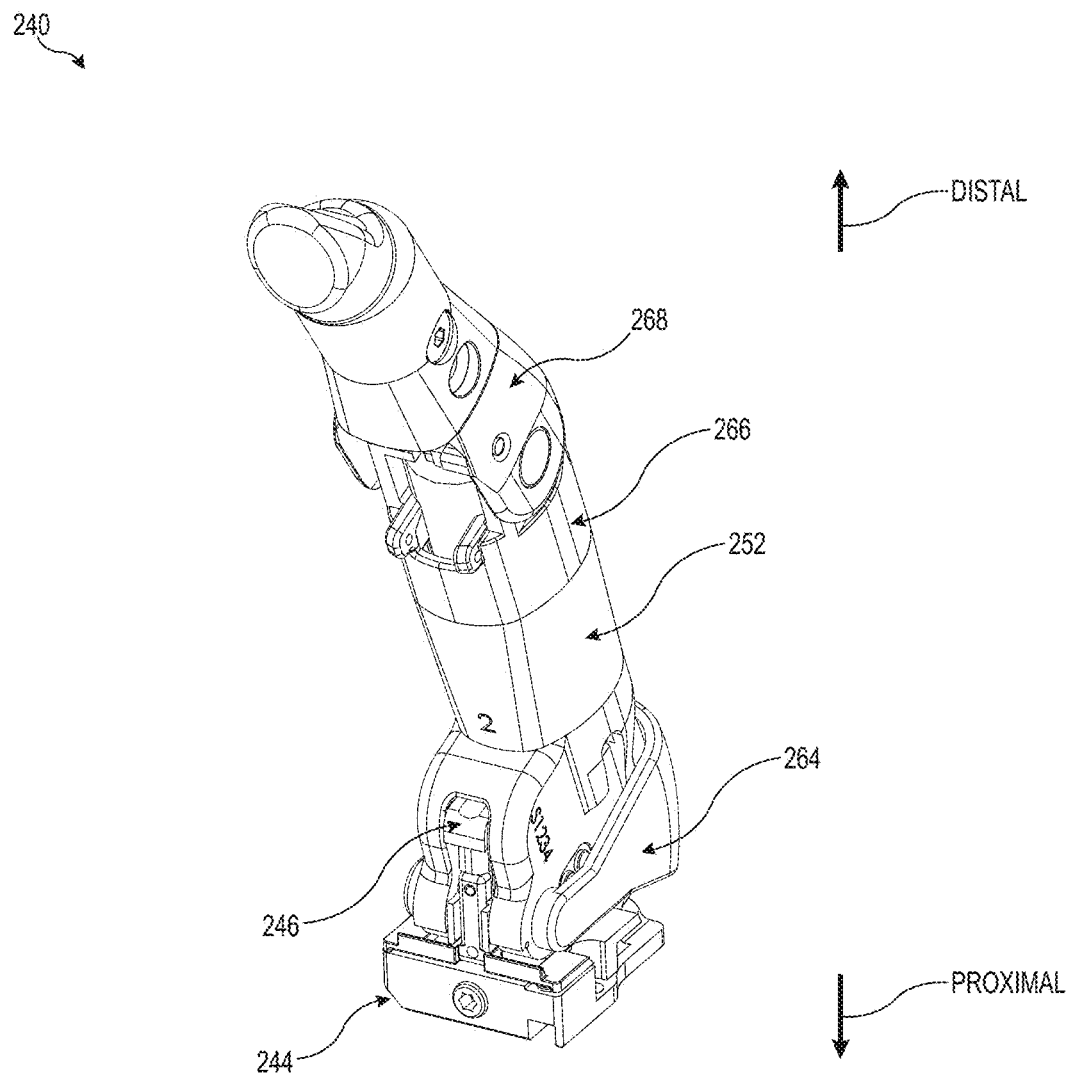
FIG. 4A is a perspective view of a prosthetic finger digit of the prosthetic hand of FIG. 1.
Figure 4B:
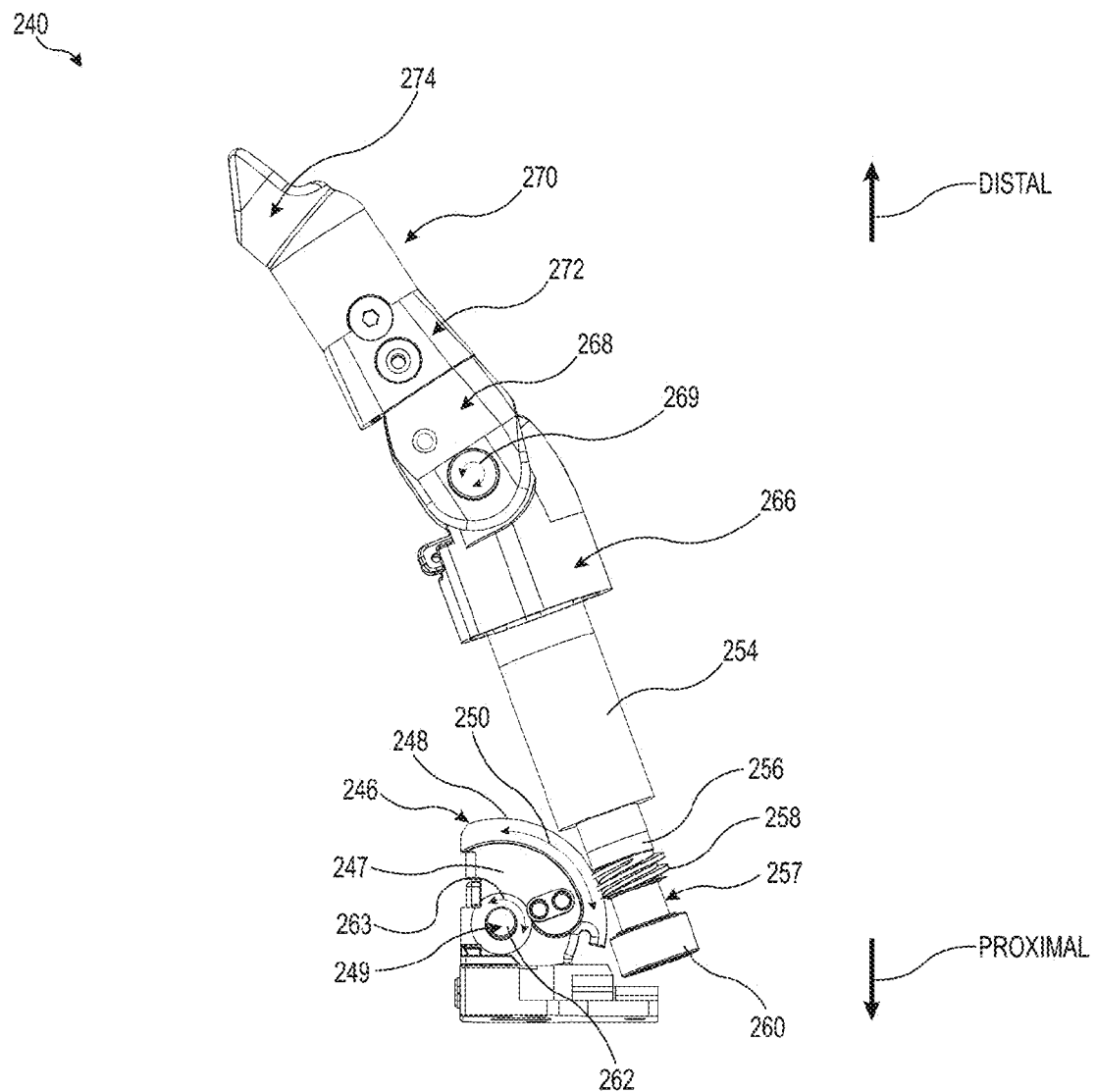
FIG. 4B is a side view of the prosthetic finger digit of FIG. 4A with some components removed for clarity.
Figure 4C:
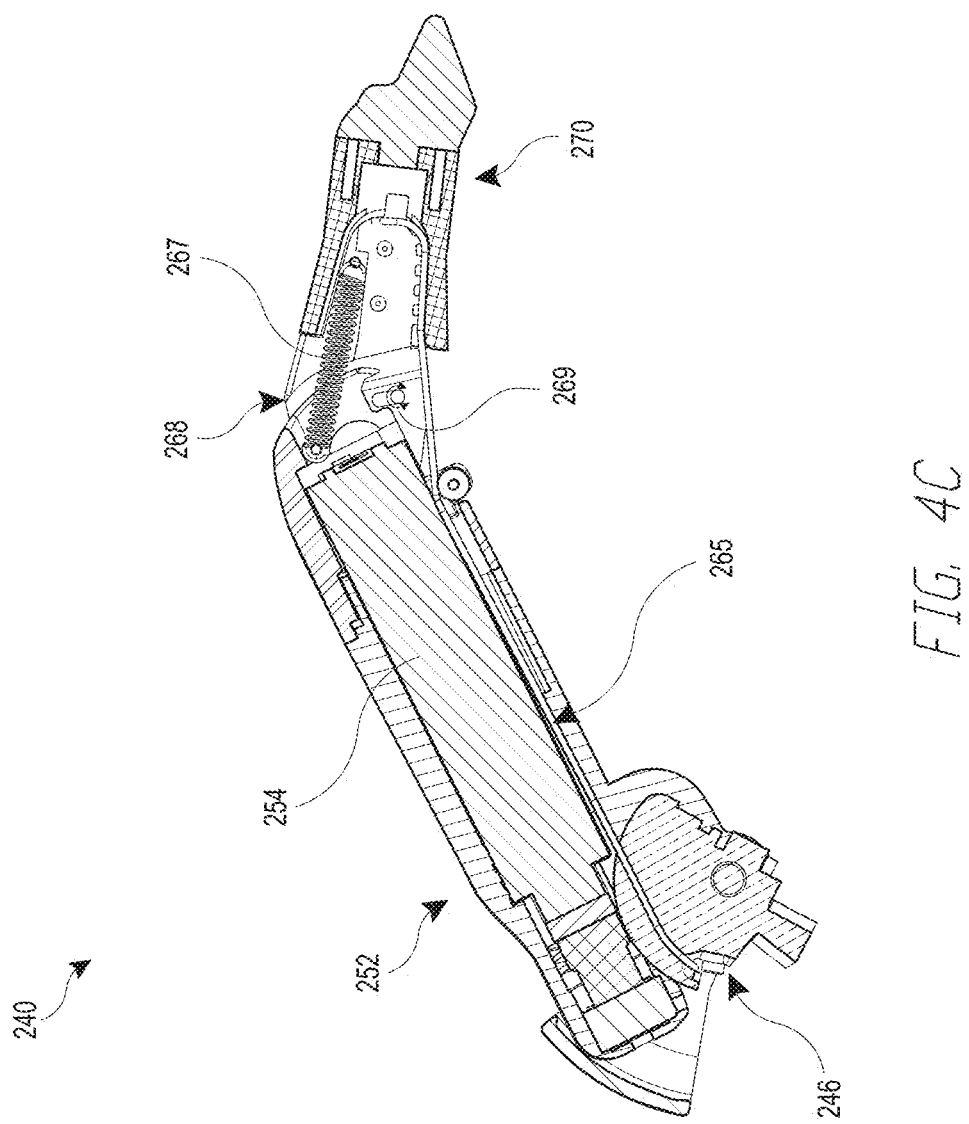
FIG. 4C is a side cross-section view of the prosthetic finger digit of FIG. 4A having a wire and spring for rotating outer portions of the prosthetic finger.

FIG. 4A is a perspective view of one of the prosthetic finger digits 240 of the prosthetic hand 100. FIG. 4B is a side view of the prosthetic finger digit 240 with some components removed for clarity. FIG. 4C is a side cross-section view of the prosthetic finger digit 240 showing a wire 265 and spring 267 for rotating outer portions of the prosthetic finger 240. The prosthetic finger digits 240 may have the same or similar features and/or functionalities as each other. The prosthetic finger digits 240 may be different sizes, for example to mimic natural finger sizes or to accommodate smaller or larger prosthetic hands 200. The following description may apply to all of the prosthetic finger digits 240 regardless of these variations in size. The prosthetic finger digits 240 and components thereof may be formed of plastic, metal, composite, other suitable materials, or combinations thereof.

The prosthetic finger digit 240 includes a finger knuckle assembly 244. The finger knuckle assembly 244 is a structural attachment for connecting the prosthetic finger digit 240 to the prosthetic hand 200, for example to the hand chassis 214. A worm wheel 246 is attached to the finger knuckle assembly 244. The worm wheel 246 includes a body 247 having a rounded edge 248. The worm wheel 246 is a structural component for guiding movement of the prosthetic finger digit 240. The contour of the rounded edge 248 may provide a guide path for advancement of the prosthetic finger digit 240 along the rounded edge 248 along the two directions indicated by the geometric reference double-sided arrow 250. Advancement of the prosthetic finger digit 240 causes rotation about a hole 249 of the worm wheel 246. The rotation may be in two directions, as indicated by the geometric reference double-sided arrow 263. The hole 249 is configured to receive a pivot pin 262 therein, as described herein, to facilitate rotation. The rounded edge 248 includes a series of teeth (not shown) configured to engage with a worm gear helix 258, as described herein, that guide the prosthetic finger digit 240 along the rounded edge 248.

The prosthetic finger digit 240 includes a gearbox 252. The gearbox 252 is removed for clarity in FIG. 4B. The gearbox 252 is rotatably attached to the finger knuckle assembly 244 and worm wheel 246 via the pivot pin 262. The gearbox 252 contains various actuation devices and accessories for moving the prosthetic finger digit 240. The gearbox 252 includes a motor 254, motor bearing 256 and worm gear 257. The motor 254 actuates to cause the rotation of the prosthetic finger digit 240 about the pivot pin 262. The motor 254 may be a variety of suitable motors, including electric, brushless, etc. The motor bearing 256 is contacted on the distal side by the motor 254 and on the proximal side by the worm gear 257. The proximal end of the worm gear 257 contacts a worm bearing 260. The motor 254 causes the worm gear 257 to rotate. As the worm gear 257 rotates, a helix 258 of the worm gear 257 engages with the teeth of the worm wheel 246. Engagement of the helix 258 causes the worm gear 257 to advance along the rounded edge 248 of the worm wheel 246, causing the gearbox 252 portion of the prosthetic finger digit 240 to rotate about the pivot pin 262 in a first direction indicated by the arrow 263. The motor 254 can be reversed to cause rotation of the prosthetic finger digit 240 to rotate about the pivot pin 262 in a second direction indicated by the arrow 263 that is opposite the first direction. There may be no axial play between the motor bearing 256, the helix 258, the worm gear 257, the worm bearing 260 and/or the motor 254 when assembled together as shown.

The prosthetic finger digit 240 includes a fairing 264 attached to the prosthetic finger digit 240 that covers part of the gearbox 252. The fairing 264 may be moveable or stationary. The fairing 264 may be rotatably connected, for example with the pivot pin 262. A knuckle cap thinner 266 is attached to a distal end of the gearbox 252. The knuckle cap thinner 266 extends in the distal direction and is rotatably connected to a retaining tab thinner 268.

The retaining tab thinner 268 can rotate relative to the knuckle cap thinner 266 in the two opposite directions indicated by the double-sided arrow 269. Rotation of the retaining tab thinner 268 may be passive, for example caused by rotation of the gearbox 252 about the pivot pin 262. In some embodiments, the wire 265 (shown in FIG. 4C) connects to portions of the prosthetic finger 240 located distally of the knuckle cap thinner 266, for example to the retaining tab thinner 268. The wire 246 extends from one or more proximal portions of the prosthetic finger 240, such as the worm wheel 246 as shown, to one or more distal portions of the prosthetic finger 240, such as the gearbox 252 and retaining tab thinner 268, and/or the fingertip assembly 270. The wire 246 may extend along or around one or more hinge points as shown. The wire 246 may be generally inelastic. The wire 246 may be a nylon monofilament cable, such as gorilla wire. Rotation of the gearbox 252 about the pivot pin 262 may pull on, e.g. increase tension in, the wire 265 thus pulling on the retaining tab thinner 268 and/or the fingertip assembly 270 and causing the retaining tab thinner 268 and fingertip assembly 270 to rotate in a first direction indicated by the arrow 269 such that the prosthetic finger digit 240 closes. By "closes" it is meant that the prosthetic finger 240 as oriented in FIG. 4B rotates at least partially in the counterclockwise directions at the arrows 262 and 269. As oriented in FIG. 4C, closing of the prosthetic finger 240 is rotation in the clockwise direction. Closing the prosthetic finger 240 may pull on and expand the spring 267 (shown in FIG. 4C), thus providing an opening force that acts against the closing force provided by the wire 265. The spring 267 may be a tension spring, coil spring, or other suitable types of springs. The spring 267 may provide a compressive force when expanded. Rotation of the gearbox 252 about the pivot pin 262 may provide more slack to, e.g. decrease tension in, the wire 265 allowing the spring 267 to pull on the retaining tab thinner 268 to rotate the retaining tab thinner 268 in a second direction indicated by the arrow 269 that is opposite to the first direction such that the prosthetic finger digit 240 opens. By "opens" it is meant that the prosthetic finger 240 as oriented in FIG. 4B rotates in the clockwise directions at the arrows 262 and 269. As oriented in FIG. 4C, opening of the prosthetic finger 240 is rotation in the counterclockwise direction. Thus, "closed" and "opened" here refer to their ordinary meaning of a natural hand being opened, for example with an opened hand with straight fingers, or closed, for example a closed first with curled fingers.

The rotation of the outer segments of the prosthetic finger digit 240, such as the retaining tab thinner 268, may therefore be proportional (e.g. linearly related) to rotation of the inner segments, such as the gearbox 252. In some embodiments, other mechanisms for rotation of the outer segments of the prosthetic finger digit 240 may be implemented. For example, the retaining tab thinner 268 or other segments may be rotated by a separate motor. Thus, the particular configuration and grip formation means of the prosthetic hand 200 described herein are merely some example embodiments, and other suitable configurations and grip formation means may be implemented.

A fingertip assembly 270 is rigidly attached to a distal end of the retaining tab thinner 268. The fingertip assembly 270 includes a finger extension 272 and a fingertip 274. A proximal end of the finger extension 274 is attached to a distal end of the retaining tab thinner 268. A proximal end of the fingertip 274 is attached to a distal end of the finger extension 272. In some embodiments, the elastic member that causes rotation in the directions along arrow 269 may be connected to the fingertip assembly 270.

The rotation of the various segments of the prosthetic finger digit 240 may be performed to form various grips with the prosthetic hand 200. For some grips, the prosthetic finger digits 240 may be rotated different amounts at the respective joints of each prosthetic finger digit 240. For some grips, the prosthetic finger digits 240 may be rotated the same amounts at the respective joints of each prosthetic finger digit 240. For some grips, some of the prosthetic finger digits 240 may be rotated the same amounts while other prosthetic finger digits 240 may be rotated different amounts at the respective joints. For example, the prosthetic hand 200 shown in FIG. 6B has one of the prosthetic finger digits 240 straight while the others are curved. Many other grips are possible. Further details of an example grip formation are described herein, for example with respect to FIGS. 12A-12F. The movement of the prosthetic thumb digit 280 may also contribute to various grip formations.

Figure 5A:
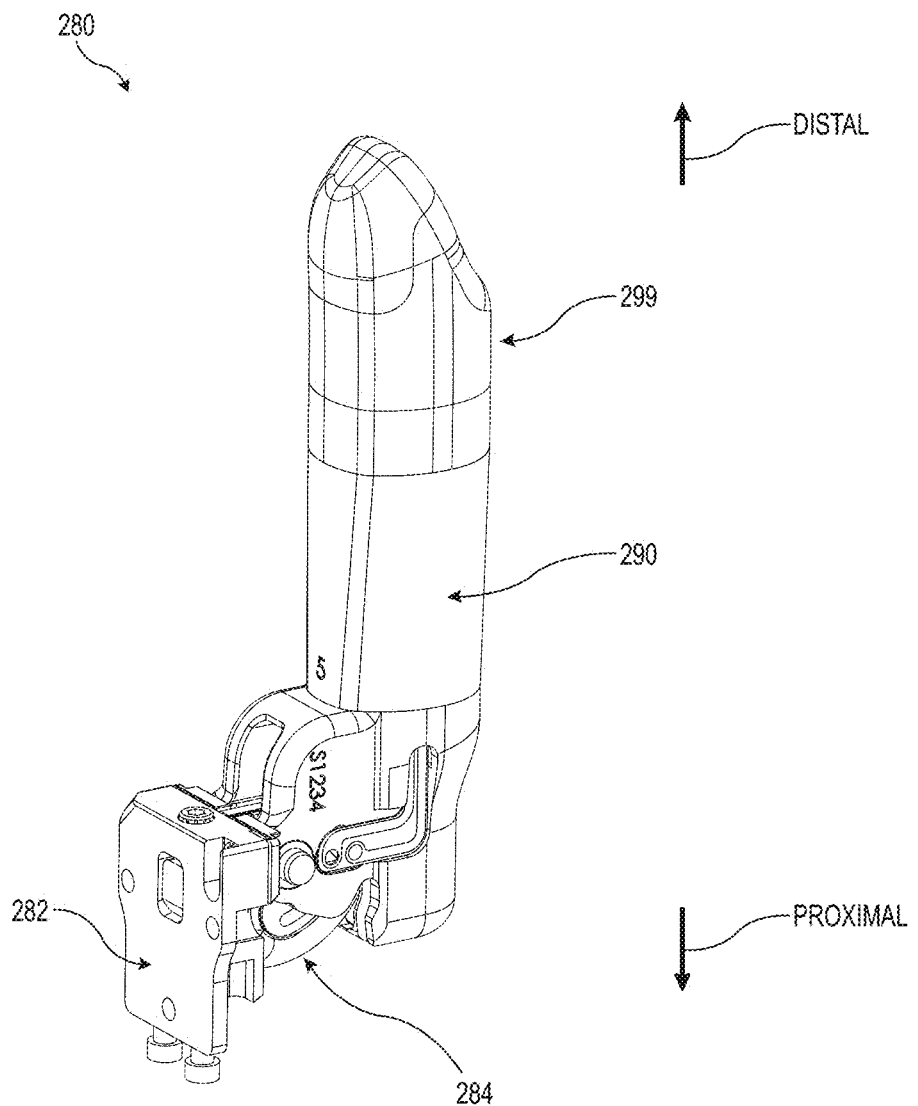
FIG. 5A is a perspective view of a prosthetic thumb digit of the prosthetic hand of FIG. 1.
Figure 5B:
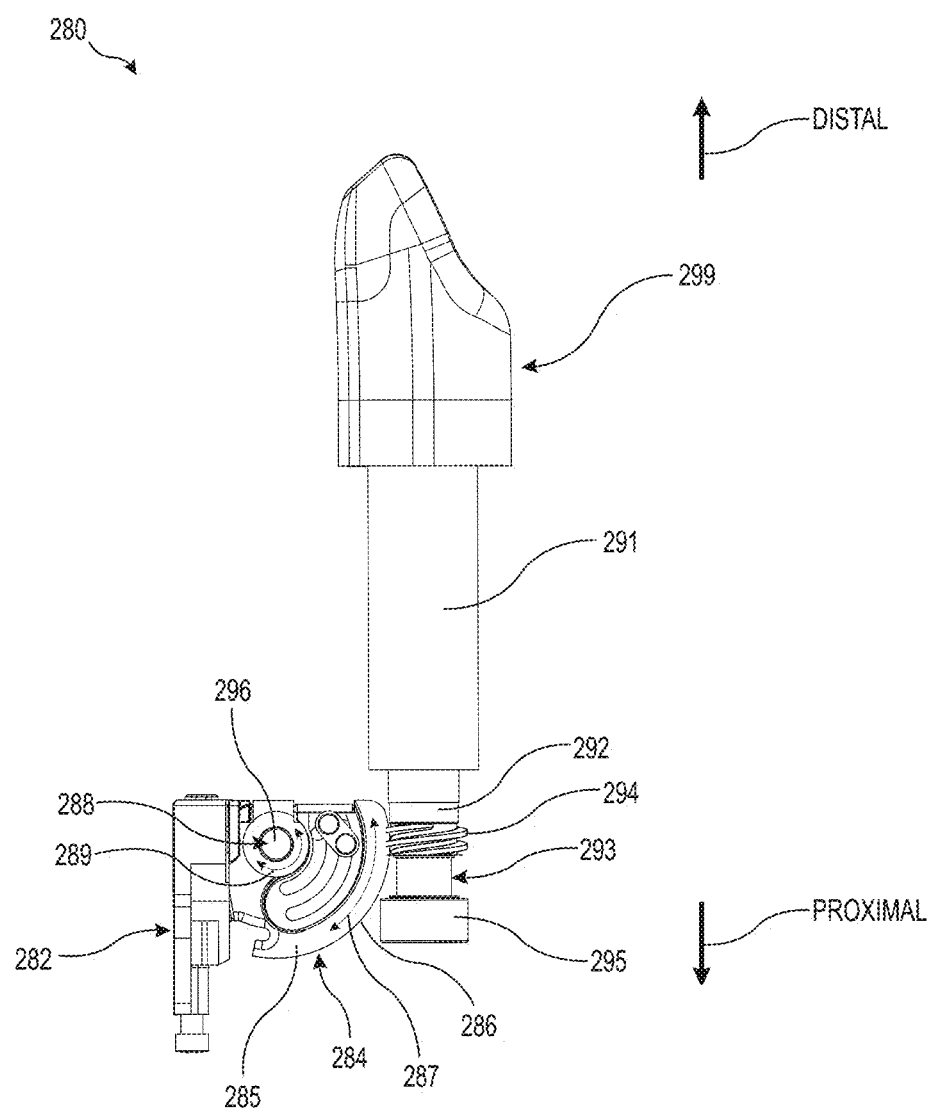
FIG. 5B is a side view of the prosthetic finger digit of FIG. 5A with some components removed for clarity.

FIG. 5A is a perspective view of the prosthetic thumb digit 280. FIG. 5B is a side view of the prosthetic finger digit 280 with some components removed for clarity. The prosthetic thumb digit 280 may be different sizes, for example to accommodate smaller or larger prosthetic hands 200. The following description of the prosthetic thumb digit 280 may apply regardless of these variations in size. The prosthetic thumb digit 280 and components thereof may be formed of plastic, metal, composite, other suitable materials, or combinations thereof.

The prosthetic thumb digit 280 includes a thumb knuckle assembly 282. The thumb knuckle assembly 282 is a structural attachment for connecting the prosthetic thumb digit 280 to the prosthetic hand 200, for example to the hand chassis 214. A worm wheel 284 is attached to the thumb knuckle assembly 282. The worm wheel 284 includes a body 285 having a rounded edge 286. The worm wheel 284 is a structural component for guiding movement of the prosthetic thumb digit 280. The contour of the rounded edge 286 may provide a guide path for advancement of the prosthetic thumb digit 280 along the rounded edge 286 along the two directions indicated by the geometric reference double-sided arrow 287. Advancement of the prosthetic thumb digit 280 causes rotation about a hole 288 of the worm wheel 284. The rotation may be in two directions, as indicated by the geometric reference double-sided arrow 289. The hole 288 is configured to receive a pivot pin 296 therein, as described herein, to facilitate rotation. The rounded edge 286 includes a series of teeth (not shown) configured to engage with a worm gear helix 294, as described herein, that guide the prosthetic thumb digit 280 along the rounded edge 286.

The prosthetic thumb digit 280 includes a gearbox 290. The gearbox 290 is removed for clarity in FIG. 5B. The gearbox 290 is rotatably attached to the thumb knuckle assembly 282 and worm wheel 284 via the pivot pin 296. The gearbox 290 contains various actuation devices and accessories for moving the prosthetic thumb digit 280. The gearbox 252 includes a motor 291, motor bearing 292 and worm gear 293. The motor 291 actuates to cause the rotation of the prosthetic thumb digit 280 about the pivot pin 296. The motor 291 may be a variety of suitable motors, including electric, brushless, etc. The motor bearing 292 is contacted on the distal side by the motor 291 and on the proximal side by the worm gear 293. The proximal end of the worm gear 293 contacts a worm bearing 299. The motor 291 causes the worm gear 293 to rotate. As the worm gear 293 rotates, a helix 294 of the worm gear 293 engages with the teeth of the worm wheel 284. Engagement of the helix 294 causes the worm gear 293 to advance along the rounded edge 286 of the worm wheel 284, causing the gearbox 290 portion of the prosthetic thumb digit 280 to rotate about the pivot pin 296 in a first direction indicated by the arrow 289. The motor 291 can be reversed to cause rotation of the prosthetic thumb digit 280 to rotate about the pivot pin 296 in a second direction indicated by the arrow 289 that is opposite the first direction.

The prosthetic thumb digit 280 includes a thumb fairing 297 and fixed fairing 298 attached to the prosthetic thumb digit 280 that cover part of the gearbox 290. The thumb fairing 297 may be connected to the pivot pin 296. The thumb fairing 297 is moveable, for example rotatable about the pivot pin 296. The fixed fairing 298 may be connected to the palm assembly 212, for example the hand chassis 214. The fixed fairing 298 may be stationary. A thumb tip 299 is attached to a distal end of the gearbox 290. The thumb tip 299 may be rigidly attached to the gearbox 290. In some embodiments, the thumb tip 299 may be moveable, for example rotatable, relative to the gearbox 290.

The prosthetic thumb digit 280 can rotate relative to the palm assembly 212. The prosthetic thumb digit 280 is rotatable in the two directions indicated by the arrow 289. The prosthetic thumb digit 280 is rotatable to "open" and "close" as described above. For example, the prosthetic thumb digit 280 can rotate counterclockwise as oriented in FIG. 5B, for instance when closing the prosthetic thumb digit 280 and/or forming a closed grip with the prosthetic hand 200. For example, the prosthetic thumb digit 280 can rotate clockwise as oriented in FIG. 5B, for instance when opening the prosthetic thumb digit 280 and/or forming an open grip with the prosthetic hand 200.

The rotation of the prosthetic thumb digit 280 may be performed to form various grips with the prosthetic hand 200. For some grips, the prosthetic thumb digit 280 may be rotated the same or different amounts compared to some or all of the prosthetic finger digits 240. Many grips are possible. Further details of an example grip formation are described herein, for example with respect to FIGS. 12A-12F.

FIG. 6A is a perspective view of the prosthetic wrist 100 attached to an embodiment of a prosthetic lower arm 300. The prosthetic lower arm 300 is a prosthetic for the lower or outer segment of an arm, for example the forearm. The prosthetic lower arm 300 is a hollow tube with an arm-like shape. The prosthetic lower arm 300 may have a variety of other suitable shapes and configurations. The proximal end of the prosthetic lower arm 300 attaches to a user, for example to a stump of an amputee, a fitting, socket, etc. The distal end of the prosthetic lower arm 300 attaches to the prosthetic wrist 100. The prosthetic lower arm 300 may be mechanically and/or electrically connected to the prosthetic wrist 100. The prosthetic lower arm 300 receives the prosthetic wrist 100 through an opening at the distal end of the prosthetic lower arm 300. In some embodiments, the prosthetic wrist 100 when attached to the prosthetic lower arm 300 may not be entirely inside the prosthetic lower arm 300. For example, the prosthetic wrist 100 when attached to the prosthetic lower arm 300 may be partially, mostly, or entirely outside the prosthetic lower arm 300. Thus, the example configuration shown of attachment of the prosthetic wrist 100 to the example embodiment of the prosthetic lower arm 300 is merely one possible configuration, and many other suitable configurations may be implemented. Further, the prosthetic wrist 100 can connect to the prosthetic lower arm 300 in a number of suitable manners. For example, the body 102, the actuator module 120, the proximal body 124, the circuit 140, the processor 144, the proximal cover 170, portions thereof, and/or other features of the prosthetic wrist 100 may attach to the prosthetic lower arm 300.

Figure 6B:
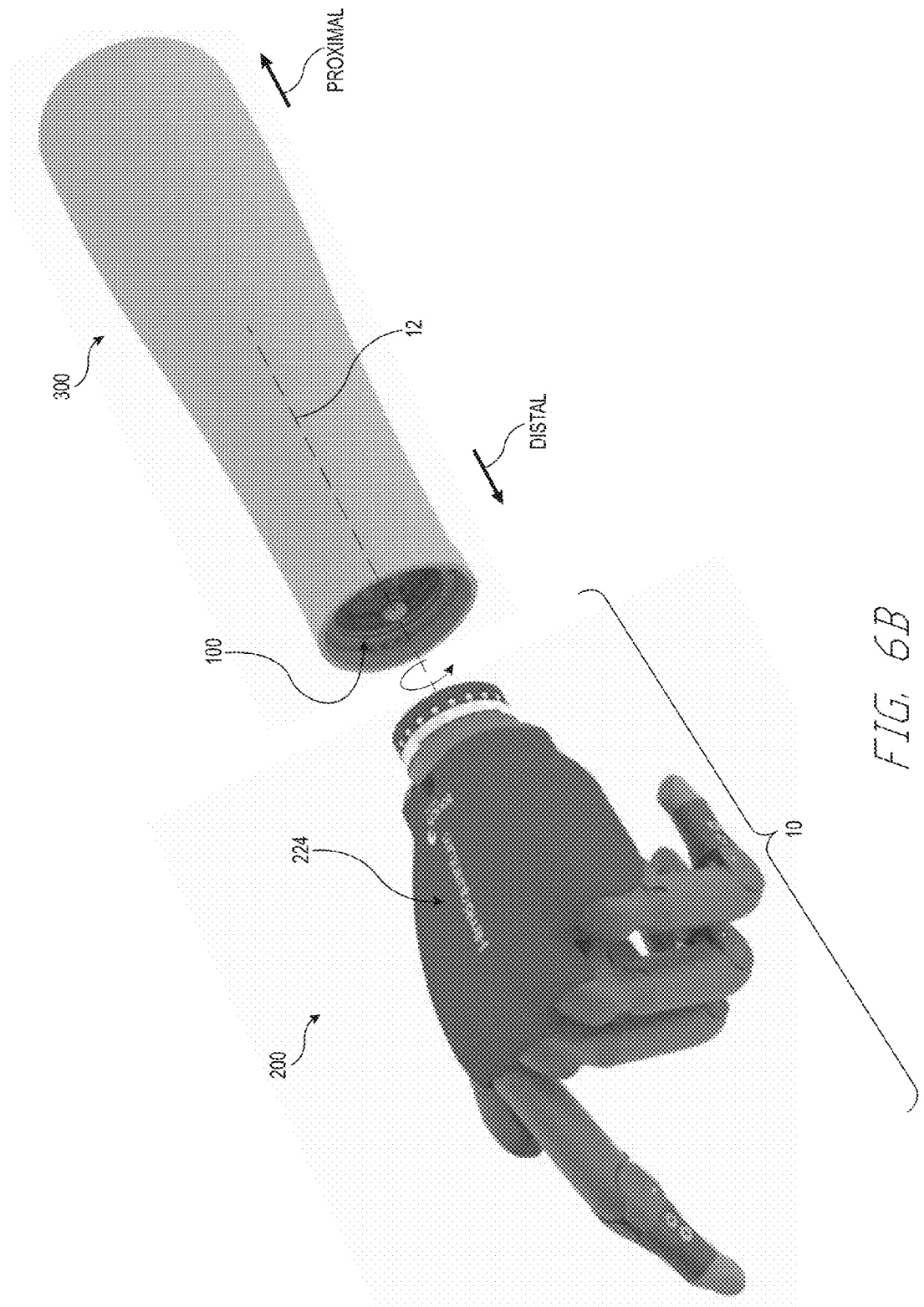
FIG. 6B is a perspective view of the prosthetic wrist and arm of FIG. 6A with the prosthetic hand of FIG. 1 shown detached from the prosthetic wrist.

FIG. 6B is a perspective view of the prosthetic lower arm 300 having the prosthetic wrist 100 installed therein, with the prosthetic hand 200 shown detached from the prosthetic wrist 100. The prosthetic system 10 may therefore be used with the prosthetic lower arm 300. The prosthetic hand 200 may be attached to the prosthetic wrist 100, thereby forming a complete prosthetic lower arm, wrist and hand system. The prosthetic hand 200 may be attached to the prosthetic wrist 100 by moving the prosthetic hand 200 in the proximal direction along the longitudinal axis 12. The prosthetic hand 200 may be detached from the prosthetic wrist 100 by moving the prosthetic hand 200 in the distal direction along the longitudinal axis 12. When attached together, the prosthetic lower arm 300 and prosthetic wrist 100 may be aligned with the longitudinal axis 12, as shown. When attached to the prosthetic wrist 100, the prosthetic hand 200 may rotate about the longitudinal axis 12 as indicated, while the prosthetic lower arm 300 remains rotationally stationary. Thus, the prosthetic hand 200, when attached to the prosthetic wrist 100, may rotate about the longitudinal axis 12 relative to the prosthetic lower arm 300. The rotation of the prosthetic hand 200 is caused by the prosthetic wrist 100, as described herein.

FIG. 6C is a perspective view of the prosthetic wrist 100 attached to the lower arm prosthetic 300. The lower arm prosthetic 300 is transparent for clarity. The lower arm prosthetic 300 includes an electromyography (EMG) system 180. The EMG system 180 is configured to read EMG signals from a user of the prosthetic system 10. The EMG system 180 may be used to control the prosthetic system 10, for example to enter a gesture control mode, as described herein.

The EMG system 180 includes a processor 182 in electrical communication with the prosthetic wrist 100 via one or more wires 184. In some embodiments, the processor 182 may be connected wirelessly to the prosthetic wrist 100. The processor 182 may be connected with the circuit 140 and/or processor 144, or features thereof, of the prosthetic wrist 100. The processor 182 is also connected with one or more EMG sensors 186 via respective wires 188. There are five EMG sensors 186. There may be fewer or more EMG sensors 186. The EMG sensors 186 may be in wireless communication with the processor 182. The EMG sensors 186 may be a variety of different types of EMG sensors, including surface electrodes, intramuscular electrodes, other types, or combinations thereof. The EMG sensors 186 are in electrical communication with a natural limb or portion thereof of a user of the prosthetic system 10. Muscular movements, for example contractions, are detected by the EMG sensors 186. Data associated with the muscle movements are communicated via the processor 180 to the prosthetic wrist 100 and/or to the prosthetic hand 200. Such data is used to enter a gesture control mode, as described herein. The EMG system 180 may also include an IMU. For example, the processor 182 may include or be in communication with an IMU of the lower arm prosthetic 300. The IMU of the lower arm prosthetic 300 may provide orientation data about the lower arm prosthetic 300. The IMU of the lower arm prosthetic 300 may have the same or similar features and/or functionalities as the other IMUs described herein, for example the IMU 230.

Figure 7:
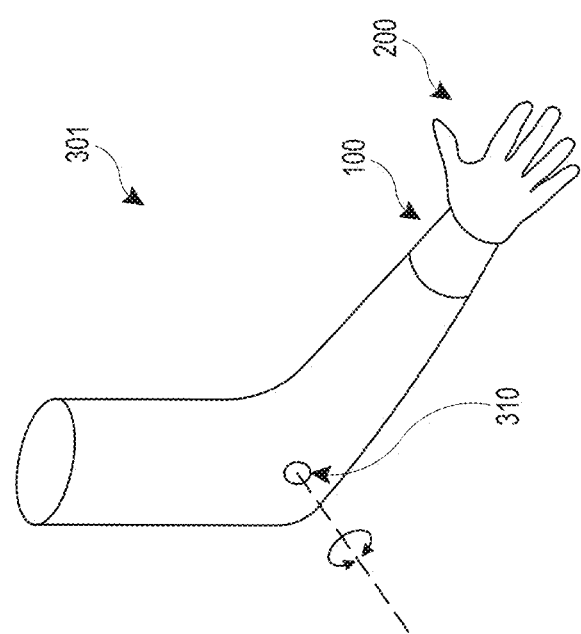
FIG. 7 is a perspective view of an embodiment of a prosthetic arm system incorporating the prosthetic hand and wrist system of FIG. 1.

FIG. 7 is a perspective view of an embodiment of a prosthetic arm 301 attached to the prosthetic system 10. In some embodiments, the prosthetic system 10 may be used with complete prosthetic arms, not just lower prosthetic arm segments as with the lower arm prosthetic 300. A proximal end of the prosthetic arm 301 attaches, directly or indirectly, to an upper arm or shoulder of a user. The opposite, distal end of the prosthetic arm 301 is attached to the prosthetic wrist 100 which is attached to the prosthetic hand 200. The prosthetic arm 301 includes an entire arm, i.e. upper and lower arm segments. In some embodiments, the prosthetic arm 301 may include the lower arm prosthetic 300 as well as an upper arm prosthetic connected thereto. Further, the prosthetic arm 301 may include a rotatable joint, for example an elbow, incorporating an IMU 310. The IMU 310 may have the same or similar features and/or functionalities as the IMU 230 of the prosthetic hand 200. The IMU 310 may detect orientation of the prosthetic arm 301, for example rotational orientation at the elbow. Such orientation data from the IMU 310 may be communicated to the prosthetic wrist 100 and/or prosthetic hand 200 for controlled movement of the prosthetic wrist 100 and/or prosthetic hand 200 in conjunction with, e.g. synchronized with, controlled movement of the prosthetic arm 301. The IMU 310 may be used in addition to the IMU 230 of the prosthetic hand 200. In some embodiments, the IMU 230 may be used for both wrist rotation and movement of the prosthetic arm 301 after a grip has been selected, as described herein. Thus, in some embodiments, a single IMU may perform multiple functions for various prosthetic segments of the system.

Figure 8:
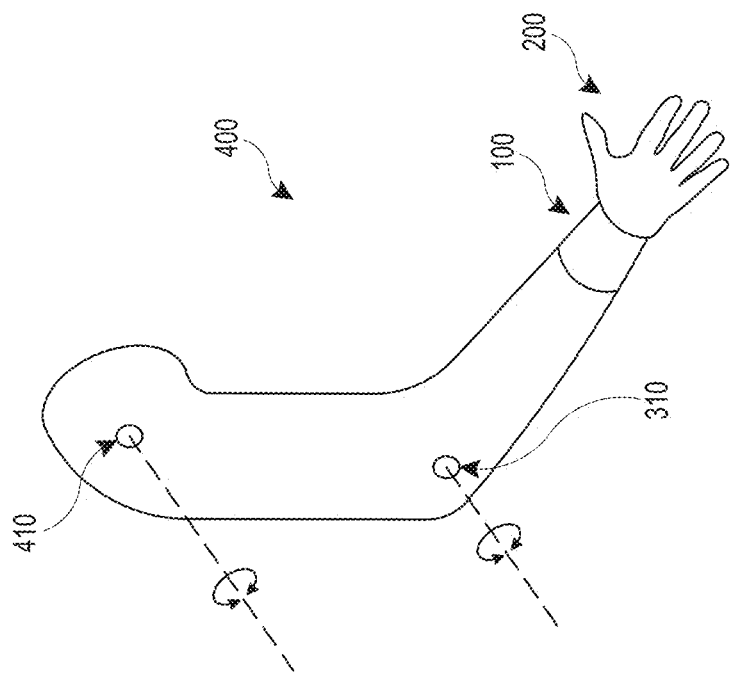
FIG. 8 is a perspective view of an embodiment of a prosthetic shoulder and arm system incorporating the prosthetic hand and wrist system of FIG. 1.

FIG. 8 is a perspective view of an embodiment of a prosthetic arm and shoulder system 400 incorporating the prosthetic system 10. The prosthetic arm and shoulder system 400 attaches, directly or indirectly, to a side of a user. The prosthetic arm and shoulder system 400 is attached to the prosthetic wrist 100 which is attached to the prosthetic hand 200. The prosthetic arm and shoulder system 400 includes an entire arm and shoulder, i.e. upper and lower arm segments and the shoulder. In some embodiments, the prosthetic arm and shoulder system 400 may include the lower arm prosthetic 300 as well as an upper arm prosthetic and shoulder prosthetic. Further, the prosthetic arm and shoulder system 400 may include one or more rotatable joints. The prosthetic arm and shoulder system 400 may include a rotatable elbow joint incorporating the IMU 310. The prosthetic arm and shoulder system 400 may also include a rotatable shoulder joint incorporating an IMU 410. The IMU 410 may have the same or similar features and/or functionalities as the IMU 310 described herein. The IMU 410 may detect orientation of the prosthetic arm and shoulder system 400, for example rotational orientation at the shoulder. Orientation data from the IMU 310 and the IMU 410 may be communicated to the prosthetic wrist 100 and/or prosthetic hand 200 for controlled movement of the prosthetic wrist 100 and/or prosthetic hand 200 in conjunction with, e.g. synchronized with, controlled movement of the prosthetic arm and shoulder system 400. The IMU 310 and IMU 410 may be used in addition to the IMU 230 of the prosthetic hand 200. In some embodiments, the IMU 230 may be used for both wrist rotation and movement of the prosthetic arm 401 after a grip has been selected, as described herein. Thus, in some embodiments, a single IMU may perform multiple functions for various prosthetic segments of the system.

FIG. 9 is a flowchart showing an embodiment of a method 500 for operating the prosthetic wrist 100. The method 500 may be performed by the prosthetic system 10 that includes the prosthetic wrist 100 and prosthetic hand 200. The method 500 may be performed by other prosthetic systems that use an IMU sensor to detect an orientation of a prosthetic to determine wrist rotation. The method 500 may be performed by the prosthetic wrist 100 and in combination with an IMU associated with the prosthetic hand 200, the prosthetic lower arm 300, the prosthetic arm 301, or the prosthetic arm and shoulder system 400. Therefore, the method 500 may be performed by the prosthetic wrist 100

The method 500 begins with step 501 wherein IMU data associated with the orientation of a prosthetic is received. The IMU data received in step 501 may be raw IMU measurements, or calculated results based thereon, such as Euler angles. In step 501, the IMU data is received from the IMU 230 and is associated with the orientation of the prosthetic hand 200. In some embodiments, in step 501 the IMU data is received from the IMU 310 and is associated with the orientation of the prosthetic arm 301. In some embodiments, in step 501 the IMU data is received from the IMUs 310 and/or 410 and is associated with the orientation of the prosthetic arm system 400. In step 501, the IMU data is received by the prosthetic wrist 100, for example by the processor 144, the circuit 140, or communications modules thereof. The IMU data in step 501 may be received by wire, for example via the coaxial assembly 160. The IMU data in step 501 may be received wirelessly, for example via BLUETOOTH®, WiFi, or other suitable connections.

The method 500 then moves to step 502 wherein a desired hand grip is identified. The desired hand grip in step 502 may be identified based on one or more gestures performed by the user. For example, in step 502 a user may perform a translation of the prosthetic hand 200, the IMU 230 may detect the movement, and the processor 144 or 233 may determine that the translation satisfies a movement threshold and identify the desired grip based on the specific movement detected. Instead of or in addition to a translation, in some embodiments of step 502 the user may perform a non-linear movement, such as a rotation of the prosthetic hand 200, a sweeping movement of the prosthetic hand 200 along a non-linear path, etc. Further details of entering a gesture control mode and detecting a gesture movement is described herein, for example with respect to the method 530 of FIG. 9E and the method 540 of FIG. 9F.

In some embodiments, the desired hand grip is identified in step 502 based on receiving a selection of a hand grip from a remote device, such as a mobile phone or wearable. For example, in step 502 the prosthetic hand 200 may communicate the particular gesture to the remote device which may determine the desired grip based thereon and communicate the desired grip back to the prosthetic hand 200. As further example, in step 502 a user may indicate which grip to perform on the remote device, such as a mobile phone or wearable, and the remote device may then communicate the selected desired grip to the prosthetic hand 200. Thus, gesture detection may not be necessary. In some embodiments, the desired hand grip is identified in step 502 based on receiving a selection of a hand grip from a "grip chip," as described herein. The prosthetic hand 200 may form a particular grip when the prosthetic hand 200 is within proximity of a corresponding grip chip. The communication to the prosthetic hand 200 from the remote devices, grip chips, etc. may be via BLUETOOTH®, WiFi, or other suitable connection.

In other embodiments, the desired hand grip may be determined in step 502 in a number of other suitable manners, for example by voice activation, by gesture pattern recognition, cyclic movement, acyclic movement, by EMG signal detection, etc. In some embodiments, the desired hand grip may be determined in step 502 by a combination of these and other means. Some examples of possible approaches to determining the desired hand grip that may be used step 502 are described in U.S. Pat. No. 8,696,763, titled PROSTHETIC APPARATUS AND CONTROL METHOD and issued on Apr. 15, 2014, the entire contents of which are incorporated by reference herein for all purposes.

The method 500 then moves to step 503 wherein the wrist rotation is determined based on the IMU data and on the desired hand grip. The wrist rotation determined in step 503 relates to rotation of the prosthetic wrist 100. In step 503, the wrist rotation is determined by the processor 144. In some embodiments, in step 503 the wrist rotation may be determined by the processor 233. The various other electronic components of the prosthetic wrist 100 and/or prosthetic hand 200 described herein may determine the wrist rotation in step 503.

The wrist rotation is determined in step 503 by analysis of the current orientation of the prosthetic hand 200 based on the IMU data, determination of a target orientation of the prosthetic hand 200 based on the desired hand grip, and comparison of these current and target orientations.

In step 503, the current orientation of the prosthetic hand 200 based on the IMU data is analyzed to determine the Euler angles for the current orientation of the prosthetic hand 200. The IMU data received in step 501 is analyzed in step 503 by the processor 144 and/or 233. Other electronic components of the prosthetic hand 200 and/or prosthetic wrist 100 may perform the analysis. In some embodiments, in step 503 processors of other prosthetic components may perform the analysis, such as processors of the prosthetic lower arm 300, the prosthetic arm 301, or the prosthetic arm and shoulder system 400. In some embodiments, in step 503 processors of other devices may perform the analysis, such as remote devices like a mobile phone, wearable, etc.

In step 503, a particular target orientation for the prosthetic hand 200 may be required for a given desired hand grip. In some embodiments, a particular orientation or range of orientations for the prosthetic hand 200 is identified for a given desired hand grip. Thus each hand grip of a number of possible hand grips may correlate to a particular orientation of the prosthetic hand 200. The target orientations in step 503 may be indicated by angular positions for the prosthetic hand 200 about one axis, two axes or three axes. Further details of wrist rotations based on identified hand grips are described herein, for example with respect to FIGS. 12A-12F.

In step 503, the difference between the target and current orientations is analyzed to determine the wrist rotation. The wrist rotation determined in step 503 includes a direction of rotation and an amount of rotation in which to rotate the prosthetic wrist 100. In some embodiments, other parameters of the wrist rotation may be determined in step 503, such as the speed of rotation, the timing of the rotation, etc. Further details of identifying the target orientation, determining the current orientation and determining the wrist rotation based on the target and current orientations of the prosthetic hand 200 are described herein, for example with respect to method 548 of FIG. 9G.

The method 500 then moves to step 504 wherein the prosthetic wrist 100 is rotated. The rotation of the prosthetic wrist 100 in step 504 is performed by an actuator such as the motor 130 causing rotation of the coupling 150 and thus of the prosthetic hand 200 when attached to the prosthetic wrist 100, as described herein. The prosthetic wrist 100 may rotate in step 504 at a variety of speeds and in a variety of directions. In some embodiments, the prosthetic wrist 100 rotates clockwise or counterclockwise about the longitudinal axis 12. In step 504, the prosthetic wrist 100 may be rotated about roll, pitch and/or yaw axes, as described herein.

Figure 9A:
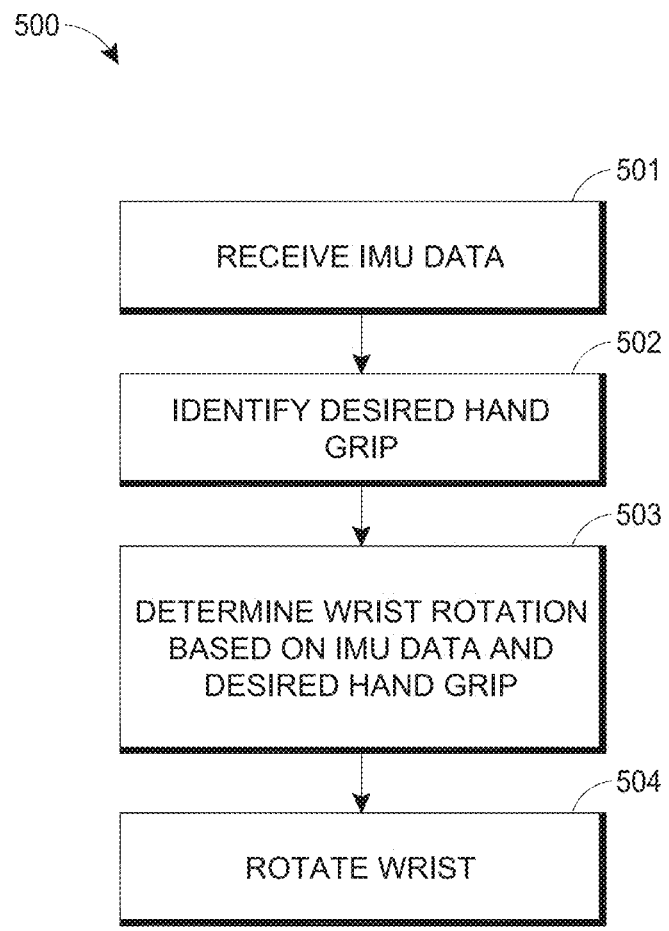
FIG. 9A is a flowchart showing an embodiment of a method for using the prosthetic hand and wrist system of FIG. 1.
Figure 9B:
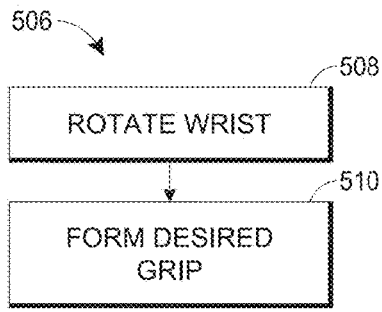
FIGS. 9B-9G are flowcharts showing embodiments of methods that may be used in combination with the method of FIG. 9A.
Figure 9C:
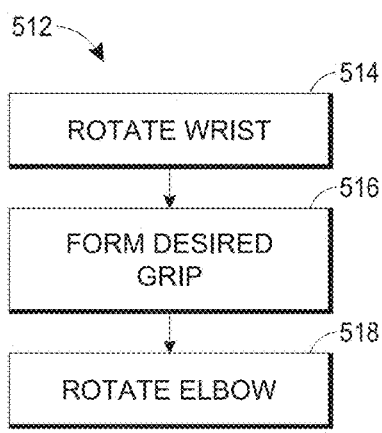
Figure 9D:
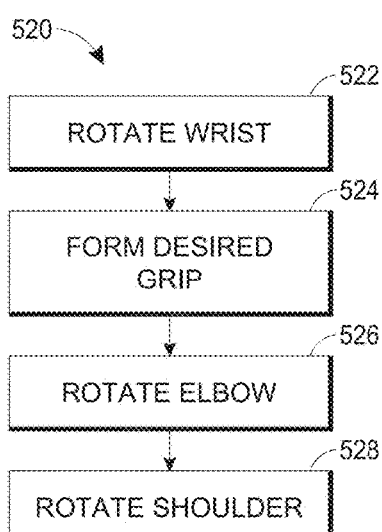

FIGS. 9B-9G are flowcharts showing embodiments of methods that may be used in combination with the method 500 for rotation of the prosthetic wrist 100. FIGS. 9B-9D relate to methods of rotating various prosthetic joints in addition to prosthetic wrists that may be used in combination with the method 500.

FIG. 9B is a flowchart showing an embodiment of a method 506 for forming a desired grip with the prosthetic hand 200 in combination with rotation of the prosthetic wrist 100. The method 506 begins with step 508 wherein the wrist is rotated. Step 508 may perform the steps of the method 500.

The method 506 then moves to step 510 wherein the desired grip is formed with the prosthetic hand 200. The desired grip may be formed in step 510 by moving the prosthetic finger digits 240 and prosthetic thumb digit 280 of the prosthetic hand 200. For example, in step 510 the motors 254 may cause respective prosthetic finger digits 240 to actuate and/or the motor 291 may cause the prosthetic thumb digit 280 to actuate, as described herein. Only some of the prosthetic finger digits 240 may actuate in step 510. Other examples of possible approaches to performing the desired hand grip that may be used step 510 are described in U.S. Pat. No. 8,696,763, titled PROSTHETIC APPARATUS AND CONTROL METHOD and issued on Apr. 15, 2014, the entire contents of which are incorporated by reference herein for all purposes.

Step 510 is performed as step 508 is performed. The prosthetic wrist 100 is thus rotated at the same time that the desired grip is formed with the prosthetic hand 200. Steps 510 and 508 are thus performed "simultaneously." "Simultaneously" as used herein includes its ordinary and usual meaning and includes, for example, at least part of one step is performed at the same time as at least part of another step. For example, in some embodiments, steps 510 and 508 begin at the same time and end at the same time. As further example, in some embodiments, steps 510 and 508 begin at the same time and end at different times. As further example, in some embodiments, steps 510 and 508 begin at different times and end at the same time. The steps 510 and 508 may not be performed simultaneously. For example, in some embodiments, step 508 is performed and then step 510 is performed, or vice versa. For example, the prosthetic wrist 200 may rotate after the prosthetic hand 100 forms the desired grip, or vice versa.

FIG. 9C is a flowchart showing an embodiment of a method 512 for forming a desired grip with the prosthetic hand 200 in combination with rotation of the prosthetic wrist 100 and rotation of a prosthetic elbow. The method 512 begins with step 514 wherein the wrist is rotated. Step 514 may perform the steps of the method 500, described herein. The method 512 then moves to step 516 wherein the desired grip is formed with the prosthetic hand 200. Step 516 is the same as step 510 of the method 506, described herein. The method then moves to step 518 wherein the elbow is rotated. The prosthetic elbow rotated in step 518 may be part of the prosthetic lower arm 301. In step 518 the prosthetic lower arm 301 may thus be rotated, as described herein. The prosthetic lower arm 301 may be rotated based on IMU data received by one or more IMU sensors, such as the IMU 230 and/or the IMU 310. Steps 514, 516 and 518 are performed simultaneously. In some embodiments, only some or none of the steps 514, 516 and 518 are performed simultaneously. For example, two of the steps 514, 516 and 518 may be performed simultaneously while the third step is performed before or after the other two steps.

FIG. 9D is a flowchart showing an embodiment of a method 520 for forming a desired grip with the prosthetic hand 200 in combination with rotation of the prosthetic wrist 100 and rotation of a prosthetic elbow and shoulder. The method 520 begins with step 522 wherein the wrist is rotated. Step 522 may perform the steps of the method 500, described herein. The method 520 then moves to step 524 wherein the desired grip is formed with the prosthetic hand 200. Step 524 is the same as step 510 of the method 506, described herein. The method then moves to step 526 wherein the elbow is rotated. Step 526 may be the same as step 518 of the method 512, described herein. In some embodiments, step 526 is similar to step 518 of the method 512 but includes rotation of the elbow joint of the prosthetic arm and shoulder system 400. The method then moves to step 528 wherein the prosthetic shoulder is rotated. The prosthetic shoulder rotated in step 528 may be part of the prosthetic arm and shoulder system 400. In step 528 the prosthetic arm and shoulder system 400 may thus be rotated, as described herein. The prosthetic arm and shoulder system 400 may be rotated based on IMU data received by one or more IMU sensors, such as the IMU 230, the IMU 310 and/or the IMU 410. Steps 522, 524, 526 and 528 are performed simultaneously. In some embodiments, only some or none of the steps 522, 524, 526 and 528 are performed simultaneously. For example, two of the steps 522, 524, 526 and 528 may be performed simultaneously while the other two steps are performed before or after the first two simultaneous steps. As further example, three of the steps 522, 524, 526 and 528 may be performed simultaneously while the remaining step is performed before or after the first three simultaneous steps.

Figure 9E:
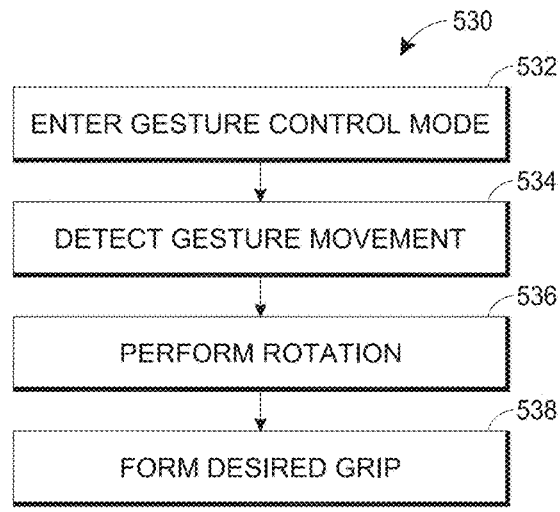

FIG. 9E is a flowchart of an embodiment of a method 530 of rotating the prosthetic wrist 100 and forming a desired grip with the prosthetic hand 200 using gesture control. The method 530 begins with 532 wherein a gesture control mode is entered. The gesture control mode may be entered in step 532 as described with respect to the method 540 in FIG. 9F. The gesture control mode may be entered in step 532 as described with respect to step 502 of the method 500 in FIG. 9A. Examples of possible approaches to entering a gesture control mode that may be used step 532 are described in U.S. Pat. No. 8,696,763, titled PROSTHETIC APPARATUS AND CONTROL METHOD and issued on Apr. 15, 2014, the entire contents of which are incorporated by reference herein for all purposes. The step 502 may incorporate some or all of the steps of the method 540, described with respect to FIG. 9F.

The method 530 then moves to step 534 wherein a gesture movement is detected and analyzed. The gesture movement in step 534 may be detected as described with respect to step 502 of the method 500 in FIG. 9A. In step 534, the IMU 230 of the prosthetic hand 100 detects user movements, for example translations, rotations, vibrations, etc., of the prosthetic hand 100. In some embodiments, in step 534 the prosthetic hand 100 may be moved in the north, south, east, west, up or down directions, or combinations thereof, as described with respect to and shown in FIG. 12A. Examples of possible approaches to detecting a gesture movement that may be used step 534 are described in U.S. Pat. No. 8,696,763, titled PROSTHETIC APPARATUS AND CONTROL METHOD and issued on Apr. 15, 2014, the entire contents of which are incorporated by reference herein for all purposes.

The gesture movement may be analyzed in step 534 to determine if a gesture movement threshold was satisfied. In some embodiments of step 534, the gesture movement may be analyzed over a set period of time, for example every 1,000 milliseconds (ms). If the gesture movement threshold is satisfied within the period of time, the grip is affected. Otherwise, the process times out and returns to waiting for a trigger or indication to enter gesture control mode again.

In some embodiments of step 544, an acceleration threshold may be implemented. For example, the threshold may be an acceleration meeting or exceeding a particular amount in a particular direction, for instance along a particular axis. In some embodiments, two axes are used, such that an acceleration satisfying the acceleration threshold in either direction along either of the two axes satisfies the threshold. The two axes may be the North-South axis and East-West axis indicated in FIG. 12A. If accelerations satisfying the acceleration threshold are detected along both axes, then the larger acceleration may be used to determine the gesture movement. The threshold acceleration amount may be within a range of about 1.05 g to 1.3 g. The threshold acceleration amount may be between a range of about 1.1 g to 1.2 g. The threshold acceleration amount may be about 1.1 g. The threshold acceleration amount may be 1.1 g.

The method 530 then moves to step 536 wherein one or more rotations are performed. In step 536, the prosthetic wrist 100 rotates. In some embodiments, in step 536 the prosthetic arm 301 and/or prosthetic arm and shoulder system 400 also rotate. The rotations of these prosthetics in step 536 may be as described herein, for example with respect to the steps 522, 526 and 528 of the method 520 in FIG. 9D.

The method 530 then moves to step 538 wherein the desired grip is formed with the prosthetic hand 200. The desired grip may be formed in step 528 as described herein, for example, with respect to step 510 of the method 506 in FIG. 9B.

Figure 9F:
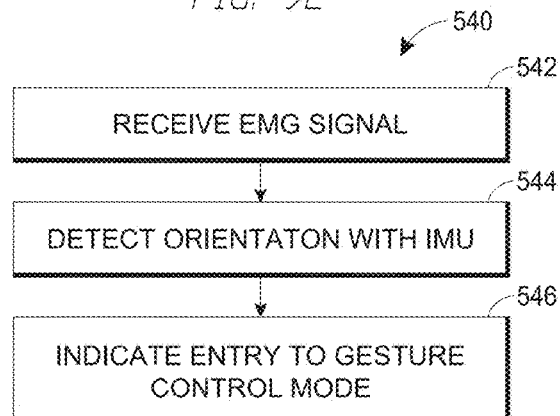

FIG. 9F is a flowchart showing an embodiment of a method 540 for entering gesture control mode. The method 540 may be incorporated into the step 532 of the method 530. The method 540 begins with step 542 wherein an EMG signal is received. The EMG signal is generated in step 542 by the muscle of a user. For example, in step 542 a user may perform a pre-determined muscle movement, such as a co-contraction or hold-open movement, to generate a corresponding EMG signal. The EMG signal may be received in step 542 from the EMG sensors 186 of the EMG system 180. In step 542, data associated with the detected EMG signal may be transmitted to the processor 182 of the EMG system 180 and/or the processor 144 of the prosthetic wrist 100 and/or the processor 233 of the prosthetic hand 200. The data associated with the EMG signal is analyzed in step 542 by one of the various processors and determined to be associated with entering a gesture control mode.

The method 540 then moves to step 544 wherein the orientation of a prosthetic is determined with one or more IMUs. In step 544, the orientation of the prosthetic hand 200 may be determined by the IMU 230 or by another IMU of the prosthetic hand 200. The processor 144 may command the IMU 230 to detect the orientation based on receiving the EMG signal in step 542. In some embodiments, the orientation of the prosthetic arm 301 is detected by the IMU 310, and/or the orientation of the prosthetic arm and shoulder system 401 is detected by the IMU 310 and/or the IMU 410.

In some embodiments of step 544, the orientation of the prosthetic is determined after a settling period. For example a chip, such as the processor 233, may settle for a first period of time to determine any necessary offsets. In some embodiments, the settling period may be from about 10 to 100 milliseconds (ms). In some embodiments, the settling period time may be about 40 ms. In some embodiments, the settling period time may be 40 ms. After the settling period, the Euler angles may be calculated over a calculation period. In some embodiments, the calculation period may be from about 10 to 100 ms. In some embodiments, the calculation period may be about 40 ms. In some embodiments, the calculation period may be 40 ms. An average of the Euler angles calculated during the calculation period may be determined as the orientation.

The determined orientation may be analyzed in step 544 to determine if an orientation threshold was satisfied. The orientation threshold may be indicative of various desirable prosthetic hand 200 positions for entering gesture control mode, such as palm up, palm down, thumb up, or parallel to the ground.

The method 540 then moves to step 546 wherein entry to gesture control mode is indicated. Indication may be provided in step 546 by movement of one or more of the prosthetic finger digits 240 and/or the prosthetic thumb digit 280. In some embodiments, a particular prosthetic finger digit 240, for example the forefinger, will twitch. A twitch may be a slight rotation in a first direction and then a slight rotation in the opposite direction.

The methods 530 and 540 may be combined to combine gesture control mode with rotation of the prosthetic wrist 100 and formation of the desired grip of the prosthetic hand 200. In some embodiments, pitch and roll axes may be used with particular parameters. Example parameters for such embodiments are provided in Tables 1, 2 and 3 below.

TABLE 1

Example gesture control parameters for an extra small left prosthetic hand 200.

| Hand size | XS | | | | Left |
|---|---|---|---|---|---|
| check pitch | | −0.4 ... 0.4 | | | other |
| pointing = | | horizontal | | | down or up |
| check roll | −1 ... +1 | <−2.1 or >+2.1 | <−1.25 | >=−1.25 | reject |
| orientation = | palm up | palm down | pinky up | thumb up | |
| angle = | 90 + pitch | pitch − 90 | reject | 90 − roll | |

TABLE 2

Example gesture control parameters for an extra small right prosthetic hand 200.

| Hand size | XS | | | | Right |
|---|---|---|---|---|---|
| check pitch pointing = | | −0.4 . . . 0.4 horizontal | | | other down or up |
| check roll orientation = angle = | −1 . . . +1 palm up 90 + pitch | <−2.1 or >+2.1 palm down pitch − 90 | >1.25 pinky up reject | <=1.25 thumb up 90 − roll | reject |

TABLE 3

Example gesture control parameters for an small, medium and large sizes of left and right prosthetic hands 200.

| Hand size | S/M/L | | | Left/Right | |
|---|---|---|---|---|---|
| check pitch thumb pointing = | | −1.1 . . . 1.1 not thumb up | | >1.25 pinky up reject | other thumb up 90 − pitch |
| check roll orientation = angle = | −0.4 . . . +0.4 palm up 90 + roll | <−2.8 or >+2.8 palm down 90 − roll | other hand pointing down or up reject | | |

Figure 9G:
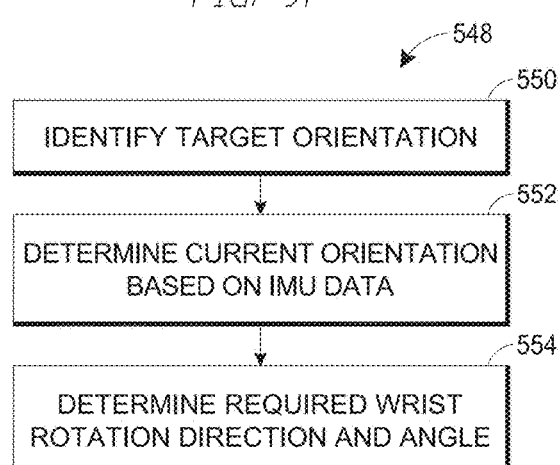

FIG. 9G is a flowchart showing an embodiment of a method 548 for determining the required rotation of the prosthetic wrist 100. The method 548 may be used in step 503 of the method 500 in FIG. 9A. The method 548 begins with step 550 wherein a target orientation for the prosthetic hand 200 is identified. The target orientation may include orientations about one, two or three axes. The target orientation may be determined in step 550 based on the identified desired grip, for example as described in step 502 of the method 500. In step 550, the target orientation may be identified based on a pre-determined relationship between various grips and corresponding wrist orientations. For example, formulas, databases or other means may be used to analyze the relationship. In some embodiments, each grip requires a particular angular orientation of the prosthetic hand 200 about the longitudinal axis 12. In some embodiments, the target orientation is based on that particular angular orientation. In some embodiments, that particular angular orientation is the target orientation. In some embodiments, that particular angular orientation may be modified based on the determined current orientation of the prosthetic hand 200. For example, the prosthetic hand 200 may require multiple rotations, segmented rotations, and the like. Thus, the target orientation may include one or more angular orientations, such as rotation to a first angle and then rotation to a second angle.

The method 548 then moves to step 552 wherein the current orientation of the prosthetic hand 200 is determined based on the IMU data associated with the prosthetic hand 200. The IMU data may be based on detecting the orientation of the prosthetic hand 200 with the IMU 230, as described herein. The orientation of the prosthetic hand 200 may indicate the current rotational position of the prosthetic wrist 100. For example, the prosthetic wrist 100 may have rotated the hand previously, and the current orientation of the prosthetic hand 200 may be indicative of the rotated position of the prosthetic wrist 100. As further example, a user may have manually rotated the prosthetic hand 200, and thus the current orientation of the prosthetic hand 200 may be used to determine the manually rotated position of the prosthetic wrist 100. As further example, a user may have just installed the prosthetic hand 200 onto the prosthetic wrist 100, and thus the current orientation of the prosthetic hand 200 may be used to determine the installed position of the prosthetic wrist 100

The method 548 then moves to step 554 wherein the required wrist rotation direction and angle are determined. The angle is determined in step 554 by comparing the current and target orientations of the prosthetic wrist 100. For example, it may be determined that achieving the target orientation requires a rotation of thirty degrees in the clockwise direction from the current orientation.

Figure 10A:
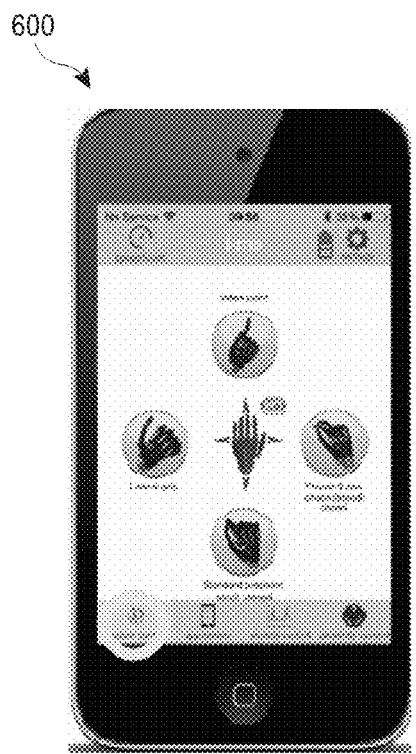
FIGS. 10A-10D are embodiments of remote devices that may be used with the prosthetic hand and wrist system of FIG. 1.
Figure 10B:
Figure 10C:
Figure 10D:

FIGS. 10A-10D are embodiments of remote devices that may be used with the hand and wrist system 10. FIGS. 10A-10C show example embodiments of a mobile device 600 with various screen displays. The mobile device 600 may be used, for example via the touch screen, with grip indicator software, such as apps, to indicate desired grips, which may be based on particular gesture movements. The remote device 600 may include "quick grips" icons that a user can select, for example by touching on the screen, and then via the software the prosthetic hand 200 will move into the programmed grip and the prosthetic wrist 100 will rotate the prosthetic hand 200 to the required position for that specific grip. The remote device 600 may or may not be used with gesture control. The selection of a grip with the remote device 600 may be used in conjunction with the various other prosthetic movements, such as wrist, elbow and/or shoulder rotation. FIG. 10D shows an example embodiment of a wearable device 700 with a screen display. The wearable device 700 may be used, for example via the touch screen, voice activation, etc. to indicate desired grips based on particular gesture movements. The devices 600, 700 may be communicated with via touch, voice control, from other devices, and/or by other suitable means. In some embodiments, both devices 600, 700 may be used in combination with the prosthetic wrist 100 and/or prosthetic hand 100.

Figure 11:
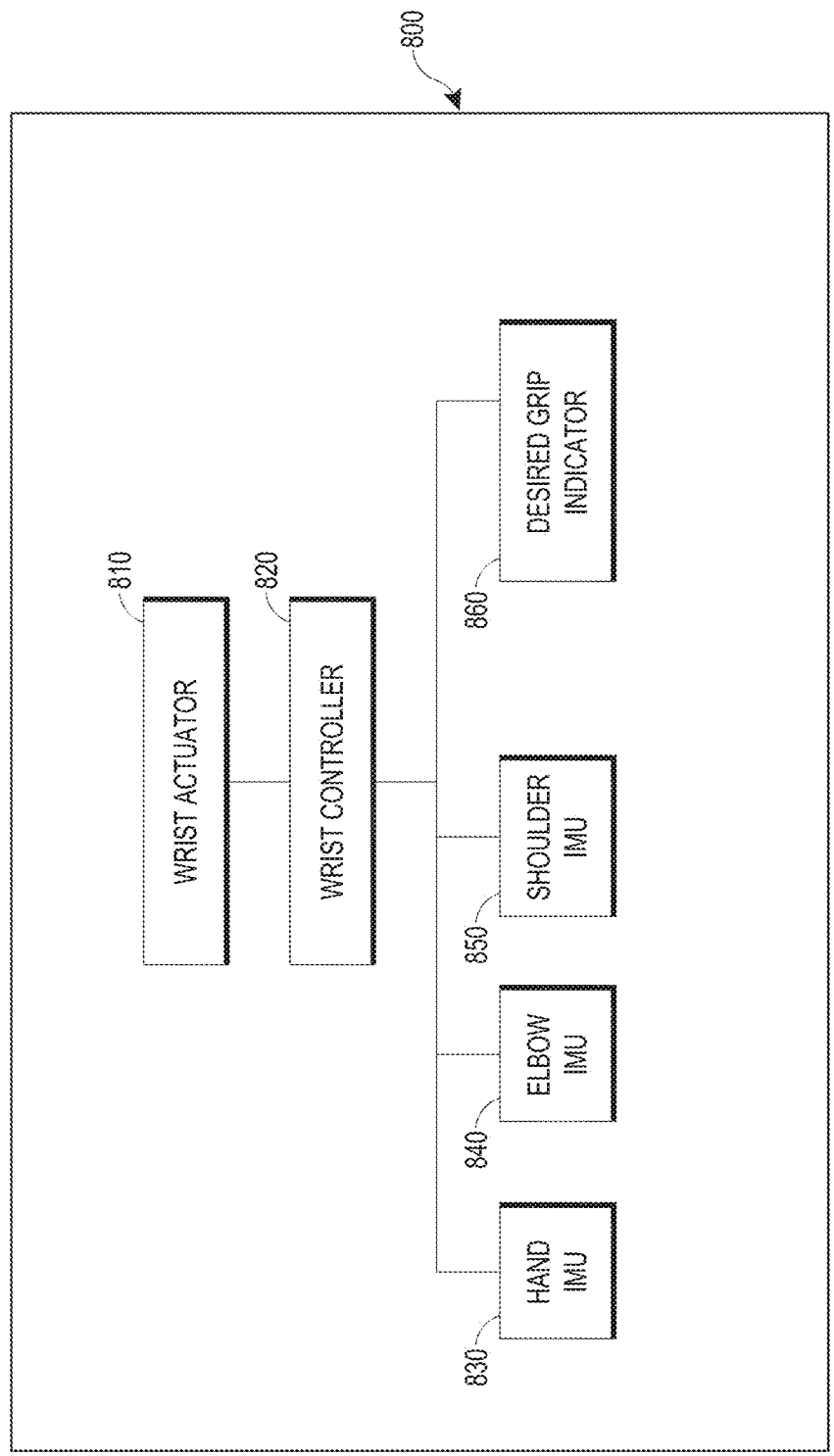
FIG. 11 is an embodiment of a control system that may be used to control the prosthetic hand and wrist system of FIG. 1.

FIG. 11 is an embodiment of a control system 800 that may be used to control the hand and wrist system 10. The control system 800 includes a prosthetic wrist actuator 810 in communicating connection with a prosthetic wrist controller 820. The prosthetic wrist actuator 810 may include the various prosthetic wrist actuators described herein, for example the motor 130 and/or other components of the prosthetic wrist 100. The prosthetic wrist controller 820 may include the various prosthetic wrist control devices described herein, for example the processor 144 or circuit 140 of the prosthetic wrist 100. The prosthetic wrist controller 820 may also be separate from the prosthetic wrist 100, for example it may be part of the prosthetic hand 200, the prosthetic lower arm 300, the prosthetic arm 301, the prosthetic arm and shoulder system 400, the remote devices 600 and/or 700. In some embodiments, the prosthetic wrist controller 820 is distributed among these or other devices. The prosthetic wrist controller 820 may include a number of suitable types of controllers and control techniques, including for example open loop, closed loop, feedback, partial-integrative-derivative (PID), programmable logic controller (PLC), microcontroller, on-off, linear, proportional, non-linear, fuzzy logic, other types, or combinations thereof.

The prosthetic wrist controller 820 receives data from one or more sensors and commands the prosthetic wrist actuator 810 based on the received data. The prosthetic wrist controller 820 is in communicating connection with a prosthetic hand IMU 830, a prosthetic elbow IMU 840, a prosthetic shoulder IMU 850, and a desired grip indicator 860. In some embodiment, the prosthetic wrist controller 820 is in communicating connection with only one or some of these components. In some embodiments, the prosthetic wrist controller 820 is in communicating connection with other components. The prosthetic hand IMU 830, prosthetic elbow IMU 840, prosthetic shoulder IMU 850, and desired grip indicator 860 communicate data, information, signals, etc. to the prosthetic wrist controller 820 for controlling the prosthetic wrist actuator 810.

The prosthetic hand IMU 830, prosthetic elbow IMU 840, and prosthetic shoulder IMU 850 may be any of the various types of IMUs described herein, including for example a nine-axis IMU. The IMUs 830, 840 and 850 may be the same or different type of IMUs. In some embodiments, the IMUs 830, 840 and 850 may be the same IMU. The prosthetic hand IMU 830 may be the IMU 230 of the prosthetic hand 200. In addition or alternatively, in some embodiments the prosthetic hand IMU 830 may include other IMUs of the prosthetic hand 200. The prosthetic elbow IMU 840 may be the IMU 310 of the prosthetic arm 301. In addition or alternatively, in some embodiments the prosthetic elbow IMU 840 may include other IMUs of the prosthetic arm 301. The prosthetic shoulder IMU 850 may be the IMU 410 of the prosthetic arm 400. In addition or alternatively, in some embodiments the prosthetic elbow IMU 850 may include other IMUs of the prosthetic arm 400.

The control system 800 may be used to perform the various methods described herein. In some embodiments, the control system 800 may be used to perform the method 500, the method 506, the method 512, the method 520, the method 530, the method 540 and/or the method 548. The prosthetic wrist controller 820 may receive data from the IMUs 830, 840 and 850 and command the prosthetic wrist actuator 810 to perform the various methods or steps thereof. The control system 800 may also include the prosthetic hand 200 and components thereof, for example to form a desired grip. The prosthetic wrist actuator 810 may be considered to include, for example, the various prosthetic hand motors such as one or more of the prosthetic finger motors 254, the prosthetic thumb motor 291, the motor assembly 220 and thumb rotator 222, etc. The control system 800 may also include the prosthetic lower arm 300, the prosthetic arm 301, and/or the prosthetic arm and shoulder system 401, and components thereof, for example to rotate an arm or receive data therefrom. The prosthetic wrist actuator 810 may be considered to include, for example, various prosthetic arm, elbow, and/or shoulder motors.

The desired grip indicator 860 communicates a desired grip to the prosthetic wrist controller 820. The desired grip indicator 860 may be an EMG system, for example the EMG system 180, and communicate EMG signals or associated data to the prosthetic wrist controller 820. Such signals may be analyzed by the prosthetic wrist controller 820, for example to determine if a gesture control mode should be entered. The desired grip indicator 860 may be or include an IMU that measures a movement of the user, such as a gesture performed by the user to indicate a particular grip, as described herein. The desired grip indicator 860 may be or use the IMUs 830, 840 and/or 850. The desired grip indicator 860 may be a remote device that provides the desired grip, for example the remote devices 600 and/or 700.

FIGS. 12A-12F are sequential perspective views of the prosthetic wrist and arm system 10 showing simultaneous grip formation of the prosthetic hand 200 and rotation with the prosthetic wrist 100. The geometric reference North-South-East-West system is indicated, with perpendicular "up" and "down" directions. The North-South-East-West are in a plane generally aligned with the longitudinal axis 12 (see FIG. 12B) and parallel to the ground. Other orientations of the North-South-East-West system may be implemented. The system 10 may be moved, for example translated, in one of the indicated directions to register an acceleration that satisfies an acceleration threshold, as described herein. The prosthetic system 10 may then perform the grip formation and wrist rotation, as described herein.

The grip formation and wrist rotation may begin such that the system 10 has the configuration as shown in FIG. 12A, with the palm of the prosthetic hand 200 up and generally parallel to the North-South-East-West plane, and the prosthetic finger digits 240A, 240B, 240C and 240D and prosthetic thumb digit 280 extended as shown.

The grip formation and wrist rotation may continue such that the prosthetic system 10 has the configuration as shown in FIG. 12B at a later point in time compared to FIG. 12A. As shown in FIG. 12B, the prosthetic digits 240A, 240B, 240C, 240D, 280 are bent slightly toward the palm fairing 226 in the direction 13 as indicated, and the prosthetic hand 200 has rotated slightly about the longitudinal axis 12 in the direction 14 as indicated, as compared to FIG. 12A. The prosthetic digits 240B, 240C, 240D are bent slightly farther than the prosthetic digit 240A.

The grip formation and wrist rotation may continue such that the prosthetic system 10 has the configuration as shown in FIG. 12C at a later point in time compared to FIG. 12B. As shown in FIG. 12C, the prosthetic digits 240B, 240C, 240D, 280 are bent farther toward the palm fairing 226, and the prosthetic hand 200 has rotated farther about the longitudinal axis 12, as compared to FIG. 12B. The prosthetic digit 240A may have the same curvature as in the FIG. 12B. The prosthetic digits 240B, 240C, 240D are further bent more than the prosthetic digit 240A.

The grip formation and wrist rotation may continue such that the prosthetic system 10 has the configuration as shown in FIG. 12D at a later point in time compared to FIG. 12C. As shown in FIG. 12D, the prosthetic digits 240B, 240C, 240D, 280 are bent farther toward the palm fairing 226, and the prosthetic hand 200 has rotated farther about the longitudinal axis 12, as compared to FIG. 12C. The prosthetic digit 240A may have the same curvature as in the FIG. 12C. The prosthetic digits 240B, 240C, 240D are further bent more than the prosthetic digit 240D.

The grip formation and wrist rotation may continue such that the prosthetic system 10 has the configuration as shown in FIG. 12E at a later point in time compared to FIG. 12D. As shown in FIG. 12E, the prosthetic digits 240B, 240C, 240D, 280 are bent farther toward the palm fairing 226, and the prosthetic hand 200 has rotated farther about the longitudinal axis 12, as compared to FIG. 12D. The prosthetic digit 240A may have the same curvature as in the FIG. 12D. The prosthetic digits 240B, 240C, 240D are further bent more than the prosthetic digit 240A. The dorsal fairing 224 is approximately perpendicular to the North-South-East-West plane.

Figure 12F:
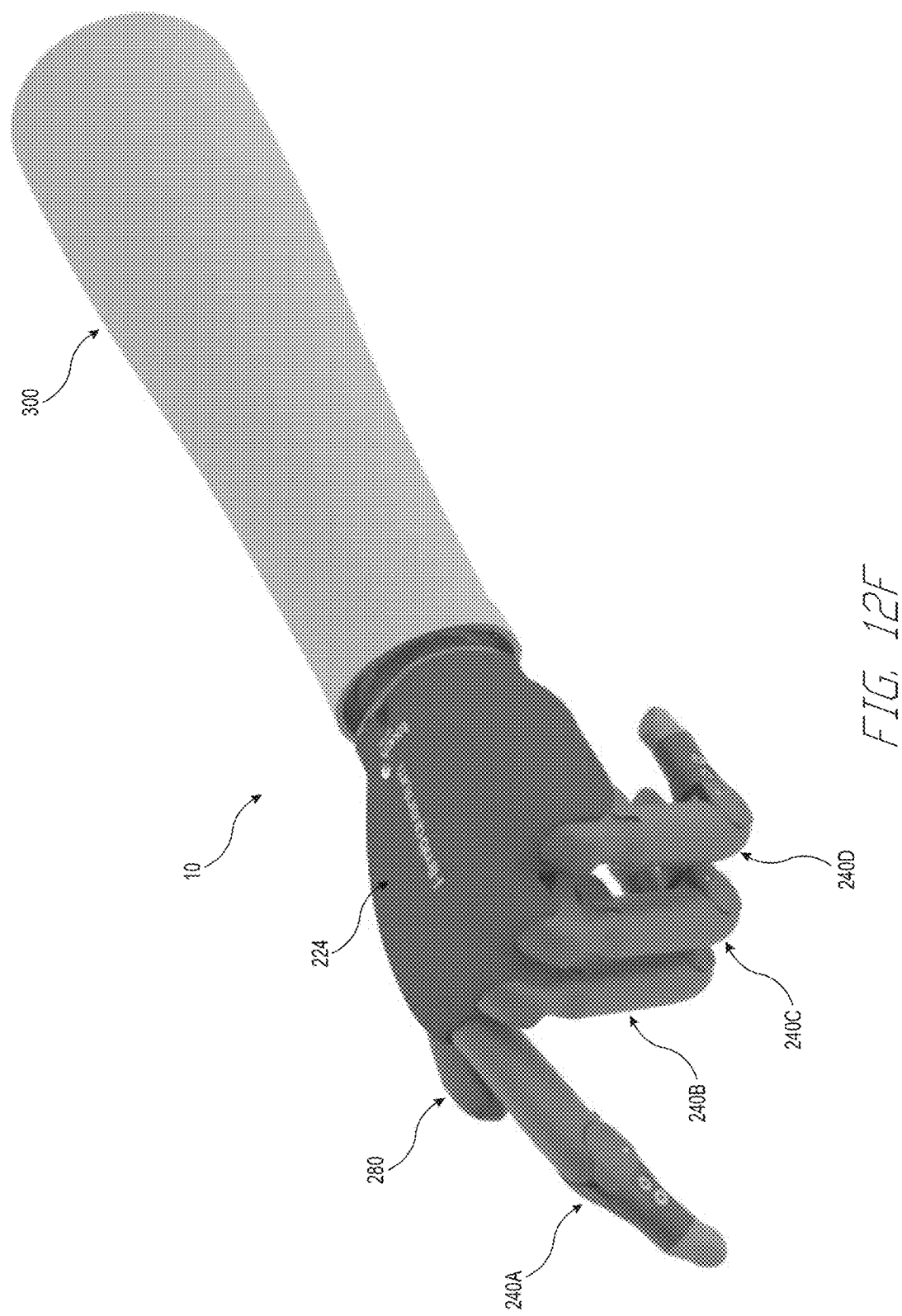

Finally, the grip formation and wrist rotation may end such that the prosthetic system 10 has the configuration as shown in FIG. 12F at a later point in time compared to FIG. 12E. As shown in FIG. 12F, the prosthetic digits 240B, 240C, 240D, 280 are curled completely or mostly toward the palm fairing 226, and the prosthetic hand 200 has rotated farther about the longitudinal axis 12, as compared to FIG. 12E. The prosthetic digit 240A may have the same curvature as in the FIG. 12E. The prosthetic digits 240B, 240C, 240D are further bent more than the prosthetic digit 240A. The dorsal fairing 224 is approximately parallel to the North-South-East-West plane. This is merely one example and a variety of other combinations of wrist rotations and grip formations may be performed with the system 10.

A person/one having ordinary skill in the art would appreciate that any of the various illustrative logical blocks, modules, controllers, means, circuits, and algorithm steps or blocks described in connection with the aspects disclosed herein can be implemented as electronic hardware (e.g., a digital implementation, an analog implementation, or a combination of the two, which can be designed using source coding or some other technique), various forms of program or design code incorporating instructions (which can be referred to herein, for convenience, as "software" or a "software module"), or combinations of both. To clearly illustrate this interchangeability of hardware and software, various illustrative components, blocks, modules, circuits, and steps or blocks have been described above generally in terms of their functionality. Whether such functionality is implemented as hardware or software depends upon the particular application and design constraints imposed on the overall system. Skilled artisans can implement the described functionality in varying ways for each particular application, but such implementation decisions should not be interpreted as causing a departure from the scope of the present disclosure.

A person having ordinary skill in the art would further understand that information and signals can be represented using any of a variety of different technologies and techniques. For example, data, instructions, commands, information, signals, bits, symbols, and chips that can be referenced throughout the above description can be represented by voltages, currents, electromagnetic waves, magnetic fields or particles, optical fields or particles, or any combination thereof.

The various illustrative logical blocks, modules, and circuits described in connection with the aspects disclosed herein and in connection with the figures can be implemented within or performed by an integrated circuit (IC), an access terminal, or an access point. The IC can include a general purpose processor, a digital signal processor (DSP), an application specific integrated circuit (ASIC), a field programmable gate array (FPGA) or other programmable logic device, discrete gate or transistor logic, discrete hardware components, electrical components, optical components, mechanical components, or any combination thereof designed to perform the functions described herein, and can execute codes or instructions that reside within the IC, outside of the IC, or both. The logical blocks, modules, and circuits can include antennas and/or transceivers to communicate with various components within the network or within the device.

A general purpose processor can be a microprocessor, but in the alternative, the processor can be any conventional processor, controller, microcontroller, or state machine. A processor can also be implemented as a combination of computing devices, e.g., a combination of a DSP and a microprocessor, a plurality of microprocessors, one or more microprocessors in conjunction with a DSP core, or any other such configuration. The functionality of the modules can be implemented in some other manner as taught herein. The functionality described herein (e.g., with regard to one or more of the accompanying figures) can correspond in some aspects any similarly designated "means for" functionality in the appended claims.

If implemented in software, the functions can be stored on or transmitted over as one or more instructions or code on a computer-readable medium. The steps or blocks of a methods or algorithms disclosed herein can be implemented in a processor-executable software module which can reside on a computer-readable medium. Computer-readable media includes both computer storage media and communication media including any medium that can be enabled to transfer a computer program from one place to another. A storage media can be any available media that can be accessed by a computer. By way of example, and not limitation, such computer-readable media can include RAM, ROM, EEPROM, CD-ROM or other optical disk storage, magnetic disk storage or other magnetic storage devices, or any other medium that can be used to store desired program code in the form of instructions or data structures and that can be accessed by a computer. Also, any connection can be properly termed a computer-readable medium. Disk and disc, as used herein, includes compact disc (CD), laser disc, optical disc, digital versatile disc (DVD), floppy disk, and Blu-ray disc where disks usually reproduce data magnetically, while discs reproduce data optically with lasers. Combinations of the above should also be included within the scope of computer-readable media. Additionally, the operations of a method or algorithm can reside as one or any combination or set of codes and instructions on a machine readable medium and computer-readable medium, which can be incorporated into a computer program product.

It is understood that any specific order or hierarchy of steps or blocks in any disclosed process is an example of a sample approach. Based upon design preferences, it is understood that the specific order or hierarchy of steps or blocks in the processes can be rearranged while remaining within the scope of the present disclosure. Any accompanying method claims present elements of the various steps or blocks in a sample order, and are not meant to be limited to the specific order or hierarchy presented.

Various modifications to the implementations described in this disclosure can be readily apparent to those skilled in the art, and the generic principles defined herein can be applied to other implementations without departing from the spirit or scope of this disclosure. Thus, the disclosure is not intended to be limited to the implementations shown herein, but is to be accorded the widest scope consistent with the claims, the principles and the novel features disclosed herein. The word "example" is used exclusively herein to mean "serving as an example, instance, or illustration." Any implementation described herein as "example" is not necessarily to be construed as preferred or advantageous over other implementations.

Certain features that are described in this specification in the context of separate implementations also can be implemented in combination in a single implementation. Conversely, various features that are described in the context of a single implementation also can be implemented in multiple implementations separately or in any suitable sub-combination. Moreover, although features can be described above as acting in certain combinations and even initially claimed as such, one or more features from a claimed combination can in some cases be excised from the combination, and the claimed combination can be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing can be advantageous. Moreover, the separation of various system components in the implementations described above should not be understood as requiring such separation in all implementations, and it should be understood that the described program components and systems can generally be integrated together in a single software product or packaged into multiple software products. Additionally, other implementations are within the scope of the following claims. In some cases, the actions recited in the claims can be performed in a different order and still achieve desirable results.

It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

What is claimed is:

1. A prosthetic hand and wrist system, the system comprising:
   a prosthetic hand;
   a prosthetic wrist defining a longitudinal axis and comprising a fixed portion, an actuator module, and a rotatable portion, the fixed portion configured to attach to an arm, the rotatable portion configured to attach to the prosthetic hand, and the actuator module attached to both the fixed and rotatable portions and configured to actuate the rotatable portion relative to the fixed portion thereby rotating the prosthetic hand about the longitudinal axis;
   the prosthetic hand comprising an inertial measurement unit (IMU) configured to detect an orientation of the prosthetic hand in three dimensional space including a rotational position of the prosthetic hand about the longitudinal axis;
   and a processor in communication with the IMU and the actuator module and configured to:
   receive data from the IMU associated with the orientation of the prosthetic hand in three dimensional space including the rotational position of the prosthetic hand about the longitudinal axis,
   identify a desired grip for the prosthetic hand,
   determine a rotation for the prosthetic hand based on only i) the data from the IMU and ii) the desired grip, and
   cause the actuator module to perform the rotation for the prosthetic hand by actuating the rotatable portion.

2. The prosthetic hand and wrist system of claim 1, wherein to identify the desired grip for the prosthetic hand, the processor is further configured to:
   receive an electromyography (EMG) signal from a user of the prosthetic hand and wrist system;
   detect a gesture movement performed by the user, the gesture movement comprising a translation of the prosthetic hand, wherein to detect the gesture movement of the prosthetic hand the processor is further configured to determine that the translation exceeds an acceleration threshold; and
   determine the desired grip based on the detected gesture movement.

3. The prosthetic hand and wrist system of claim 1, wherein to determine the rotation for the prosthetic hand, the processor is further configured to:
   determine Euler angles for the prosthetic hand based on the data from the IMU; and
   determine angular rotation data based on the determined Euler angles and on the desired grip.

4. The prosthetic hand and wrist system of claim 3, wherein the angular rotation data comprises a direction and an angle of rotation.

5. The prosthetic hand and wrist system of claim 1, wherein the processor is further configured to cause the actuator module to form the desired grip simultaneously with rotating the prosthetic hand.

6. The prosthetic hand and wrist system of claim 1, further comprising a distal actuator coupled with a distal portion of the hand, the distal actuator configured to rotate the hand about a pitch axis to form the desired grip with the prosthetic hand.

7. The prosthetic hand and wrist system of claim 1, wherein the actuator module is configured to cause rotation of the prosthetic hand about two or more axes.

8. The prosthetic hand and wrist system of claim 1, wherein the IMU comprises a nine-axis IMU including three accelerometers, three gyroscopes and three magnetometers.

9. The prosthetic hand and wrist system of claim 1, wherein the arm is a prosthetic arm.

10. A prosthetic wrist comprising:
a fixed portion defining a longitudinal axis and configured to attach to a prosthetic or natural arm;
a rotatable portion configured to attach to a prosthetic hand, the prosthetic hand comprising an inertial measurement unit (IMU) configured to detect an orientation of the prosthetic hand in three dimensional space including a rotational position of the prosthetic hand about the longitudinal axis;
an actuator module attached to both the fixed and rotatable portions and configured to actuate the rotatable portion relative to the fixed portion to cause rotation of the prosthetic hand; and a processor configured to:
communicate with the IMU and the actuator module;
receive data from the IMU associated with the orientation of the prosthetic hand in three dimensional space including the rotational position of the prosthetic hand about the longitudinal axis,
identify a desired grip for the prosthetic hand,
determine a rotation for the rotatable portion based on only i) the data from the IMU and ii) the desired grip, and
cause the actuator module to perform the rotation.

11. The prosthetic wrist of claim 10, wherein to identify the desired grip for the prosthetic hand, the processor is further configured to:
receive an electromyography (EMG) signal from a user of the prosthetic wrist;
detect a gesture movement performed by the user; and
determine the desired grip based on the detected gesture movement.

12. The prosthetic wrist of claim 10, wherein to determine the rotation for the prosthetic hand, the processor is further configured to:
determine Euler angles for the prosthetic hand based on the data from the IMU; and
determine angular rotation data based on the determined Euler angles and on the desired grip.

13. The prosthetic wrist of claim 12, wherein the angular rotation data comprises a direction and an angle of rotation.

14. The prosthetic wrist of claim 10, wherein the data from the IMU is associated with the orientation of the prosthetic hand in three-dimensional space.

15. A prosthetic hand and wrist system, the system comprising:
a prosthetic hand;
a prosthetic wrist comprising a fixed portion, an actuator module, and a rotatable portion, the fixed portion configured to attach to an arm, the rotatable portion configured to attach to the prosthetic hand, and the actuator module attached to both the fixed and rotatable portions and configured to actuate the rotatable portion relative to the fixed portion thereby rotating the prosthetic hand;
an inertial measurement unit (IMU) attached to the prosthetic hand and configured to detect an orientation of the prosthetic hand;
and a processor in communication with the IMU and the actuator module and configured to:
receive data from the IMU associated with the orientation of the prosthetic hand,
detect a gesture movement of the prosthetic hand, the gesture movement comprising a translation of the prosthetic hand, wherein to detect the gesture movement of the prosthetic hand the processor is further configured to determine that the translation exceeds an acceleration threshold,
determine a desired grip for the prosthetic hand based on the detected gesture movement,
determine a rotation for the prosthetic hand based on only i) the data from the IMU and ii) the desired grip, and
cause the actuator module to perform the rotation for the prosthetic hand by actuating the rotatable portion.

16. The prosthetic hand and wrist system of claim 15, wherein the actuator module is configured to form the desired grip simultaneously with rotating the prosthetic hand.

17. The prosthetic hand and wrist system of claim 15, wherein the actuator module is configured to cause rotation of the prosthetic hand about two or more axes.

18. The prosthetic hand and wrist system of claim 15, wherein the IMU comprises a nine-axis IMU including three accelerometers, three gyroscopes and three magnetometers.

* * * * *